(12) United States Patent
Asfora et al.

(10) Patent No.: US 9,820,743 B2
(45) Date of Patent: Nov. 21, 2017

(54) SUTURELESS VASCULAR ANASTOMOSIS CONNECTION

(75) Inventors: Wilson Theophilo Asfora, Sioux Falls, SD (US); Thomas Albert Roberts, Morgan Hill, CA (US); Duane Lee Middlebusher, San Jose, CA (US); Richard Dean Phipps, Morgan Hill, CA (US); Michael Edward Villalta, Monte Sereno, CA (US); Lee James Carmack, Castro Valley, CA (US)

(73) Assignee: Asfora IP, LLC, Sioux Falls, SD (US)

( * ) Notice: Subject to any disclaimer, the term of this patent is extended or adjusted under 35 U.S.C. 154(b) by 316 days.

(21) Appl. No.: 12/983,204

(22) Filed: Dec. 31, 2010

(65) Prior Publication Data

US 2012/0123456 A1    May 17, 2012

Related U.S. Application Data

(63) Continuation of application No. 12/944,614, filed on Nov. 11, 2010, now Pat. No. 9,271,733.

(51) Int. Cl.
| | | |
|---|---|---|
| *A61B 17/11* | (2006.01) | |
| *A61B 17/08* | (2006.01) | |
| *A61F 2/06* | (2013.01) | |
| *A61B 90/00* | (2016.01) | |
| *A61B 17/10* | (2006.01) | |
| *A61B 17/56* | (2006.01) | |
| *A61B 17/00* | (2006.01) | |

(52) U.S. Cl.
CPC .............. *A61B 17/11* (2013.01); *A61B 17/08* (2013.01); *A61F 2/064* (2013.01); *A61B 17/10* (2013.01); *A61B 17/56* (2013.01); *A61B 2017/00867* (2013.01); *A61B 2017/00946* (2013.01); *A61B 2017/1107* (2013.01); *A61B 2017/1135* (2013.01); *A61B 2090/0811* (2016.02); *A61F 2220/0016* (2013.01)

(58) Field of Classification Search
CPC ................. A61B 17/11; A61B 17/1114; A61B 2017/1135; A61B 2017/1107; A61B 2017/1103; A61B 17/1128; A61B 17/1146; A61F 2/064
USPC ................. 606/153–156, 215, 216; 623/1.36
See application file for complete search history.

(56) References Cited

U.S. PATENT DOCUMENTS

| | | | |
|---|---|---|---|
| 4,884,572 A | | 12/1989 | Bays et al. |
| 5,203,864 A | | 4/1993 | Phillips |
| 5,250,058 A | * | 10/1993 | Miller et al. .................. 606/154 |
| 5,336,233 A | * | 8/1994 | Chen ............................ 606/153 |
| 5,397,355 A | | 3/1995 | Marin et al. |

(Continued)

OTHER PUBLICATIONS

Dictionary.com, definition of "diagonal," http://www.dictionary.com/browse/diagonal as accessed on Jun. 14, 2016 (5 pages).

*Primary Examiner* — Christopher L Templeton
(74) *Attorney, Agent, or Firm* — Dorsey & Whitney LLP

(57) ABSTRACT

Techniques for sutureless vascular anastomosis are described, including an incision seal including a base configured to partially house an outer surface of a main vessel, the base being formed using a material that is configured to be penetrated by a barb disposed on a connector the main vessel being secured to the base when the base is at least partially pierced by the barb, an upper lumen configured to guide a graft vessel, and a housing opening configured to receive the graft vessel.

11 Claims, 37 Drawing Sheets

(56) References Cited

U.S. PATENT DOCUMENTS

| | | | |
|---|---|---|---|
| 5,456,714 A * | 10/1995 | Owen | 623/1.31 |
| 5,486,186 A | 1/1996 | Yoon | |
| 5,496,332 A | 3/1996 | Sierra et al. | |
| 5,645,566 A | 7/1997 | Brenneman et al. | |
| 5,695,504 A | 12/1997 | Gifford, III et al. | |
| 5,702,048 A | 12/1997 | Eberlin | |
| 5,755,778 A | 5/1998 | Kleshinski | |
| 5,881,943 A | 3/1999 | Heck | |
| 5,893,369 A | 4/1999 | LeMole | |
| 6,007,576 A * | 12/1999 | McClellan | 623/23.64 |
| 6,030,395 A | 2/2000 | Nash et al. | |
| 6,036,705 A | 3/2000 | Nash et al. | |
| 6,063,114 A | 5/2000 | Nash et al. | |
| 6,113,612 A | 9/2000 | Swanson et al. | |
| 6,126,685 A | 10/2000 | Lenker | |
| 6,152,937 A | 11/2000 | Peterson et al. | |
| 6,193,734 B1 | 2/2001 | Bolduc et al. | |
| 6,210,429 B1 | 4/2001 | Vardi et al. | |
| 6,391,036 B1 | 5/2002 | Berg | |
| 6,428,550 B1 | 8/2002 | Vargas et al. | |
| 6,440,163 B1 | 8/2002 | Swanson | |
| 6,451,048 B1 | 9/2002 | Berg et al. | |
| 6,494,889 B1 | 12/2002 | Fleischman et al. | |
| 6,497,710 B2 * | 12/2002 | Yencho et al. | 606/153 |
| 6,511,491 B2 | 1/2003 | Grudem et al. | |
| 6,537,288 B2 | 3/2003 | Vargas et al. | |
| 6,599,303 B1 | 7/2003 | Peterson et al. | |
| 6,602,263 B1 | 8/2003 | Swanson et al. | |
| 6,616,675 B1 | 9/2003 | Evard et al. | |
| 6,620,176 B1 | 9/2003 | Peterson | |
| 6,682,540 B1 | 1/2004 | Sancoff et al. | |
| 6,695,878 B2 | 2/2004 | McGuckin, Jr. et al. | |
| 6,776,785 B1 * | 8/2004 | Yencho et al. | 606/153 |
| 6,911,035 B1 * | 6/2005 | Blomme | 606/153 |
| 6,960,219 B2 | 11/2005 | Grudem | |
| 6,972,023 B2 | 12/2005 | Whayne et al. | |
| 6,979,338 B1 | 12/2005 | Loshakove et al. | |
| 7,182,771 B1 | 2/2007 | Houser et al. | |
| 7,708,769 B1 * | 5/2010 | Manzo et al. | 623/1.1 |
| 8,012,164 B1 | 9/2011 | Donohoe et al. | |
| 8,162,963 B2 | 4/2012 | Abbott | |
| 8,366,651 B2 | 2/2013 | Dakin et al. | |
| 8,551,127 B2 | 10/2013 | Asfora et al. | |
| 2001/0029383 A1 | 10/2001 | Solem | |
| 2001/0041902 A1 * | 11/2001 | Lepulu et al. | 606/153 |
| 2002/0019659 A1 | 2/2002 | Goicoechea et al. | |
| 2002/0029050 A1 | 3/2002 | Gifford, III et al. | |
| 2002/0082625 A1 * | 6/2002 | Huxel et al. | 606/153 |
| 2002/0123786 A1 | 9/2002 | Gittings et al. | |
| 2002/0183769 A1 | 12/2002 | Swanson et al. | |
| 2002/0183825 A1 | 12/2002 | Solem | |
| 2003/0009183 A1 * | 1/2003 | Whayne | A61B 17/064 606/153 |
| 2003/0187499 A1 | 10/2003 | Swanson et al. | |
| 2004/0087984 A1 | 5/2004 | Kupiecki et al. | |
| 2004/0097993 A1 * | 5/2004 | Whayne | 606/153 |
| 2004/0102796 A1 | 5/2004 | Hill et al. | 606/153 |
| 2004/0116945 A1 * | 6/2004 | Sharkawy et al. | 606/153 |
| 2004/0181244 A1 * | 9/2004 | Lee | 606/153 |
| 2005/0192604 A1 * | 9/2005 | Carson et al. | 606/153 |
| 2005/0234483 A1 * | 10/2005 | Yencho et al. | 606/153 |
| 2005/0283173 A1 | 12/2005 | Abbott | |
| 2006/0089707 A1 * | 4/2006 | Vassiliades et al. | 623/1.23 |
| 2006/0144696 A1 | 7/2006 | Lee et al. | |
| 2008/0015617 A1 * | 1/2008 | Harari et al. | 606/153 |
| 2009/0076531 A1 * | 3/2009 | Richardson et al. | 606/153 |
| 2010/0063520 A1 * | 3/2010 | Bilotti | 606/153 |
| 2011/0118764 A1 * | 5/2011 | Beane et al. | 606/153 |
| 2011/0140413 A1 * | 6/2011 | Dittly et al. | 285/195 |
| 2012/0123451 A1 | 5/2012 | Asfora et al. | |
| 2012/0123452 A1 | 5/2012 | Asfora et al. | |
| 2012/0123453 A1 | 5/2012 | Asfora et al. | |
| 2012/0123454 A1 | 5/2012 | Asfora et al. | |
| 2012/0123456 A1 | 5/2012 | Asfora et al. | |
| 2012/0123512 A1 | 5/2012 | Asfora et al. | |
| 2012/0123513 A1 | 5/2012 | Asfora et al. | |

* cited by examiner

SUTURELESS VASCULAR ANASTOMOSIS CONNECTION

CROSS-REFERENCE TO RELATED APPLICATIONS

This application is a continuation of U.S. patent application Ser. No. 12/944,614 filed Nov. 11, 2010 entitled "SUTURELESS VASCULAR ANASTOMOSIS CONNECTION," related to co-pending U.S. patent application Ser. No. 12/946,703 filed Nov. 15, 2010 entitled "SUTURELESS VASCULAR ANASTOMOSIS CONNECTION," which is a continuation of U.S. patent application Ser. No. 12/944,614, related to co-pending U.S. patent application Ser. No. 12/981,406 filed Dec. 29, 2010 entitled "SUTURELESS VASCULAR ANASTOMOSIS CONNECTION," which is a continuation of U.S. patent application Ser. No. 12/944,614, related to co-pending U.S. patent application Ser. No. 12/982,891 filed Dec. 31, 2010 entitled "SUTURELESS VASCULAR ANASTOMOSIS CONNECTION," which is a continuation of U.S. patent application Ser. No. 12/944,614, and related to Co-pending U.S. patent application Ser. No. 12/983,037 filed Dec. 31, 2010 entitled "SUTURELESS VASCULAR ANASTOMOSIS CONNECTION," which is a continuation of U.S. patent application Ser. No. 12/944,614, all of which are herein incorporated by reference for all purposes.

FIELD OF THE INVENTION

The present invention relates generally to anastomosis, and more specifically, to techniques for sutureless vascular anastomosis.

BACKGROUND OF THE INVENTION

Generally, anastomosis refers to the connection of blood vessels or other structures that may be found in the human body. Conventional solutions for vascular anastomosis typically refer to the use of devices and surgical procedures in which one vessel is surgically joined to another vessel. This procedure is required for a variety of medical procedures, including procedures involving redirection of bodily fluids such as blood within the patient. One conventional example is a cranial bypass procedure that diverts a portion of the flow of a temporal artery located outside of a skull to one or more arteries within the skull in order to provide additional blood flow to a patient's brain.

When performing any form of vascular anastomosis, a major concern is that the flow of bodily fluid must be interrupted for the duration of the procedure. This interruption of flow, if too long, causes detrimental effects to organs and surrounding tissue, which can endanger, jeopardize, or worsen a patient's general health.

Currently, a common conventional method of vascular anastomosis includes manually applying a number of sutures to create a fluid-impermeable seal between two vessels. This process is not only difficult, time consuming, and expensive, but also requires a high degree of surgical skill and a considerable amount of time and patience from a surgeon. Additionally, the use of sutures introduces a potential weakness in a surgical connection placed to connect two or more vessels, often resulting in tearing or leakage. Further, a surgeon is often required to test a conventional anastomosis connection between two vessels to ensure that the sutures have created a fluid impermeable seal. A leak resulting from poor or weakened sutures can create a number of problems such as internal hemorrhaging for the patient, requiring additional surgeries, time, and expense. Also problematic are conventional connectors used in anastomosis procedures that are often bulky, unwieldy, or difficult to use, typically requiring significant skill and specialized equipment that can be expensive to manufacture and purchase. Further, the time required for submission, review, and governmental approval of applications for the use of elaborate medical devices in humans for anastomosis applications is substantial, incurring significant social and health care costs due to the delay. Some conventional solutions used in applications such as side-to-end vascular anastomosis often require more time, expertise, and effort since joining an end of a vessel to a side of another vessel is more time-consuming and skill-intensive than joining an end of a vessel to an end of another vessel.

Thus, a solution for more vascular anastomosis without the limitations of conventional techniques is desired.

BRIEF DESCRIPTION OF THE DRAWINGS

Various examples are disclosed in the following detailed description and the accompanying drawings.

DETAILED DESCRIPTION

Embodiments or examples of the invention may be implemented in numerous ways, including as an apparatus, system, or process. A detailed description of one or more examples is provided below along with accompanying figures. The detailed description is provided in connection with such examples, but is not limited to any particular example. The scope is limited by the claims, but numerous alternatives, modifications, and equivalents are encompassed. Numerous specific details are set forth in the following description in order to provide a thorough understanding. These details are provided for the purpose of example and the descriptions provided may be used for implementation according to the claims without some or all of these specific details. For the purpose of clarity, technical material that is known in the technical fields related to the examples has not been described in detail to avoid unnecessarily obscuring the description.

Various techniques and devices for sutureless vascular anastomosis are described, including a connector and an incision seal system that may be configured and used to join, seal, or otherwise couple a first vessel to a second vessel without the use of sutures. In some examples, the first vessel and second vessel pair may be a graft vessel and main vessel pair, a donor vessel and recipient vessel pair, or any other pair of vessels. As used herein, a graft vessel may be referred to as a "donor" vessel, artery, vein, or the like. Also and as used herein, a main vessel may be referred to as a "recipient" vessel, artery, or the like. These terms may be used interchangeably without limitation. For example, the graft vessel may be a superficial temporal artery (STA) and the main vessel may be a mid cranial artery (MCA). In other examples, the graft and main vessels may be other arteries, vessels, veins, or vascular structures and are not limited to any specific types or structures. Exemplary connectors may be configured to couple a graft vessel to a main vessel to provide a lumen (i.e., a channel, passageway, artery, vein, or the like) to transfer fluids (e.g., blood) between a graft vessel and a main vessel. After an exemplary connector has coupled a graft vessel to a main vessel, an exemplary incision seal may be engaged with the connector to seal the graft vessel to the main vessel. In some examples, an incision seal may be configured to lock, mate, or otherwise connect with a connector. In some examples, the coupling of a connector with an incision seal may create a clamping force that secures a portion of an upper wall of the main vessel between the incision seal and the connector. In other examples, the described systems may be varied in design, function, structure, or implementation and are not limited to the techniques described below.

Figure 1:
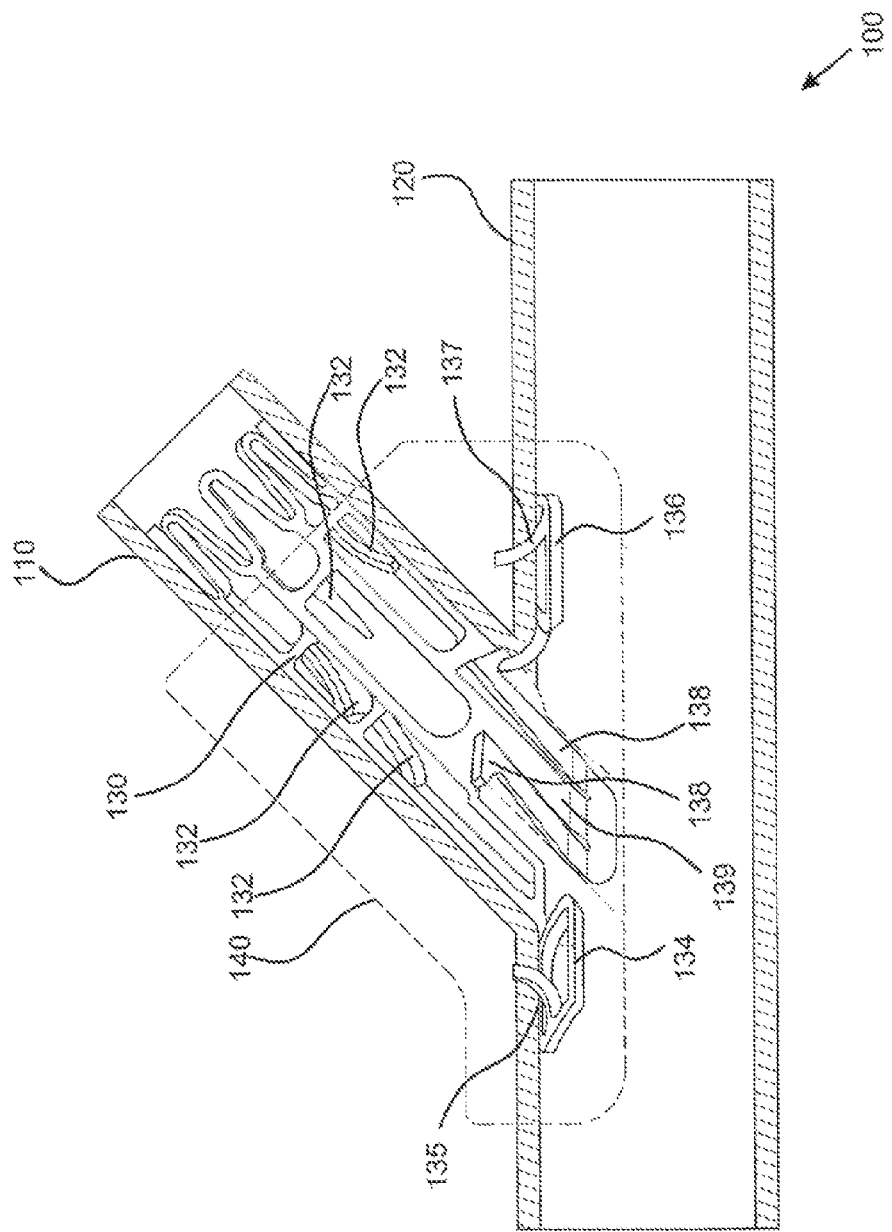
FIG. 1 illustrates an exemplary sutureless vascular anastomosis connector system.

FIG. 1 illustrates an exemplary sutureless vascular anastomosis system. Here, system 100 includes graft vessel 110, main vessel 120, connector 130, tines 132, front wing 134, rear wing 136, tines 135 and 137, side wing 139, barbs 138, and incision seal 140. In some examples, connector 130 may be fabricated, manufactured, or otherwise formed using various types of medical-grade material, including stainless steel, plastic, composites of any type, and alloys such as nickel titanium, Nitinol™ (e.g., Nickel Titanium Naval Ordnance Laboratory) or super elastic Nitinol™. For example, if Nitinol™ is used, it may be formed at various pressures and temperatures in order to provide for a memory shape where front wing 134, rear wing 136, side wing 139, and barbs 138 are deployed. As another example, super elastic Nitinol™ may be configured to behave similar to a spring when a restraining force is removed. In yet other examples, materials may be used such that when formed, a "material memory" is created in a given shape of connector 130. In other words, connector 130 may be formed such that when a restraining force is removed, a given shape is assumed. When placed into a restrained shape and inserted into main vessel 120, the restraining force may be removed to allow front wing 134 and rear wing 136 to deploy securely and engage into the tissue of the upper wall of main vessel 120 using tines 135 and 137. As another example, alloys may be used to form connector 130 such that when placed into a fluid (e.g., blood) stream such as that within main vessel 120, the heat of the surrounding fluid may cause memory material used to form connector 130 to change shape (e.g., deploy front wing 134 and rear wing 136). In other examples, connector 130 may be formed differently and is not limited to the examples described.

Here, connector 130 may be configured to couple graft vessel 110 to main vessel 120 in a sutureless manner. Once coupled, fluids may pass between graft vessel 110 and main vessel 120. As an example, incision seal 140 may be coupled to connector 130 to provide a leak-proof seal between graft vessel 110 and main vessel 120.

As shown here, connector 130 may include tines 132, front wing 134, and rear wing 136. These portions of connector 130 may be configured to securely engage connector 130 with graft vessel 110 and main vessel 120. For example, tines 132 may be configured to securely engage an inner surface of graft vessel 110 while front wing 134 and rear wing 136 may be configured to securely engage an inner surface of main vessel 120. Tines 132 may prevent the connector from being displaced with respect to the graft vessel when the connector is coupled to the graft vessel. In some examples, connector 130 may further include barb 138 for coupling connector 130 with incision seal 140. Barb 138 may be configured to puncture a portion of a wall of main vessel 120 and lock with incision seal 140. For example, incision seal 140 may include a slot configured to lock with barb 138. In another example, incision seal 140 may comprise of a malleable material configured to receive and lock with barb 138. For example, the incision seal may be formed of medical grade silicone. Locking connector 130 with incision seal 140 may secure the juncture of graft vessel 110 and main vessel 120 between connector 130 and incision seal 140. This may allow graft vessel 110 to securely contact main vessel 120, thus creating a leak-free seal. Over time, graft vessel 110 and main vessel 120 may graft with one another and form an integrated vessel. In some examples, system 100 may replace barb 138 and the slot with other fasteners. Other fasteners may include hooks, clamps, screws, cables, and adhesives to name a few. It should be understood by those skilled in the art that a "barb" may be replaced with a first part of a fastener and that a "slot" may be replaced with a second part of a fastener in this specification. In other examples, the shape and configuration of connector 130, tine 132, front wing 134, rear wing 136, tines 135 and 137, barb 138, and incision seal 140 may be implemented differently and are not limited to the examples shown and described. For example, the wings, tines, or barbs may vary in number, shape, and placement.

In some examples, one or more portions of connector 130 may include a memory material that causes the one or more portions to change shape. As used herein, "memory material" may refer to any material that, when formed, shaped, fabricated, poured, deposited, or otherwise implemented has a material property that allows for a physical shape under a given set of conditions (e.g., temperature, pressure, or the like) and assumes a different physical shape when one or more conditions change. For example, a memory material may cause a portion of connector 130 to assume one shape when a restraining force is applied and then assume another shape when the restraining force is removed. In another example, the memory material may cause the portion to be spring loaded such that the portion springs from a first position into a second position when a restraining force is removed. As shown here, front wing 134 may include a memory material that causes front wing 134 to align with an outer surface of the end of connector 130 when a restraining force is applied. This characteristic may allow connector 130 to maintain a cylindrical shape when inserting into main vessel 120. Front wing 134 may also deploy or swing away from the end of connector 130 when the restraining force is removed. This characteristic may allow front wing 134 to deploy and securely engage the inner surface of main vessel 120 after connector 130 has been inserted into main vessel 120. In other examples, the above-described elements may be implemented differently and are not limited to the examples shown and described.

Figure 2:
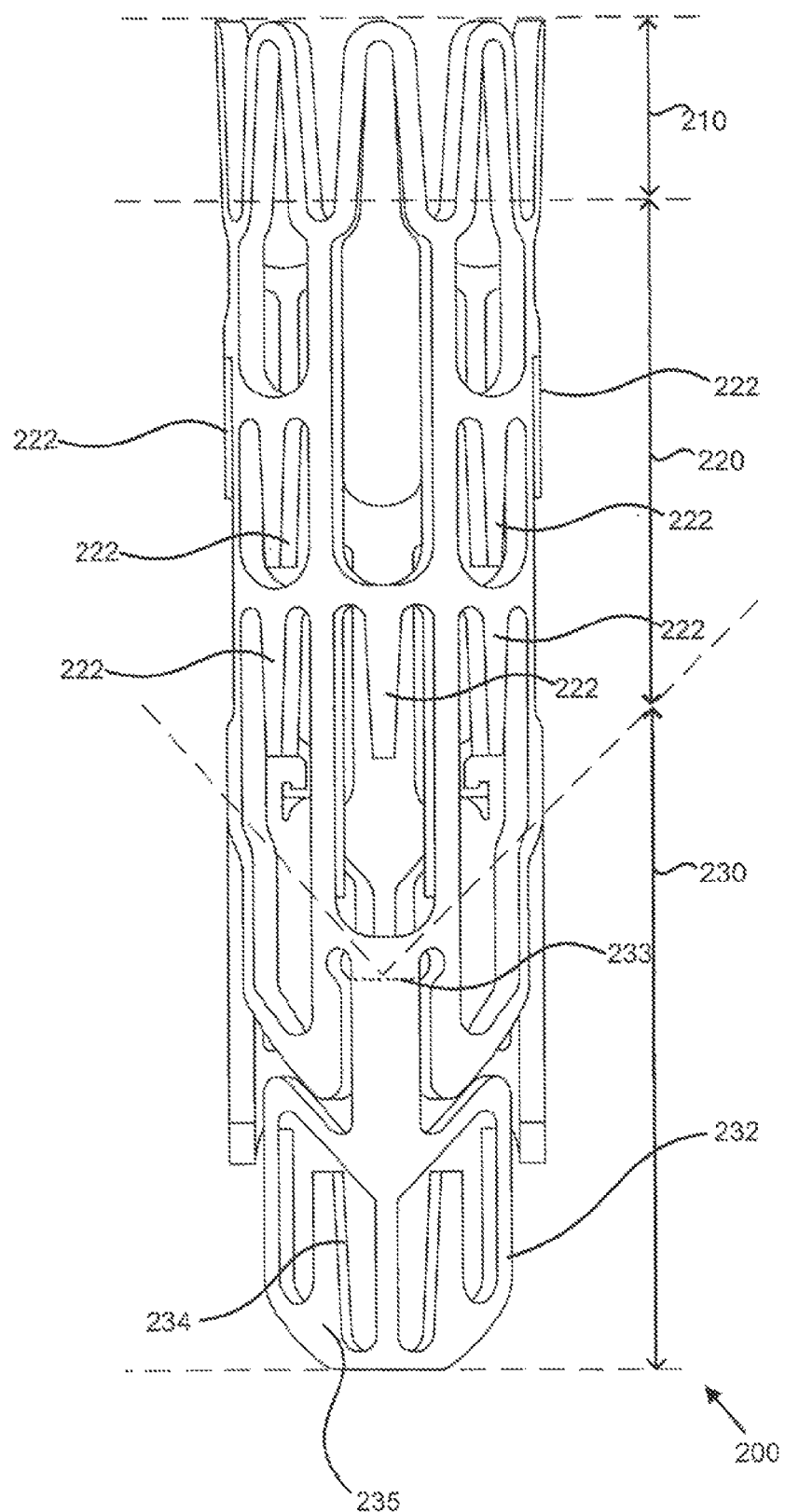
FIG. 2 illustrates a front view of an exemplary sutureless vascular anastomosis connector.

FIG. 2 illustrates a front view of an exemplary sutureless vascular anastomosis connector. Here, connector 200 includes connector tip 210, connector body 220, tines 222, and connector base 230. In an example, connector tip 210, connector body 220, and connector base 230 may be integrated with connector 200. For example, these parts of connector 200 may form a continuous tubular structure that may be configured to serve as a lumen for fluid transfer between two ends of connector 200. In another example, connector tip 210, connector body 220, and connector base 230 may be separate structures that are coupled together to form connector 200.

In some examples, an interior of connector 200 may serve as a lumen for fluid transfer between a graft vessel coupled to one end of connector 200 and a main vessel coupled to another end of connector 200. The rate of fluid transfer through connector 200 may depend upon the cross-sectional area of connector 200. In other examples, connector 200 may be made of a memory material. The memory material may provide flexibility to connector 200. For example, this flexibility may allow connector 200 to slightly flex when forces are applied to connector 200. The forces may be an external force applied to an external surface of connector 200 or an internal force applied to an internal surface of connector 200. Alternatively, the flexibility may provide functionality to connector 200. For example, the memory material may allow portions of connector 200 to change shape or position. The changes in shape or position may assist in securing a graft vessel to a main vessel.

As shown here, connector base 230 may be disposed at an end of connector 200. In some examples, connector base 230 may be configured to securely engage a main vessel. For example, connector base 230 may be configured to securely engage a main vessel through an incision in a wall of the main vessel. This may include inserting connector base 230 into the main vessel and securely engaging connector base 230 with an inner wall of the main vessel. Connector base 230 may include front wing 232. In some examples, front wing 232 may be composed of a memory material that causes front wing 232 to change shape or position based upon external forces. For example, front wing 232 may be configured to be substantially planar (or aligned) with an outer surface of connector 200 when a restraining force is applied to front wing 232. The restraining force may be caused by elastic bands, sheaths, wrappers, or other physical elements. Alternatively, the restraining force may be caused by the temperature or chemical attributes of the environment surrounding connector 200. For example, the temperature of connector 200 may affect the restraining force or the chemical composition of a fluid coming into contact with connector 200 may affect the restraining force. In one application, it may be easier to insert connector 200 into the incision in the wall of the main vessel when front wing 232 is substantially planar with an outer surface of connector 200.

Front wing 232 may also be configured to deploy from connector 200 when the restraining force is removed. For example, front wing 232 may be configured to swing away from connector base 230 at front wing junction 233 when the restraining force is removed. In other examples, front wing 232 may be configured swing away from connector base 230 not as a junction, but by bending one or more sections of front wing 232. When deployed, front wing 232 may be configured to engage an inner surface of an upper wall of the main vessel. Further discussion of this deployed state is included below in FIG. 5, FIG. 6, and FIG. 7. In other examples, connector base 230 may be implemented and configured differently and is not limited to the descriptions provided.

In some examples, front wing 232 may include front tine 234. Front tine 234 may be configured to securely engage with an inner surface of a vessel. For example, front tine 234 may provide the securing means to securely engage front wing 232 to an inner surface of an upper wall of the main vessel. As shown here, one end of front tine 234 may be coupled to front wing 232 while the other end of front tine 234 remains unfixed. In some examples, front tine 234 may be composed of a memory material that causes front tine 234 to change shape or position based upon external forces. The memory material may be similar or substantially similar to the memory material described in front wing 232 of FIG. 2. For example, front tine 234 may be configured to be substantially planar (or aligned) with an outer surface of connector 200 when a restraining force is applied to front tine 234. In other words, the unfixed end of front tine 234 may be aligned with an outer surface of connector 200. This configuration may be desirable when inserting connector 200 into the incision in the wall of the main vessel as it prevents the unfixed end of front tine 234 from snagging or catching onto an edge of the incision during insertion.

Alternatively, front tine 234 may be configured to deploy from front wing 232 when the restraining force is removed. For example, front tine 234 may be configured to swing away from front wing 232 at front tine junction 235 when the restraining force is removed. In another example, front tine 234 may be configured to form a curved shape when the restraining force is removed. When deployed, front wing 232 may be configured to securely engage an inner surface of an upper wall of the main vessel. In some examples, front tine 234 and front wing 232 may deploy simultaneously or in a specific order as determined by the attributes of the memory material used in front tine 234 and front wing 232. Further discussion of this deployed state is included below in FIG. 5, FIG. 6, and FIG. 7. In other examples, connector tine 234 may be implemented differently and are not limited to the examples shown and described.

As shown here, connector body 220 may be integrated as part of connector 200 and coupled to connector base 230. In some examples, connector body 220 may include body tine 222. Body tine 222 may be implemented similarly or substantially similar in function and structure to front tine 234. In some examples, body tine 222 may be configured to securely engage with an inner surface of a graft vessel. An unfixed end of body tine 222 may provide a constant force against the inner surface of the graft vessel that allows connector body 222 to be inserted into the graft vessel but does not allow connector body 222 to be pulled out of the graft vessel. In other examples, connector body 220 may be implemented differently and are not limited to the examples shown and described.

As shown here, connector tip 210 may be integrated with connector 200 and disposed at an end of connector 200. In some examples, connector tip 210 may be configured to be inserted into a graft vessel. To assist in the insertion process, connector tip 210 may be configured to compress when a substantially tangential force is applied to connector tip 210. This force may cause the end of connector 200 to shrink, thus simplifying the task of inserting the end of connector 200 into the graft vessel. In other examples, connector tip 210 may be configured to maintain in the shape of connector tip 210 when a substantially tangential force is applied to connector 200. Changes in the shape of connector tip 210 may be undesirable as they may result in pinching or otherwise limiting the flow of fluids through connector 200. Here, connector tip 210 comprises a wave-shaped pattern. The wave-shaped pattern is similar to a sinusoidal wave and is configured to provide a compressible end to connector 200. Furthermore, the wave-shaped pattern may retain its shape when substantially tangential forces are applied to connector body 220. In other examples, the above-described elements may be implemented differently and are not limited to the examples shown and described.

Figure 3:
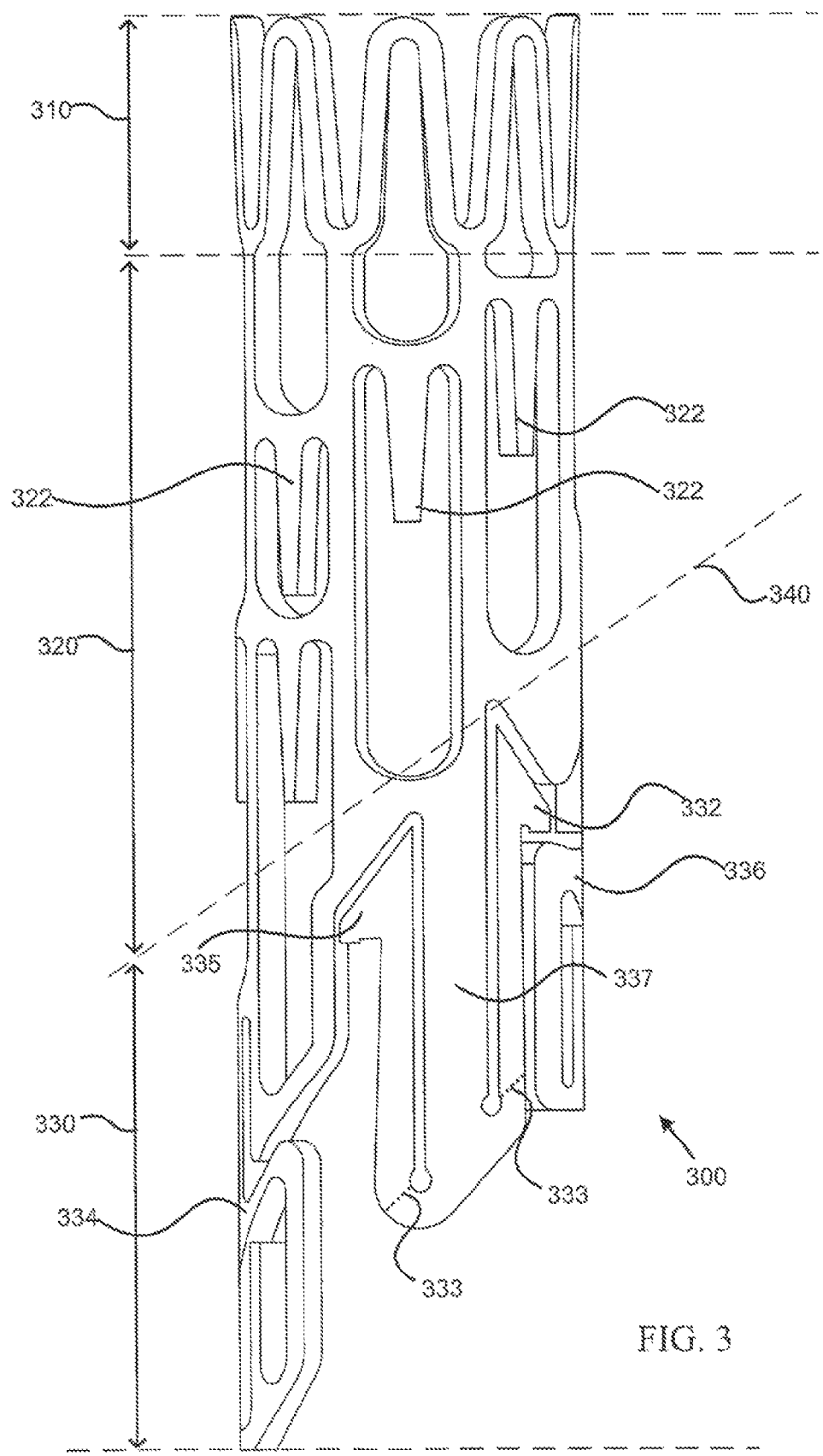
FIG. 3 illustrates a side view of an exemplary sutureless vascular anastomosis connector.

FIG. 3 illustrates a side view of an exemplary sutureless vascular anastomosis connector. Here, connector 300 includes connector tip 310, connector body 320, body tines 322, connector base 330, barbs 332 and 335, barb junction 333, front wing 334, rear wing 336, and side wing 337. Connector tip 310, connector body 320, body tines 322, and connector base 330 may be implemented similarly or substantially similar in function and structure to like-named elements as shown and described in FIG. 2. As shown here, connector body 320 and connector base 330 may intersect along diagonal plane 340. In some examples, diagonal plane 340 may represent an angle in which connector 300 and an attached graft vessel are coupled with the main vessel. Thus, modifying diagonal plane 340 may alter the angle in which the graft vessel is coupled with the main vessel.

Connector base 330 may include barb 332, barb 335, front wing 334, side wing 337, and rear wing 336. In some examples, barbs 332, barb 335, front wing 334, and rear wing 336 may be configured to couple connector base 330 with the main vessel. In other examples, barbs 332 and 335, front wing 334, rear wing 336, and side wing 337 may be composed of a memory material with similar functionality as the memory material described above in FIG. 1 and FIG. 2. As an example, the memory material may cause barb 332, barb 335, front wing 334, or rear wing 336 to change shape or position based upon external forces.

Barb 332 may be configured to be substantially planar with an outer surface of connector 300 when a restraining force is applied to connector barb 332. Alternatively, barb 332 may be configured to deploy from connector 300 when the restraining force is removed. As an example, barb 332 may bend at barb junction 333 when a restraining force is removed, thus deploying barb 332 from connector base 330. Alternatively, the entire body of barb 332 may bend away from connector base 330. In other examples, barb 332 may bend at different locations to deploy barb 332 from connector base 330. In some examples, barb junction 333 and side wing 337 may bend simultaneously or in a specific order to deploy barb 332 from connector base 330. In other examples, barb 335 may be configured to function similar to barb 333.

Front wing 334 and rear wing 336 may be configured to be substantially planar with an outer surface of connector 300 when a restraining force is applied to front wing 334 and rear wing 336. Alternatively, front wing 334 and rear wing 336 may be configured to deploy from connector 300 when the restraining force is removed. In some examples, front wing 334 and rear wing 336 may be implemented similarly or substantially similar in function and structure to front wing 232 as shown and described in FIG. 2. In an example, front wing 334 and rear wing 336 may be substantially parallel with diagonal plane 340 when deployed. This may allow front wing 334 and rear wing 336 to contact the inner surface of a main vessel when deployed. Further discussion of this deployed state is included below in FIG. 5, FIG. 6, and FIG. 7. In other examples, the above-described elements may be implemented differently and are not limited to the examples shown and described.

Figure 4:
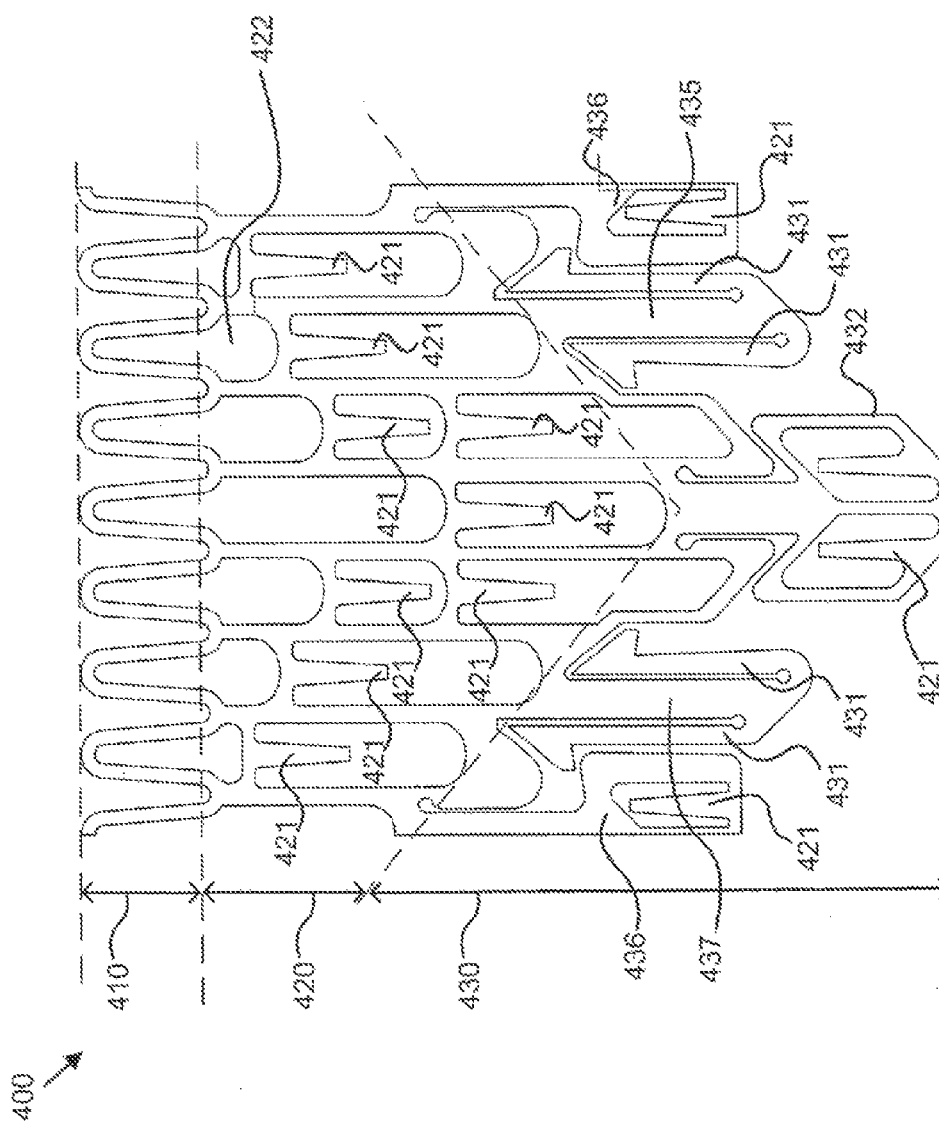
FIG. 4 illustrates a flat pattern of an exemplary sutureless vascular anastomosis connector.

FIG. 4 illustrates a flat pattern of an exemplary sutureless vascular anastomosis connector. Here, flat pattern 400 includes connector tip 410, connector body 420, tines 421, pattern 422, connector base 430, barbs 431, front wing 432, side wings 435 & 437, and rear wing 436. In some examples, connector 200 in FIG. 2 or connector 300 in FIG. 3 may be formed by applying flat pattern 400 to a tubular structure. For example, a laser cutting apparatus may apply flat pattern 400 to a tube comprising memory material to create connector 200 in FIG. 2 or connector 300 in FIG. 3. As shown here, flat pattern 400 may include connector tip 410, connector body 420, and connector base 430. Connector tip 410, in some examples, may be formed to resemble a "wave" such that, when formed in a substantially circular implementation, a wave-shaped muzzle is formed. In some examples, connector tip 410, connector body 420, and connector base 430 may be implemented similarly or substantially similar in function and structure to same-named elements in FIG. 2 and FIG. 3.

Connector body 420 may also include pattern 422. Pattern 422 may be a mesh pattern, a wire frame pattern, a plurality of perforations, or any combination of openings. In some examples, pattern 422 may be configured to allow connector body 420 to graft with a surface of a vessel. When grafted, the connector and the vessel may be securely coupled to one another. As shown here, pattern 422 may be a wire frame. When inserted into a graft vessel, the wire frame may selectively contact the inner surface of the graft vessel. Over time, tissue along the inner surface of the graft vessel may attach to the wire frame. This may lead to the integration of the wire frame as part of the graft vessel.

In other examples, pattern 422 may be configured to control, adjust, or modify the flexibility of connector body 420. The direction or location of flex may be controlled, adjusted, or modified depending upon pattern 422. In an example, the width and orientation of pattern 422 may control the direction, the location, and the amount of flex in connector body 420 when external forces are applied to connector body 420. In some examples, the direction and amount of flex may be configured to prevent pinching or other limitations to the flow of fluids through connector body 420. In other examples, the amount of flex may be configured to relieve pressure to the wall of the graft vessel. For example, when external forces are applied to the wall of a graft vessel, pressure on the wall of the graft vessel may result. A connector body that is flexible may slightly bend in the presence of pressure, therefore relieving and dampening the pressure. This may minimize damage to the wall of the graft vessel. In other examples, the above-described elements may be implemented differently and are not limited to the examples shown and described.

Figure 5:
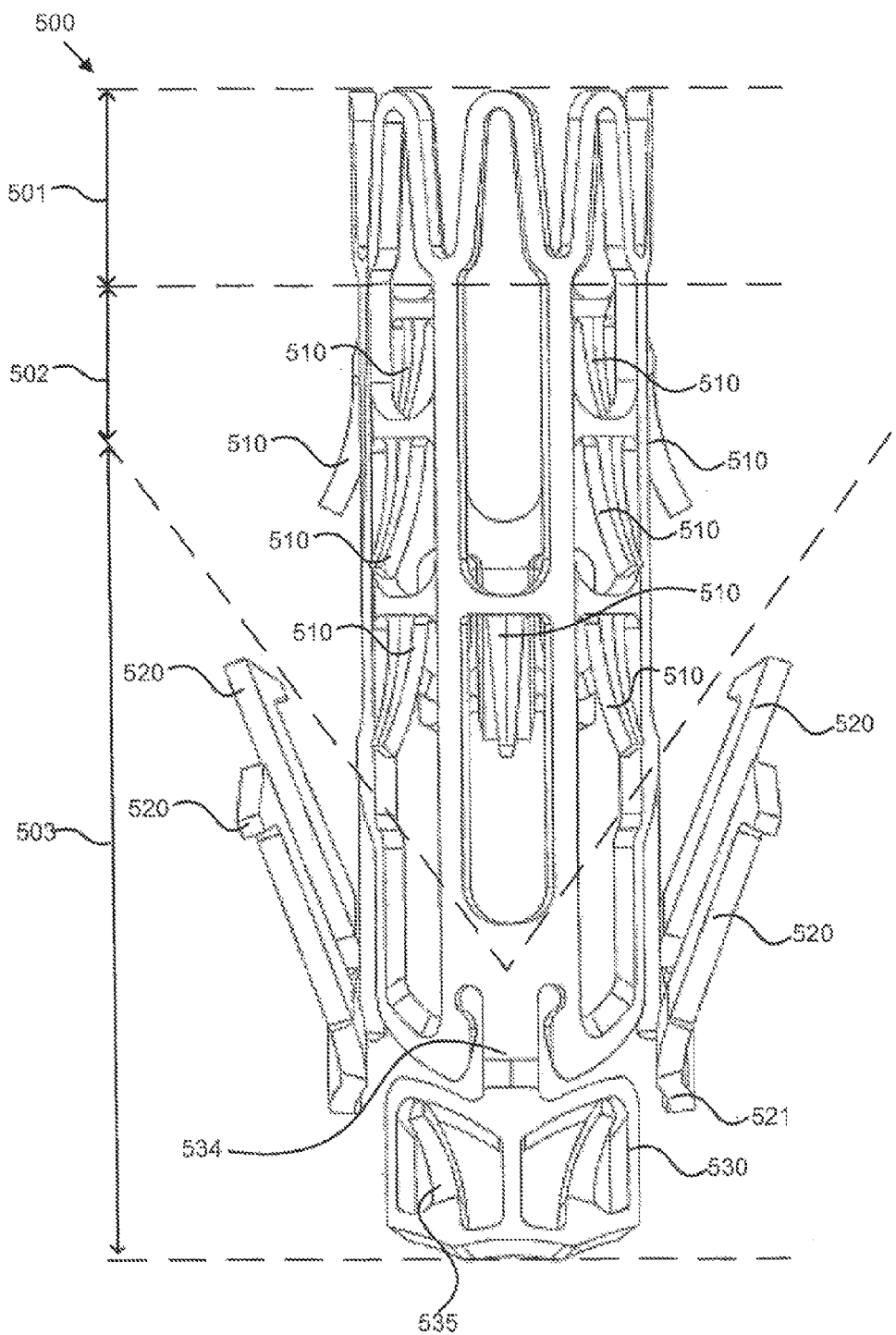
FIG. 5 illustrates a front view of an exemplary sutureless vascular anastomosis connector.

FIG. 5 illustrates a front view of an exemplary sutureless vascular anastomosis connector. In some examples, connector 500 may be made of a memory material that allows connector 500 to change shape. Here, connector 500 includes connector tip 501, connector body 502, connector base 503, body tines 510, barbs 520, front wing 530, and front tine 535. Connector tip 501, connector body 502, connector base 503, body tines 510, barb 520, front wing 530, and front tine 535 may be implemented similarly or substantially similar in function and structure to like-named elements as shown and described in FIG. 2 and FIG. 3. As shown here, body tines 510, barb 520, front wing 530, and front tine 535 may be configured to deploy from connector 500. In some examples, body tines 510, barb 520, front wing 530, and front tine 535 may deploy when a restraining force is removed.

Body tines 510, when deployed, may have a fixed end attached to connector body 502 and an unfixed end curving away from connector body 502. The radius of curvature of body tines 510 may be predetermined. Alternatively, the unfixed end may bend away from connector body 502 at a junction. In examples where body tines 510 are made of a memory material, the unfixed end may be disposed when a force is applied to the unfixed end. The displacement may cause the radius of curvature of body tines 510 to change. In some examples, the amount of displacement may depend upon the shape of body tines 510 or the material memory in body tines 510. For example, a thinner body tine may be easier to bend than a thicker body tine, thus resulting in a larger change in radius of curvature when the force is applied. In another example, body tines 510 may be configured to not break or crack when force is applied. When disposed, the unfixed end may exert an opposing force as the applied force. The opposing force may attempt to return body tines 510 to its predetermined shape. As an example, the opposing force may be in the opposite direction as the applied force. In other examples, the opposing force may be depend upon the radius of curvature of body tines 510 or the material memory in body tines 510. For example, the opposing force may be directly proportional to the radius of curvature of body tines 510. Alternatively, the opposing force may be constant. When the applied force is removed from body tines 510, body tines 510 may return its predetermined radius of curvature and the opposing force may no longer exist.

Connector body 502 may be configured to be inserted into a graft vessel. In some examples, an inner diameter of the graft vessel may be the same or substantially the same as an outer diameter of connector body 502. When connector body 502 is inserted, rolled, or otherwise disposed alongside the outer surface of the graft vessel, the insertion may cause an inner surface of the graft vessel to apply a force on the unfixed end of body tines 510, thus displacing body tines 510. In response, body tines 510 may exert an opposing force on the inner surface of the graft vessel. Depending on the orientation of body tines 510, the opposing force may cause the unfixed end of body tines 510 to securely engage the inner surface of the graft vessel, thus preventing connector body 502 from moving in a specified direction. For example, body tines 510 may be configured to restrict the graft vessel from moving in the opposite direction as the unfixed end while allowing a graft vessel to move in the same direction as the unfixed end. In other words, the orientation of body tines 510 may affect the allowable direction of movement between connector 500 and the graft vessel. As shown here, the unfixed end of body tine 522 may be pointed towards connector base 503 and thus preventing the graft vessel from being pulled back after insertion has taken place. In yet other examples, connector body 502 may contain more body tines to better control or limit the movement of the graft vessel with respect to connector 500.

Barb 520, when deployed, may have a fixed end attached to connector base 503 and an unfixed end that deploys from connector base 503. In an example, the unfixed end may be coupled to a deployable side wing (similar to side wing 337 in FIG. 3) and be configured to swing away from the outer surface of connector base 503 at barb junction 521. The deployable side wing and barb 520 may together provide a wide variety of deployment configurations varying in position and angle for barb 520. In some examples, the unfixed end may be configured to puncture an upper wall of a main vessel and engage with a slot in an incision seal. For example, the unfixed end of barb 520 may be shaped as a half arrow that is configured to puncture the wall of the main vessel and not be readily removable from the wall of the main vessel once punctured. As another example, the unfixed end of barb 520 may include a sharp end and a protrusion. The sharp end may be configured to puncture the wall of the main vessel while the protrusion may be configured to lock with a slot. When locked with the slot in the incision seal, connector 500 and the incision seal may provide a clamping force to a portion of the wall of the main vessel. To disengage the incision seal from connector 500, a surgeon may exert a force on the protrusion to cause barb 520 to unlock with the slot. As shown here, barb 520 may be angled away from connector 520 when in a deployed state. However, it is understood that barb 520 may also deploy at different angles. In other examples, the above-described elements may be implemented differently and are not limited to the examples shown and described.

Figure 6:
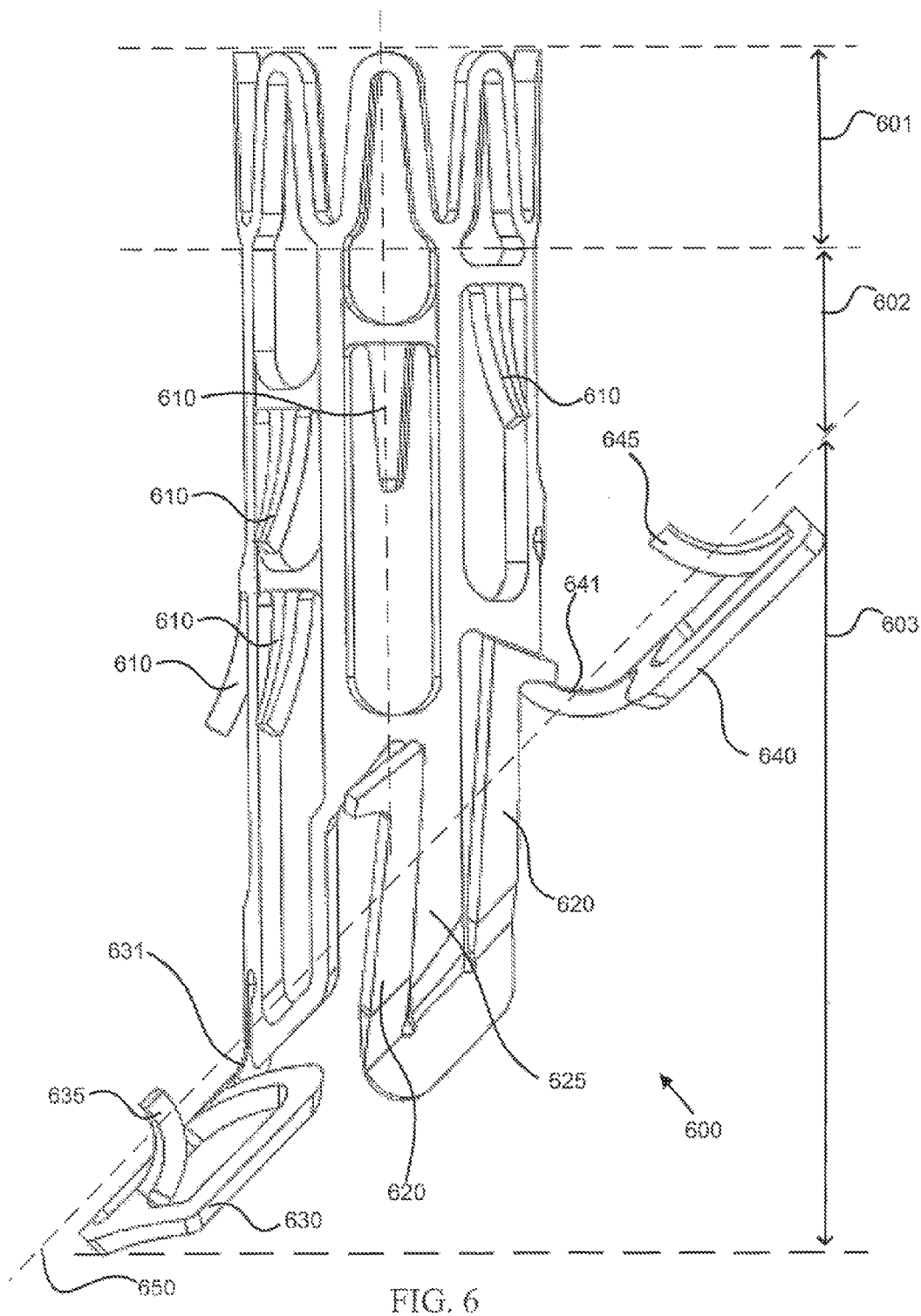
FIG. 6 illustrates a side view of an exemplary sutureless vascular anastomosis connector.

FIG. 6 illustrates a side view of an exemplary sutureless vascular anastomosis connector. In some examples, connector 600 may be made of a memory material that allows connector 600 to change shape. Here, connector 600 includes connector tip 601, connector body 602, connector base 603, body tines 610, barbs 620, side wing 625, front wing 630, front tine 635, rear wing 640, and rear tine 645. Connector tip 601, connector body 602, connector base 603, body tine 610, and barb 620 may be implemented similarly or substantially similar in function and structure to like-named elements as shown and described in FIG. 2, FIG. 3, and FIG. 5. As shown here, body tine 610, barb 620, side wing 625, front wing 630, and rear wing 640 may be configured to deploy from connector 600. In some examples, body tine 610, barb 620, side wing 625, front wing 630, or rear wing 640 may deploy when a restraining force is removed.

As shown here, front wing 630 and rear wing 640 may be disposed on opposing sides of connector base 603. In some examples, front wing 630 and rear wing 640 may be configured to swing away from connector base 603 when deployed. For example, when connector base 603 has been inserted into a main vessel, front wing 630 and rear wing 640 may swing away from connector base 603 and engage an inner surface of the main vessel. In other examples, front wing 630 and rear wing 640 may be configured to swing away from connector base 603 until front wing 630 and rear wing 640 are substantially parallel with one another. Here, front wing 630 and rear wing 640 may be swing away from connector base 630 until they are substantially aligned with plane 650. Plane 650 may represent the intersection between connector body 602 and connector base 603. In some examples, plane 650 may divide the connector 600 into two portions, the first portion remaining inside the main vessel and the second portion remaining outside the main vessel.

In some examples, the mechanical motion resulting from front wing 630 and rear wing 640 swinging away from connector base 603 may be different. For example, front wing 630 may swing away from connector base 603 at front hinge 631. This may allow front wing 630 to substantially maintain its shape while changing its position or orientation. Similarly, rear wing 640 may swing away from connector base 603 at rear hinge 641. In other examples, the shape or the radius of curvature of front wing 630 may change when being deployed. For example, the shape of front wing 630 may change to conform with the inner surface of a main vessel when front wing 630 is deployed. Front wing 630 may change curvature, orientation, or shape in order to remain substantially flush with an inner surface of the main vessel. In some examples, rear wing 640 may be implemented similarly or substantially similar in function and structure to front wing 630.

Front wing 630 may include front tine 635. In some examples, front tine 635 may be implemented similarly or substantially similar in function and structure to body tine 510 in FIG. 5. When deployed, front tine 635 may include a fixed end attached to front wing 630 and an unfixed end curving away from front wing 630. As an example, the unfixed end of front tine 635 may be configured to contact, penetrate, or grasp an inner surface of the main vessel. In other words, front tine 635 may be configured to securely engage with the main vessel. In some examples, the curvature, orientation, and shape of front tine 635 may affect the way or manner that front tine 635 securely engages with the main vessel. For example, the unfixed end of front tine 635 may be configured to securely engage with the inner surface of the main vessel in a unidirectional manner. As shown here, front tine 635 may be configured to prevent removing the main vessel away from connector 600. When the main vessel is moved away from connector 600, the unfixed end of front tine 635 may engage with the inner surface of the main vessel to prevent movement in that direction. In some examples, the engagement may be by penetrating or grasping the inner surface of the main vessel. Alternatively, front tine 635 may be configured to not engage with the inner surface of the main vessel when the main vessel moves towards connector 600. In other words, front tine 635 may be configured to allow the main vessel to move towards connector 600. In some examples, rear tine 645 may be implemented similarly or substantially similar in function and structure to front tine 635. In other examples, front wing 630 and front tine 635 may be configured to operate, as a single unit.

In some examples, front tine 635 and rear tine 645 may be configured to support an incision in a wall of the main vessel. Support may include preventing connector 600 from undesirable movements that may expand, stretch or otherwise enlarge the size of the incision. An enlarged incision may be too large to be sealed by the connector and the incision seal without the use of sutures. Thus, it may be desirable to limit the movements of connector 600 once connector 600 has been secured to the main vessel. For example, front tine 635 and rear tine 645 may be configured to prevent undesirable axial movements from connector 600 by piercing and grasping onto an inner surface of the main vessel. In another example, front tine 635 and rear tine 645 may be configured to prevent undesirable longitudinal movements from connector 600. As shown here, the unfixed ends of front tine 635 and rear tine 645 may be configured to point towards connector 600. In this configuration, front tine 635 and rear tine 645 may work together to prevent undesirable longitudinal movements from connector 600. Front tine 635 may securely engage with an inner surface of the main vessel when connector 600 is moved longitudinally in the direction of front wing 630. Similarly, rear tine 635 may securely engage with an inner surface of the main vessel when connector 600 is moved longitudinally in the direction of rear tine 645. Thus, the combination of front tine 635 and rear tine 645 may restrict connector 600 from longitudinal movements. In some examples, front tine 635 and rear tine 645 may be configured to securely engage the inner surface of the wall of the main vessel at two points along a centerline of the incision. In other examples, front tine 635 and rear tine 645 may be configured to engage in other locations surrounding the incision.

As shown here, barb 620 may be deployed from connector 600. In some examples, connector 600 may include additional barbs that, in conjunction with barb 620, may be configured to puncture a wall of a main vessel and couple with one or more slots in an incision seal. Additional barbs may assist in stabilizing the coupling of connector 600 with the incision seal by limiting the axial movements and lateral movements of connector 600. These additional barbs may be the same length or different length as barb 620. Here, connector 600 may include a pair of barbs facing away from each other. The pair of barbs may be configured to deploy together and lock with a pair of slots in the incision seal. In some examples, barb 620 may include an end fixed to connector base 603 and an unfixed end. The unfixed end of barb 620 may include a sharp end configured to puncture a wall of a main vessel and a protrusion configured to lock with a slot. To release the locking of the incision seal with connector 600, a surgeon may exert a force on the protrusion causing barb 620 to unlock with the slot. In other examples, the above-described elements may be implemented differently and are not limited to the examples shown and described.

Figure 7:
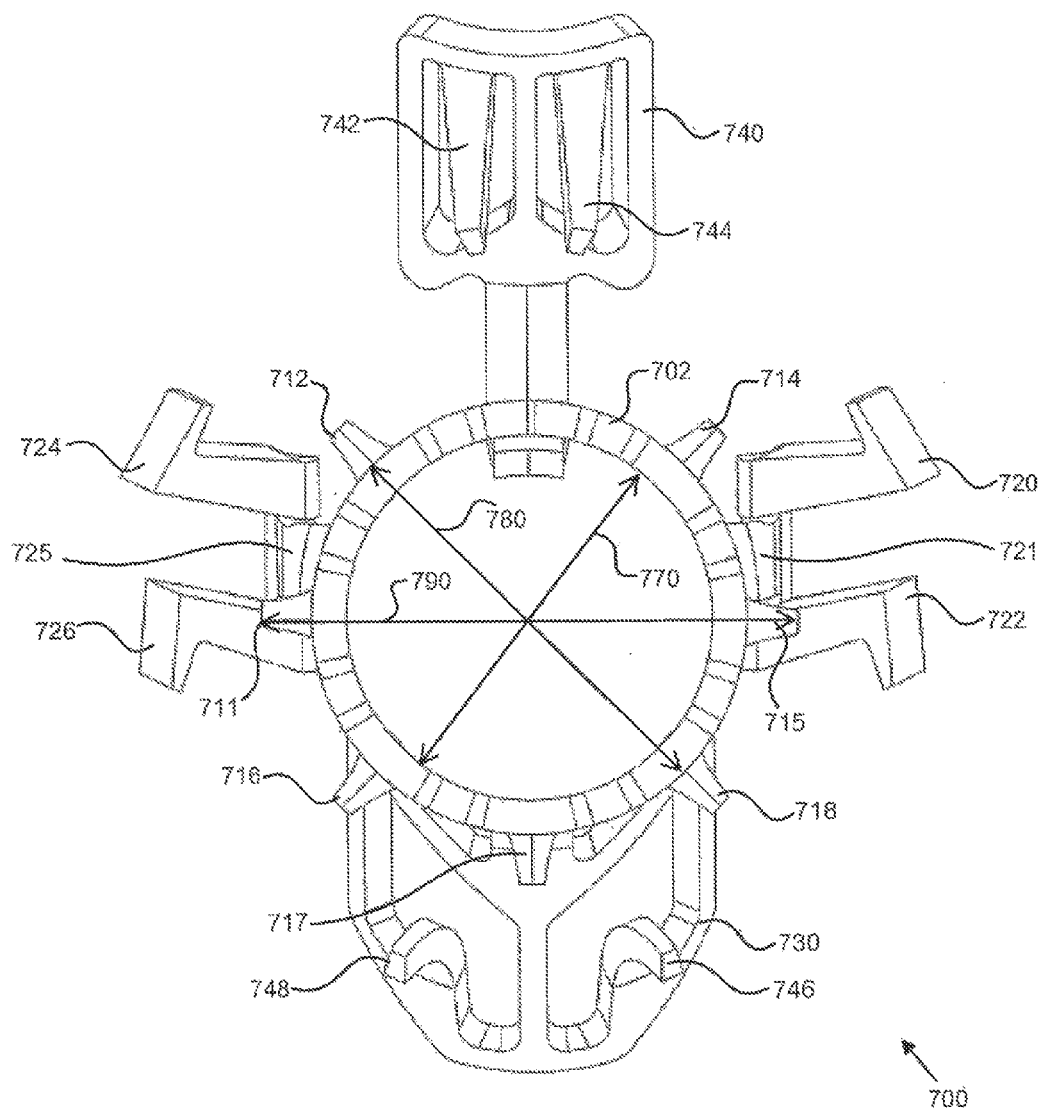
FIG. 7 illustrates a top view of an exemplary sutureless vascular anastomosis connector.

FIG. 7 illustrates a top view of an exemplary sutureless vascular anastomosis connector. In some examples, connector 700 may be made of a memory material that allows connector 700 to change shape. Here, connector 700 includes connector body 702, body tines 712, 714, 716, 717, and 718, barbs 720, 722, 724, and 726, side wings 721 and 725, front wing 730, rear wing 740, and wing tines 742, 744, 746, and 748. Connector body 702, body tines 712, 714, 716, 717, and 718, barbs 720, 722, 724, and 726, side wings 721 and 725, front wing 730, and rear wing 740 may be implemented similarly or substantially similar in function and structure to like-named elements as shown and described in FIG. 2, FIG. 3, FIG. 5, and FIG. 6. As shown here, body tines 712, 714, 716, 717, and 718, barbs 720, 722, 724, and 726, side wings 721 and 725, front wing 730, and rear wing 740 may be configured to deploy from connector 700.

As shown here, connector body 702 may include a tubular interior with inner diameter 770. Connector body 702 may be configured to transfer fluids, such as blood, between two ends of connector 700. For example, connector body may be configured to transfer blood between a graft vessel and a main vessel. In other examples, connector body 700 may have a differently shaped hollow center.

Connector body 702 may also have a tubular exterior with outer diameter 780. Outer diameter 780 may be configured to be substantially similar to the diameter of an inner surface of the graft vessel. In some examples, body tines 712, 714, 716, 717, and 718, when deployed, may be configured to extend from outer diameter 780 to tine diameter 790 and engage with the inner surface of the graft vessel. When engaged with the inner surface of the graft vessel, body tines 712, 714, 716, 717, and 718 may provide a restraining force that restricts the movement of the graft vessel. The restraining force may be configured based upon the orientation of body tines 712, 714, 716, 717, and 718. In some examples, the restrictions in movement may be direction-orientated, thus allowing the graft vessel to move in some directions but not in others. Here, body tines 712, 714, 716, 717, and 718 may be configured to have unfixed ends pointing towards the connector base, thus provide a restraining force that prevents axial movements of connector 700 but allows longitudinal movements of connector 700 towards the connector base. In another example, body tines 712, 714, 716, 717, and 718 may be positioned uniformly around connector body 702 to provide a consistent restraining force on the inner surface of the graft vessel. The consistent restraining force may be distributed evenly along the inner surface of the graft vessel, thus reducing the likelihood of tears caused by undue stress on the inner surface of the graft vessel. In other examples, the above-described elements may be implemented differently and are not limited to the examples shown and described.

Figure 8:
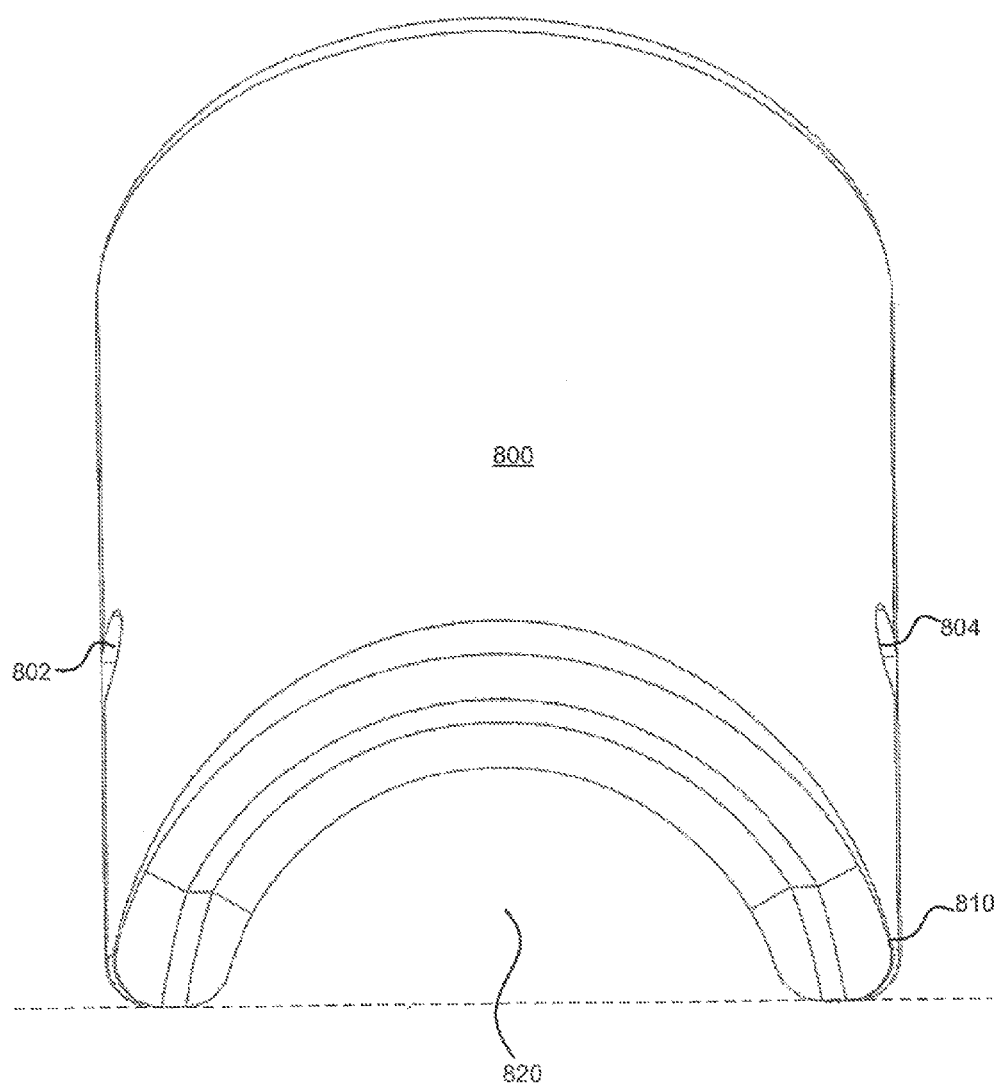
FIG. 8 illustrates a front view of an exemplary incision seal.

FIG. 8 illustrates a front view of an exemplary incision seal. Incision seal 800 may be configured to support the coupling between a graft vessel and a main vessel. As shown here, incision seal 800 includes latching ports 802 and 804, base 810, and recess 820. In some examples, latching ports 802 and 804 may be configured to receive barbs (not shown) from a connector (not shown) to which incision seal 800 is coupled, as described in greater detail below. As shown, recess 820 may be located along the length of base 810. In other examples, recess 820 may be shaped as a hollow channel, a tunnel, or other shaped opening. As an example, recess 820 may be configured to receive a portion of an upper wall of the main vessel. The portion of the upper wall of the main vessel may be protected or supported by incision seal 800 when the portion is received by recess 820. In an example, the recess may have a curvature that is substantially the same as the curvature of a portion of the upper outer wall of the main vessel. When incision seal 800 is placed on the portion of the upper outer wall of the main vessel, the recess may sit flush with the portion of the upper outer wall of the main vessel, thus covering up the portion of the upper outer wall of the main vessel. In some examples, recess 820 may sit flush against an incision in the upper outer wall of the main vessel. When recess 820 is placed flush against the incision, incision seal 800 may cover, protect, seal, or support the incision and the area surrounding the incision. Incision seal 800 may be made from synthetic materials such as plastics or other elastomeric materials. In other examples, the above-described elements and their design or function may be implemented differently and are not limited to the examples shown and described.

Figure 9:
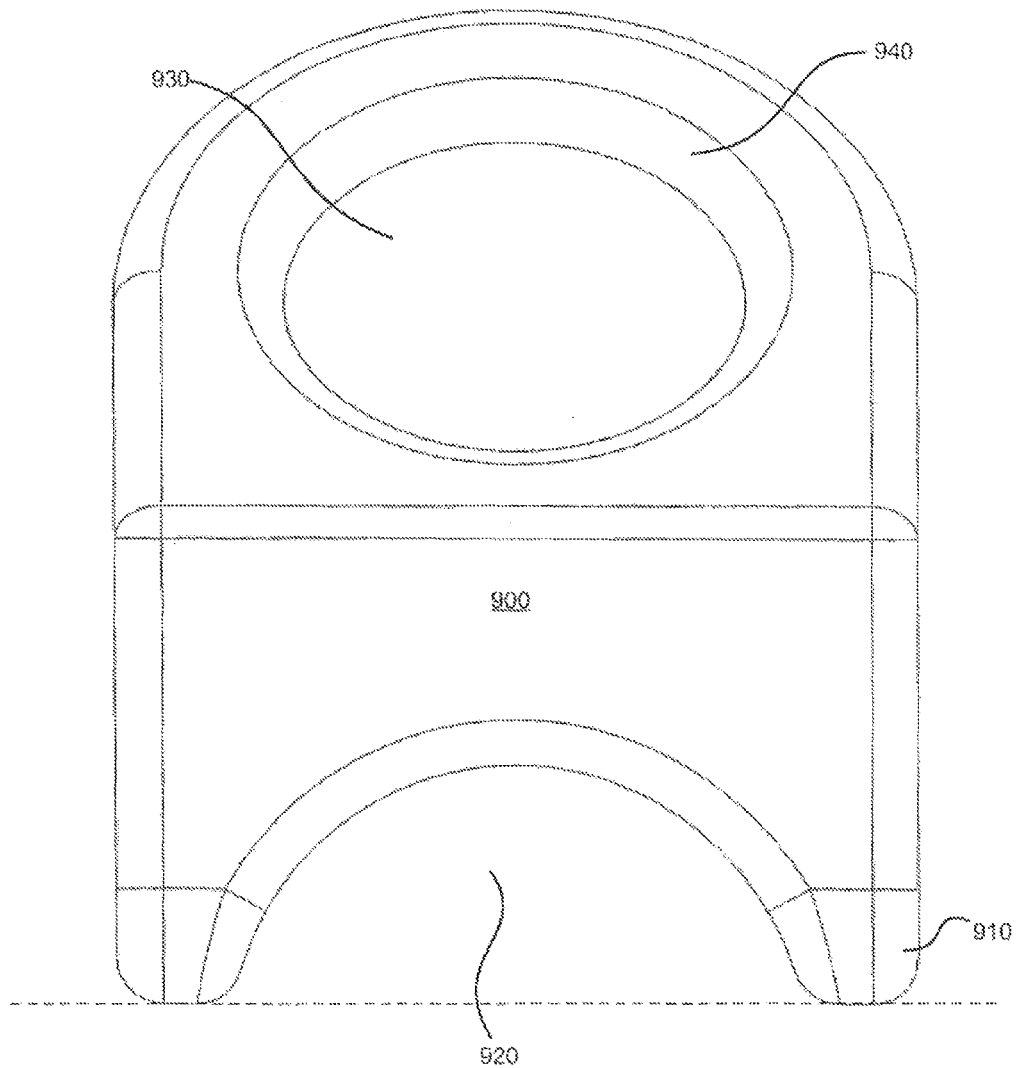
FIG. 9 illustrates a back view of an exemplary incision seal.

FIG. 9 illustrates a back view of an exemplary incision seal. Here, incision seal 900 may include base 910, recess 920, housing opening 930, and radius ring 940. In some examples, base 910 and recess 920 may be implemented similarly or substantially similar in function and structure to like-named elements as shown and described in FIG. 8. Housing opening 930 may be configured to receive a graft vessel. In some examples, the structure of housing opening 930 may be a receptacle, hollow channel, or other hollow channel that intersects incision seal 900. Housing opening 930 may provide a lumen for the graft vessel to be threaded through incision seal 900. In some examples, housing opening 930 may have a diameter. The diameter may be adjusted to accommodate graft vessels of various sizes. Alternatively, the diameter may be adjusted to change the fit of the graft vessel in housing opening 930. Here, housing opening 930 may be a hollow cylindrical structure with a diameter approximately equal to the outer surface of a graft vessel. The hollow cylindrical structure may provide a snug fit when the graft vessel is inserted into housing opening 930.

In some examples, housing opening 930 may intersect recess 920, thus coupling recess 920 with housing opening 930. This may provide a lumen for objects inserted into housing opening 930 to reach recess 920, or vice versa. Here, housing opening 930 and recess 920 may be configured to accommodate the junction of a graft vessel with a main vessel. For example, an incision of a main vessel may be covered by recess 920 while a graft vessel inserted into housing opening 930 may reach an incision in a main vessel. When a graft vessel is in contact with a main vessel, the two vessels may slowly graft together to form an integrated structure. Incision seal 900 may protect or support the junction between the graft vessel and the main vessel before the two vessels fully graft onto one another.

As shown here, housing opening 930 may further include radius ring 940 along an entrance of housing opening 930. Radius ring 940 may be configured to ease the insertion of a graft vessel into housing opening 930 by providing a larger aperture for insertion. In some examples, Radius ring 940 may have the same centerline as housing 930. In other examples, the above-described elements may be implemented differently and are not limited to the examples shown and described.

Figure 10:
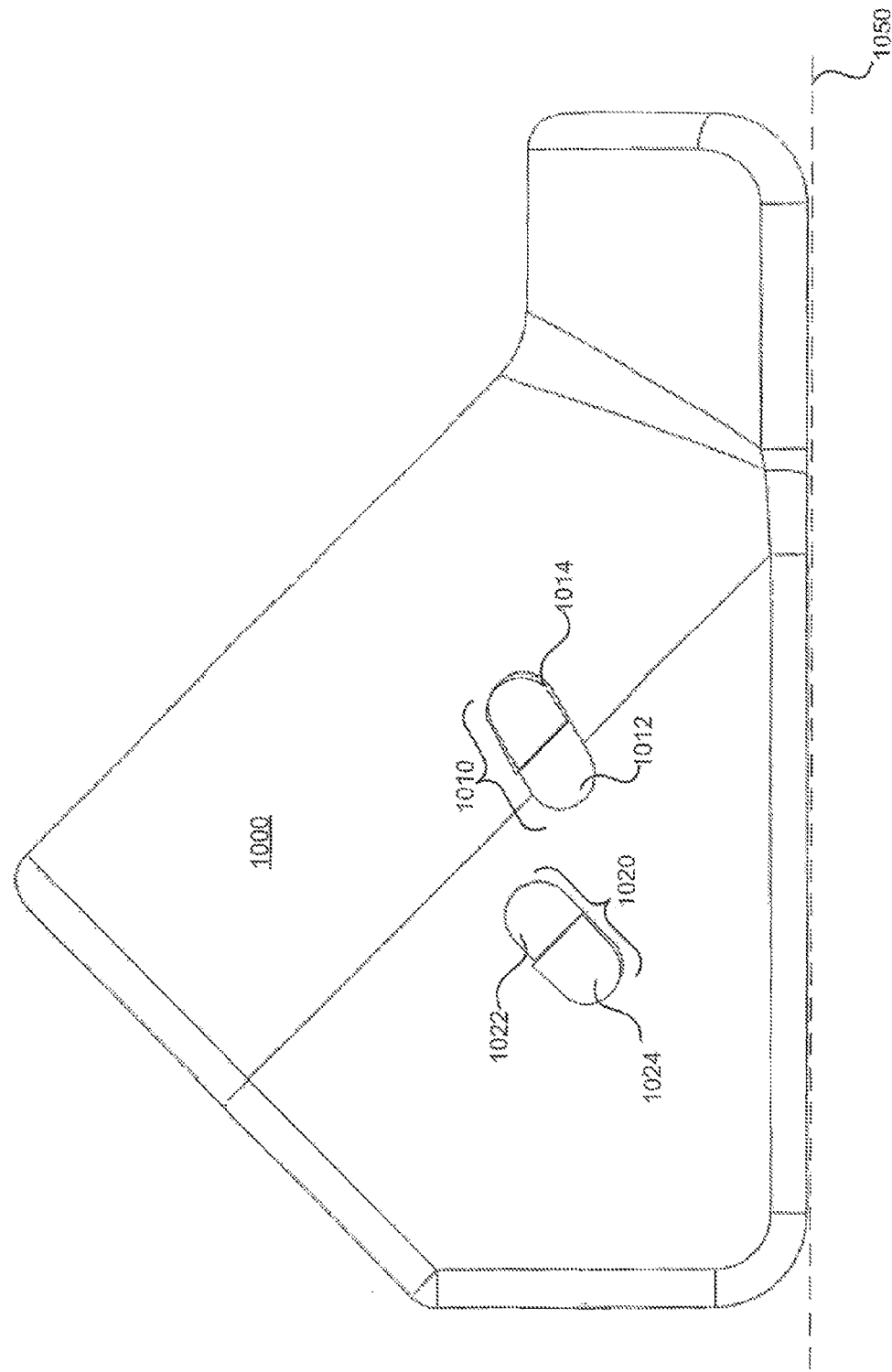
FIG. 10 illustrates a side view of an exemplary incision seal.

FIG. 10 illustrates a side view of an exemplary incision seal. Here, incision seal 1000 includes slots 1010 and 1020, latch pocket 1014 and 1024, ports 1012 and 1022, and base 1050. In some examples, base 1050 may be implemented similarly or substantially similar in function and structure to like-named elements as shown and described in FIG. 8 and FIG. 9. Slot 1010 and slot 1020 may be configured to engage a pair of barbs to secure a connector with incision seal 1000. As shown here, slot 1010 may include port 1012 and latch pocket 1014. Port 1012 may be configured to receive a barb (not shown). After the barb is received by port 1012, a barb may engage with latch pocket 1014, thus locking the barb in place. For example, a portion of a barb may be seated on latch pocket 1014, thus preventing the barb from retracting through port 1012. Once the barb is locked, incision seal 1000 may be securely coupled to the connector. As an example, a barb may automatically engage with latch pocket 1014 once the barb has been inserted into port 1012 by a pre-determined amount. To uncouple incision seal 1000 from the connector, a force may be applied to a barb to disengage the barb from latch pocket 1014 thus allowing the barb to retract through port 1012. Structurally, port 1012 and latch pocket 1014 may be a variety of shape's including square, rectangular, triangular, and semi-circular, to name a few. In some examples, slot 1020 may include port 1022 and latch pocket 1024. Port 1022 and latch pocket 1024 may be implemented similarly or substantially similar in function and structure as port 1012 and latch pocket 1014 as described above.

In some examples, the configuration of slots 1010 and 1020 in incision seal 1000 may vary depending on application. As an example, the number of slots used to securely couple incision seal 1000 with a connector (not shown) may vary. In general, incision seal 1000 may be more securely coupled with the connector when incision seal 1000 includes more slots. However, additional slots may increase the difficulty to unlock a connector from incision seal 1000. As another example, the orientation of slots 1010 or 1020 may also be varied. As shown here, slot 1010 and slot 1020 may be configured to have port 1012 and port 1022 closer to one another than latch pocket 1014 and latch pocket 1024. In other words, slot 1010 and slot 1020 may be oriented in different directions. In some examples, an independent force may be applied to unlock each slot. Thus, two forces applied in different directions may be used to unlock the connector from incision seal 1000 when slot 1010 and slot 1020 are oriented in different directions. For example, slot 1010 may require a force in the direction of latch pocket 1014 to port 1012 to unlock the barb from slot 1010. Similarly, slot 1020 may require a force in the direction of latch pocket 1024 to port 1022 to unlock the barb from slot 1020. These different forces may decrease the likelihood that the connector accidentally unlocks from incision seal 1000. In other examples, the above-described elements may be implemented differently and are not limited to the examples shown and described.

Figure 11:
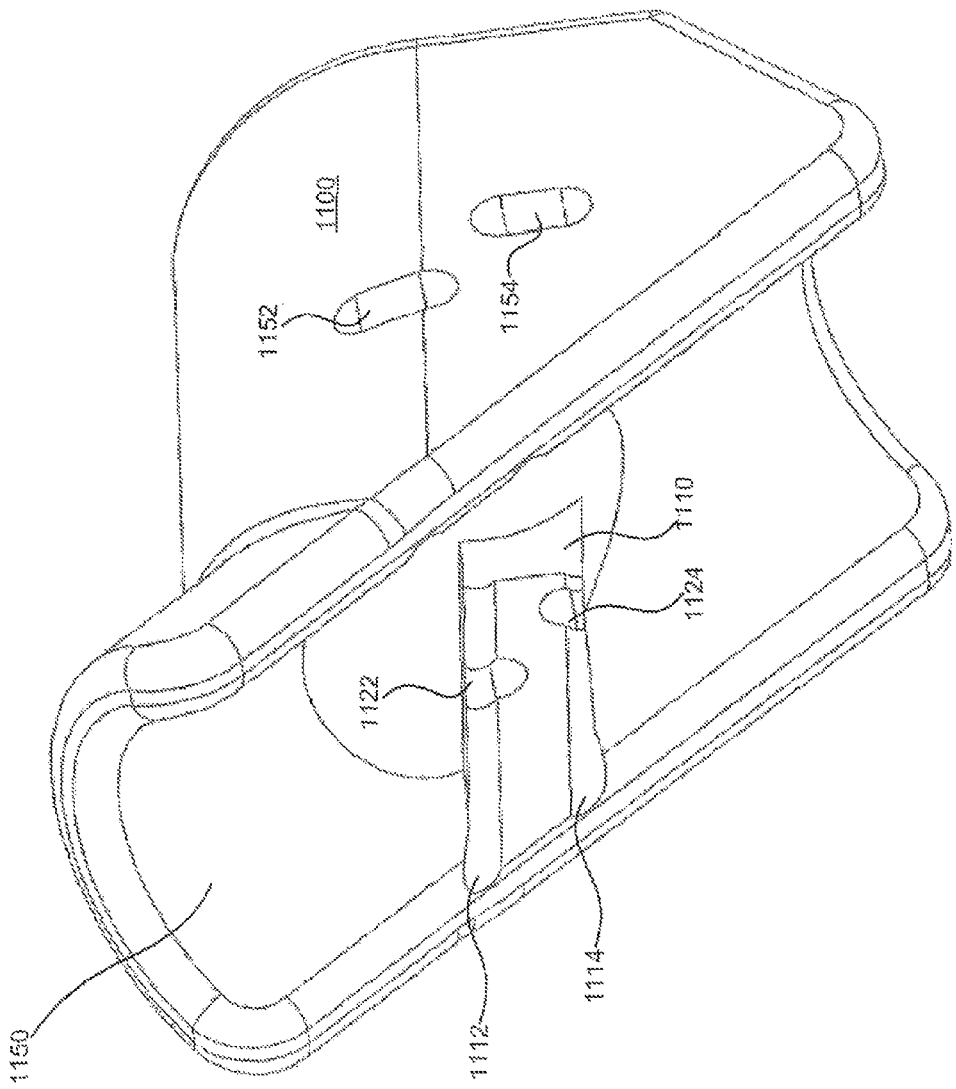
FIG. 11 illustrates a perspective view of an exemplary incision seal.

FIG. 11 illustrates a perspective view of an exemplary incision seal. As shown here, incision seal 1100 may include recess 1150, slots 1152 and 1154, groove 1110, guide 1112, guide 1114, slot 1122, and slot 1124. Recess 1150, slot 1122, and slot 1124 may be implemented similarly or substantially similar in function and structure to like-named elements as shown and described in FIG. 8 and FIG. 9, and FIG. 10. Groove 1110 may be configured to receive a connector (not shown). Once received, the connector may lock with incision seal 1100 using slot 1122 and slot 1124. In an example, the connector may be securely coupled with incision seal 1100 when barbs belonging to a connector are inserted into and locked with slot 1122 and slot 1124. In another example, a connector and incision seal 1100 may create a clamping force on a wall of a vessel when the connector is locked with the incision seal. This clamping force may securely couple the end of the graft vessel to an incision in the wall of a main vessel. Securely coupling the two vessels together may prevent fluids from leaking at the junction or provide support for the junction. Over time, the graft vessel and the main vessel may graft with one another, thus forming an integrated vessel. In some examples, groove 1110 may be formed by removing a portion of incision seal 1100 from recess 1150. In other examples, groove 1110 may be formed by removing a portion of incision seal 1100 from a lumen in incision seal 1110.

As shown here, incision seal 1100 may also include guide 1112 and guide 1114. Guide 1112 and guide 1114 may be configured to guide a barb, a part of a fastener, or other locking component from the connector to incision seal 1100. Structurally, guide 1112 and guide 1114 may be a trench, channel, or other cut-out along groove 1110. In an example, guide 1112 and guide 1114 may be parallel with one another and be disposed along two edges of groove 1110. In some examples, guide 1112 may intersect slot 1122. A barb or other locking component traveling along guide 1112 may enter slot 1122. In other words, guide 1112 may guide the barb, the part of a faster, or other locking component into slot 1122 where the two may mate or lock with one another. Similarly, guide 1114 may intersect slot 1124 and be configured to guide a barb or other locking component into slot 1124 where the two may mate or lock with one another. In other examples, the above-described elements may be implemented differently and are not limited to the examples shown and described.

FIGS. 12-31 illustrate exemplary processes for coupling a graft vessel to a main vessel. For example, the process shown in FIG. 12 to FIG. 31 may be used to perform a sutureless vascular anastomosis procedure using a connector, incision seal, and other elements as shown and described herein. In some examples, these processes may be performed in the order shown or any variation thereof. In other examples, other processes (not shown) may also be performed. In yet other examples, other processes for coupling a graft vessel to a main vessel may use some or all of the techniques illustrated in FIG. 12 to FIG. 31.

Figure 12:
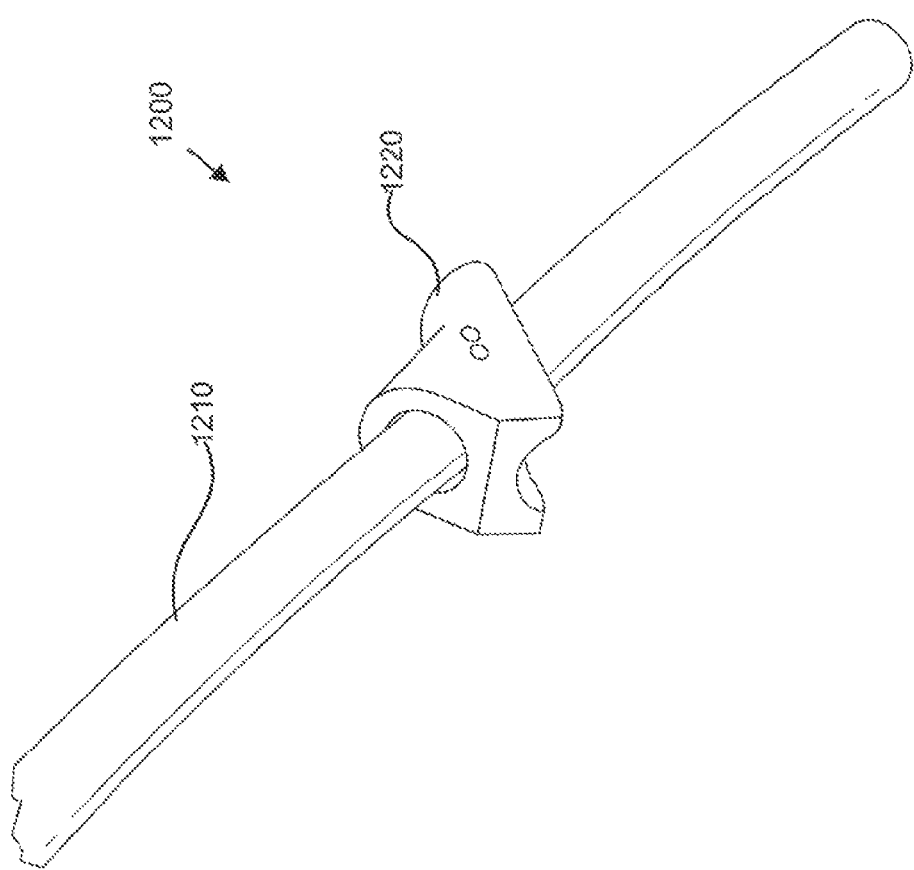
FIG. 12 illustrates an exemplary incision seal receiving a graft vessel.

FIG. 12 illustrates an exemplary incision seal receiving a graft vessel. Here, system 1200 may include graft vessel 1210 and incision seal 1220. In some examples, incision seal 1220 may be implemented similarly or substantially similar in function and structure as like-named objects shown in FIG. 8 to FIG. 11. A surgeon may insert and thread graft vessel 1210 through a housing in incision seal 1220. In an example, the housing may include a recessed ring. In some examples, graft vessel 1210 may be threaded through incision seal 1220 to keep incision seal 1220 away from the end of graft vessel 1210. This may allow the surgeon to operate on the end of graft vessel 1210 without interference from incision seal 1220. In other examples, the above-described elements may be implemented differently and are not limited to the examples shown and described.

Figure 13:
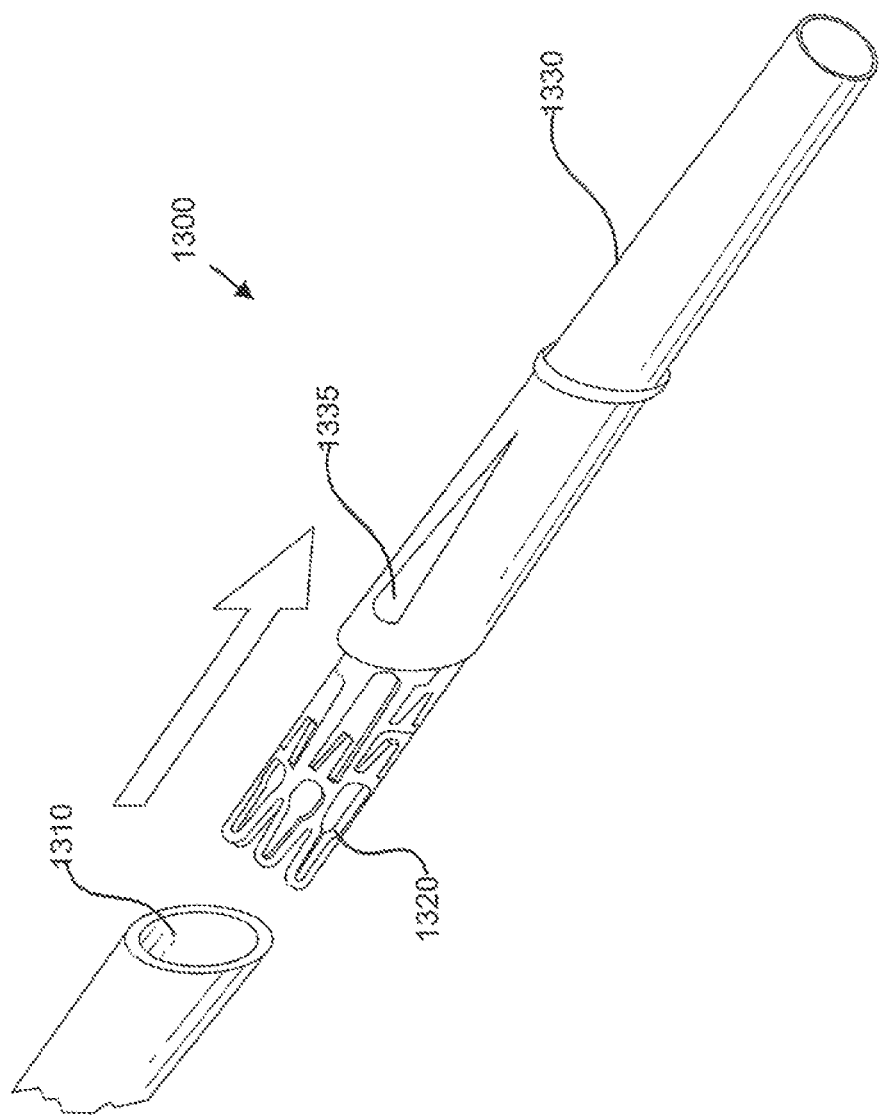
FIG. 13 illustrates an end of a graft vessel receiving a sutureless vascular anastomosis connector.

FIG. 13 illustrates an end of a graft vessel receiving an exemplary sutureless vascular anastomosis connector. Here, system 1300 may include graft vessel end 1310, connector 1320, and sheath 1330. Connector 1320 may be implemented similarly or substantially similar in function and structure as like-named objects shown in FIG. 2 to FIG. 7. Connector 1320 may be partially covered by sheath 1330. As an example, sheath 1330 may provide a restraining force on a connector base of connector 1320 to prevent wings or barbs of the connector base from deploying. In another example, sheath 1330 may provide a surface for a surgeon to grasp when handling connector 1320. The surgeon may hold connector 1320 by sheath 1330 while inserting connector 1320 into graft vessel end 1310. In some examples, the tip of connector 1320 may be contractible to ease the task of inserting connector 1320 into graft vessel end 1310. In other examples, connector 1320 may be securely coupled to graft vessel end 1310 when inserted. For example, the body of connector 1320 may include retention spikes (i.e. tines) to securely engage the inner wall of the graft vessel. Once the retention spikes are engaged, connector 1320 may be securely coupled to graft vessel end 1310.

As shown here, sheath 1330 may include orientation guide 1335. Orientation guide 1335 may be configured to guide the insertion of connector 1320 into graft vessel end 1310 in the direction of the arrow shown. In some examples, graft vessel end 1310 and sheath 1330 may both contain an angular end. For example, graft vessel end 1310 and sheath 1330 may both contain an end at, for example, a 45-degree angle. In other examples, the degree of orientation may be varied and is not limited to 45 degrees. Orientation guide 1335 may help ensure that the angular end of graft vessel end 1310 aligns with the angular end of sheath 1330 by placing a point of reference along the exterior of sheath 1330. This point of reference may assist a surgeon in orienting connector 1310 during the insertion of connector 1320 into graft vessel end 1310. Properly inserting connector 1320 into graft vessel end 1310 may ensure that connector 1320 may be successfully deployed later on. In other examples, the above-described elements may be implemented differently and are not limited to the examples shown and described.

Figure 14:
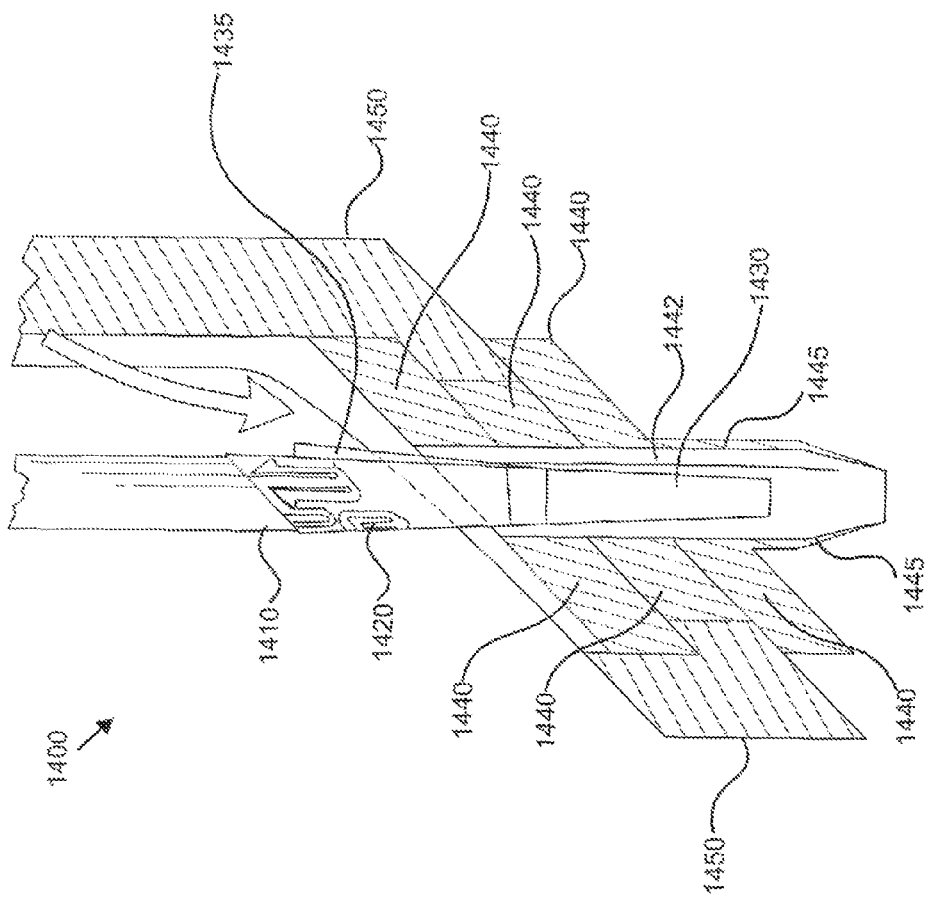
FIG. 14 illustrates a side and cross-sectional view of loading an exemplary sutureless vascular anastomosis connector into an exemplary introducer.

FIG. 14 illustrates a side and cross-sectional view of loading an exemplary sutureless vascular anastomosis connector into an introducer. Here, system 1400 includes graft vessel 1410, connector 1420, sheath 1430, orientation guide 1435, introducer 1440, and tool 1450. Connector 1420 and sheath 1430 may be implemented similarly or substantially similar in function and structure as like-named objects shown in FIG. 2 to FIG. 7 and FIG. 13. Connector 1420 may be disposed within and securely coupled with graft vessel 1410 and sheath 1430. Moving one of these coupled elements may result in similar movements from the other coupled elements. Introducer 1440 may be configured to receive connector 1420 and insert connector 1420 into a main vessel. As shown here, introducer 1440 may include lumen 1442 configured to receive graft vessel 1410, connector 1420, sheath 1430, or other object. Introducer 1440 may also include tip 1445 disposed on one end of lumen 1442. Tip 1445 may have an end that includes one or more slits configured to remain closed when in a resting state and open when a force is applied.

Here, sheath 1430 may be loaded into introducer 1440. This may include inserting sheath 1430 into an opening of introducer 1440, such as lumen 1442. In some examples, sheath 1430 may include orientation guide 1435. Orientation guide 1435 may be configured to orient sheath 1430 before insertion into lumen 1442. By orienting sheath 1430, connector 1420 may also be oriented since sheath 1430 is coupled to connector 1420. Thus, connector 1420 may also be oriented before insertion into lumen 1442. As an example, orientation guide 1435 may be aligned with an index key of introducer 1440 (not shown). When orientation guide 1435 is inserted into the index key, sheath 1430 or connector 1420 may be successfully oriented with respect to introducer 1440. In other examples, the above-described elements may be implemented differently and are not limited to the examples shown and described.

Figure 15:
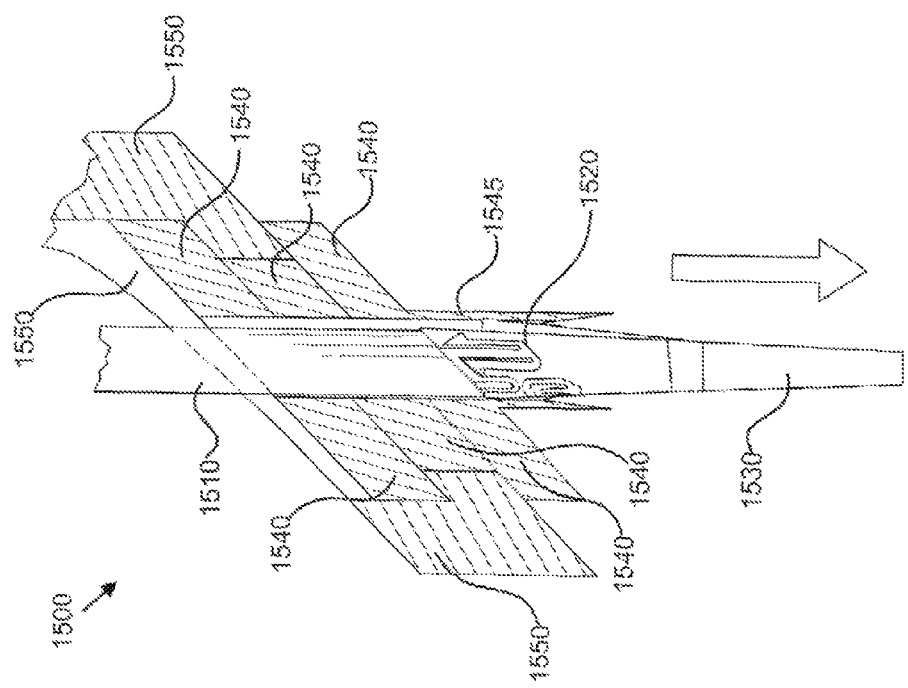
FIG. 15 illustrates another side and cross-sectional view of loading an exemplary sutureless vascular anastomosis connector into an exemplary introducer.

FIG. 15 illustrates another side and cross-sectional view of loading an exemplary sutureless vascular anastomosis connector into an exemplary introducer. Here, system 1500 includes graft vessel 1510, connector 1520, sheath 1530, introducer 1540, tip 1545, and tool 1550. Connector 1520, sheath 1530, introducer 1540, and tip 1545 may be implemented similarly or substantially similar in function and structure as like-named elements shown in FIG. 2 to FIG. 7 and FIG. 13 to FIG. 14. Connector 1520 may be disposed within and securely coupled with graft vessel 1510 and sheath 1530. Thus, moving one of these coupled elements may result in similar movements from the other coupled elements. As an example, connector 1520 may be securely coupled to graft vessel 1510 by retention spikes (i.e. tines) of connector 1520. In another example, connector 1520 may be securely coupled to sheath 1530 by a restrictive force created from wedging connector 1520 and sheath 1530 through introducer 1540.

As shown here, a force may be applied to sheath 1530 to insert sheath 1530 into an opening of introducer 1540. In some examples, sheath 1530 may enter the opening, pass through a lumen of introducer 1540, and exit an end of tip 1545. As sheath 1530 is inserted into introducer 1540, sheath 1530 may remain securely coupled to connector 1520. As an example, connector 1520 may have retention spikes (i.e. tines) that securely contact the inner surface of sheath 1530 due to a restraining force provided by the wall of the lumen. When sheath 1530 contacts the end of tip 1545, the applied force may cause tip 1545 to open and accommodate sleeve 1530. This may leave an exposed portion of sleeve 1530 outside the end of tip 1545. As sheath 1530 is further inserted into the opening of introducer 1540, tip 1545 may expand or retract to accommodate the outer surface of sleeve 1530 while the exposed portion of sleeve 1530 may increase. In some examples, the exposed portion may be grasped and pulled. Pulling sheath 1530 may result in the coupled connector 1520 and graft vessel 1510 to also be pulled towards tip 1545. When sheath 1530 exits the end of introducer 1540, connector 1520 and grafting vessel 1510 may be properly seated in introducer 1540. In other examples, the above-described elements may be implemented differently and are not limited to the examples shown and described.

Figure 16:
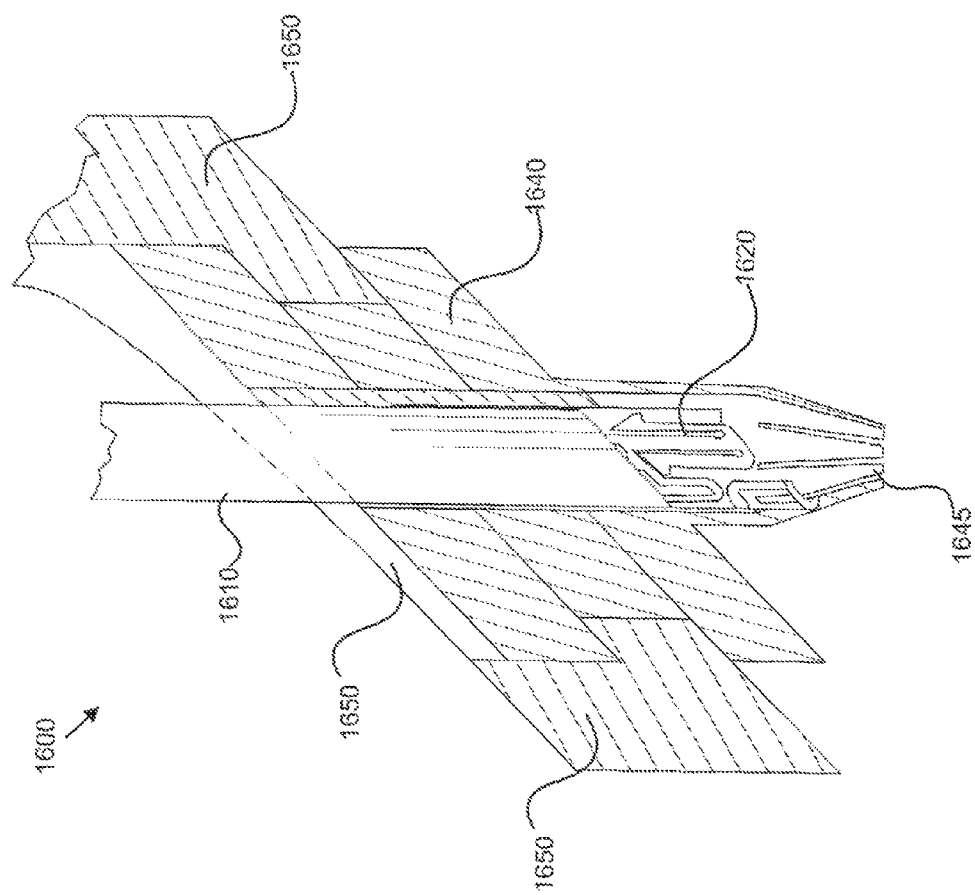
FIG. 16 illustrates a further side and cross-sectional view of exemplary sutureless vascular anastomosis connector loaded into an exemplary introducer.

FIG. 16 illustrates a further side and cross-sectional view of exemplary sutureless vascular anastomosis connector loaded into an exemplary introducer. Here, system 1600 includes graft vessel 1610, connector 1620, introducer 1640, tip 1645, and tool 1650. Connector 1620, introducer 1640, and tip 1645 may be implemented similarly or substantially similar in function and structure as like-named objects shown and described in FIG. 2 to FIG. 7 and FIG. 13 to FIG. 15. As shown here, graft vessel 1610 may be disposed within introducer 1640 so that an angled end of graft vessel 1610 may be parallel with an exterior surface of introducer 1640. Moreover, connector 1620 may be disposed within introducer 1640 and reside within tip 1645. Tip 1645 may be configured to shield connector 1620 during insertion into the main vessel. Using tool 1650, tip 1645 may be used to prevent retention spikes (i.e. tines), barbs, or other elements of connector 1620 from improperly engaging the main vessel during insertion. In other examples, the above-described elements may be implemented differently and are not limited to the examples shown and described.

Figure 17:
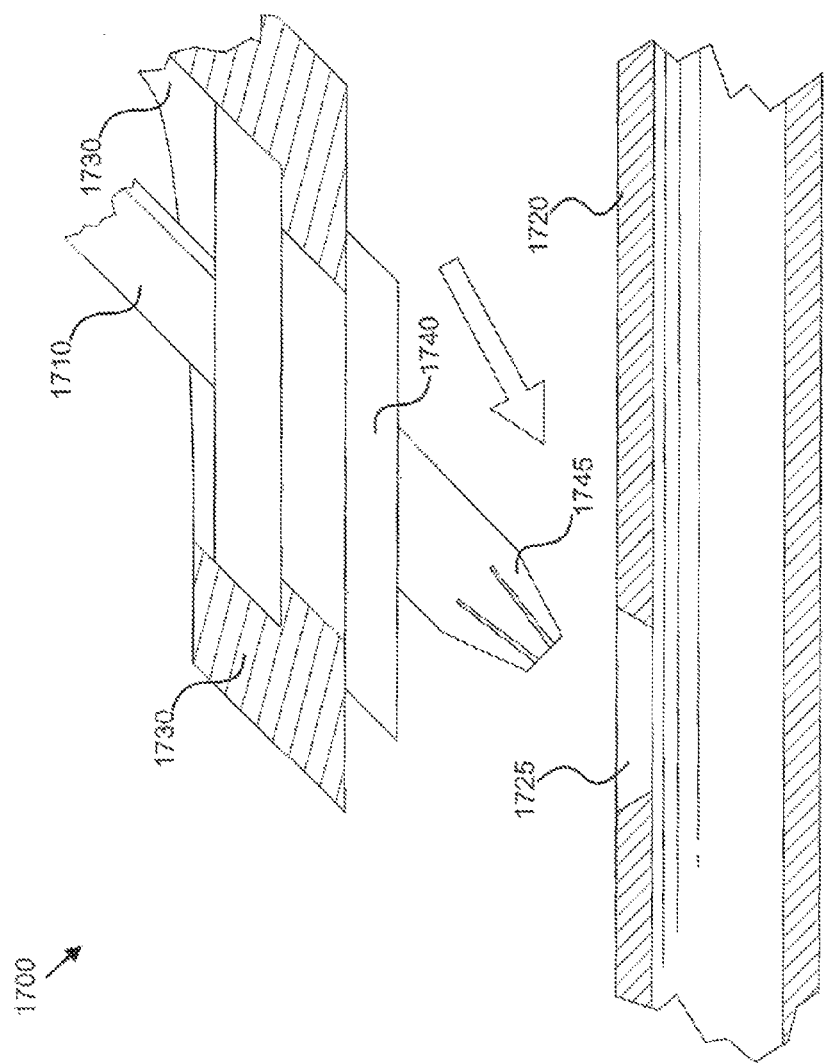
FIG. 17 illustrates a side and cross-sectional view of an exemplary introducer entering an incision in a main vessel.

FIG. 17 illustrates a side and cross-sectional view of an exemplary introducer entering an incision in a main vessel. Here, system 1700 may include graft vessel 1710, main vessel 1720, incision 1725, tool 1730, introducer 1740, and tip 1745. In some examples, introducer 1740 and tip 1745 may be implemented similarly or substantially similar in function and structure as like-named objects shown and described in FIG. 13 to FIG. 16. Graft vessel 1710 may be securely coupled to a connector (not shown). The connector may be configured to be inserted and securely coupled to a main vessel to join the main vessel with graft vessel 1710. Thus, the connector may serve as the coupling component to couple graft vessel 1710 with main vessel 1720. Here, introducer 1740 may be configured to insert the connector into the main vessel. Introducer 1740, while housing graft vessel 1710 and the connector, may be inserted into incision 1725 at an angle. As an example, tip 1745 of introducer 1740 may be inserted into incision 1725. In other examples, the above-described elements may be implemented differently and are not limited to the examples shown and described.

Figure 18:
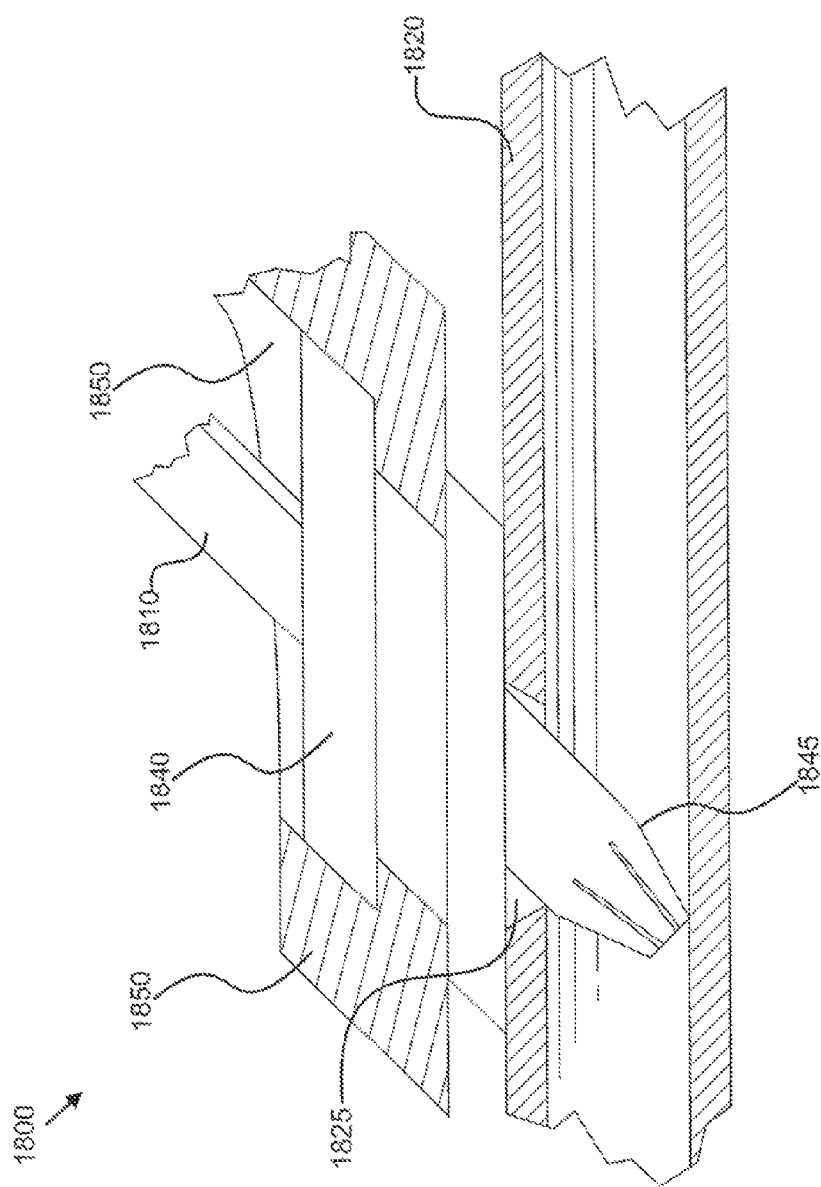
FIG. 18 illustrates a side and cross-sectional view of an exemplary introducer disposed within an incision in a main vessel.

FIG. 18 illustrates a side and cross-sectional view of an exemplary introducer disposed within an incision in a main vessel. As shown here, system 1800 may include graft vessel 1810, main vessel 1820, incision 1825, introducer 1840, and tip 1845. Introducer 1840 and tip 1845 may be implemented similarly or substantially similar in function and structure as like-named objects shown and described in FIG. 13 to FIG. 17. An end of graft vessel 1810 may be securely coupled to a connector (not shown), where the end of graft vessel 1810 and the connector are both housed within introducer 1840. Here, introducer 1840 may be inserted into incision 1825 of main vessel 1820. As an example, tip 1845 of inserter 1840 may be disposed within main vessel 1820 when introducer 1840 is inserted. This may cause a surface of inserted introducer 1840 to abut a portion of the wall of main vessel 1820 surrounding incision 1825. In some examples, a diameter of tip 1845 may be approximately the same as a diameter of graft vessel 1810. In other examples, the above-described elements may be implemented differently and are not limited to the examples shown and described.

Figure 19:
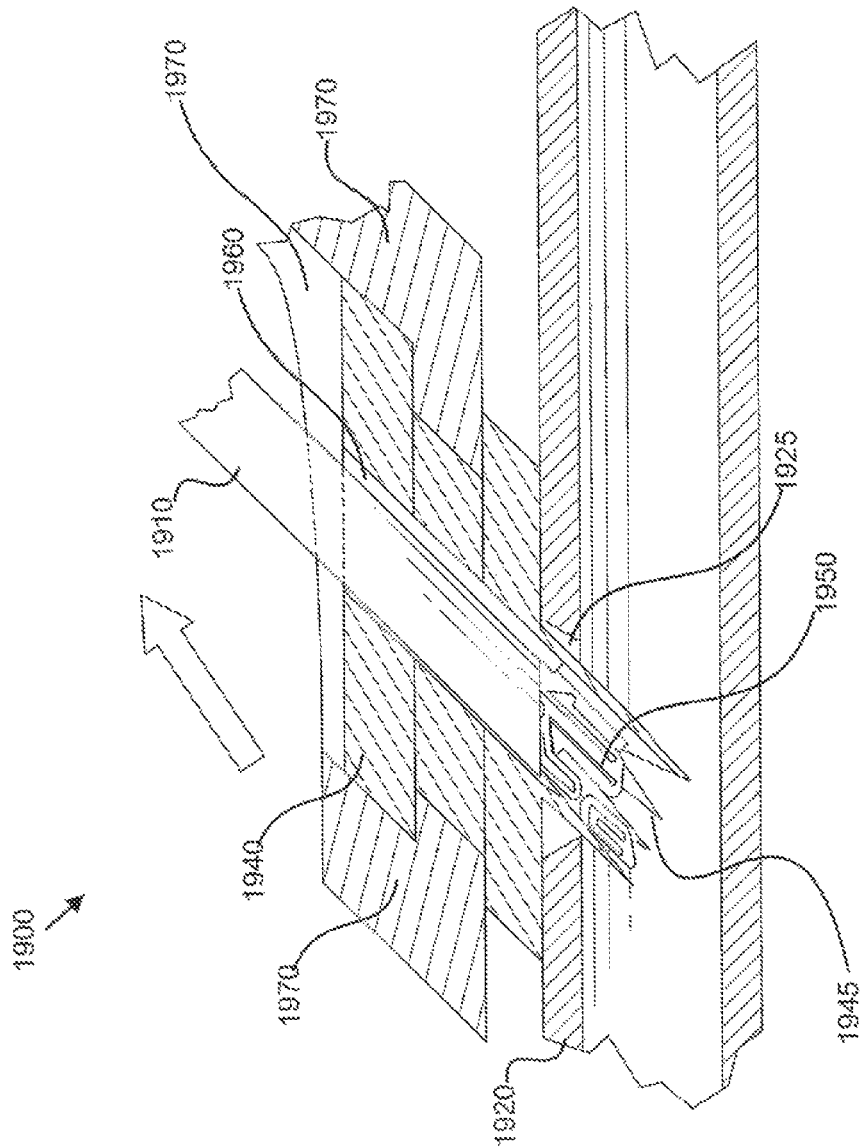
FIG. 19 illustrates a side and cross-sectional view of an exemplary introducer inserting a connector inside a main vessel.

FIG. 19 illustrates a side and cross-sectional view of an exemplary introducer inserting an exemplary sutureless vascular anastomosis connector inside a main vessel. As shown here, system 1900 may include graft vessel 1910, main vessel 1920, incision 1925, introducer 1940, tip 1945, connector 1950, deployment rod 1960, and tool 1970. Introducer 1940, tip 1945, and connector 1950 may be implemented similarly or substantially similar in function and structure as like-named objects shown and described in FIG. 2 to FIG. 7 and FIG. 13 to FIG. 18. Introducer 1940 may be configured to insert or introduce connector 1950 into main vessel 1920. For example, tip 1945 of introducer 1940 may be inserted into incision 1925 and a surface of introducer 1940 may overlap an exterior surface surrounding incision 1925. In other words, introducer 1940 may be positioned so that tip 1945 is inserted into incision 1925 of main vessel 1920 and a surface of introducer 1940 is aligned with or flush against a wall of main vessel 1920. Introducer 1940 may remain in this position during the insertion or introduction of connector 1950 into main vessel 1920.

In some examples, connector 1950 and graft vessel 1910 may be pushed through introducer 1940. As an example, rod 1960 may serve as an insertion instrument configured to contact connector 1950 to push connector 1950 towards tip 1945. In an example, connector 1950 may be pushed through introducer 1940, extend out of tip 1945, and enter into main vessel 1920. As connector 1950 extends out of tip 1945, tip 1945 may expand to accommodate connector 1950. In some examples, connector 1950 may be inserted into main vessel 1920 while introducer 1940 remains flush against a wall of main vessel 1920 with tip 1945 inserted into main vessel 1920. In other examples, the above-described elements may be implemented differently and are not limited to the examples shown and described.

Figure 20:
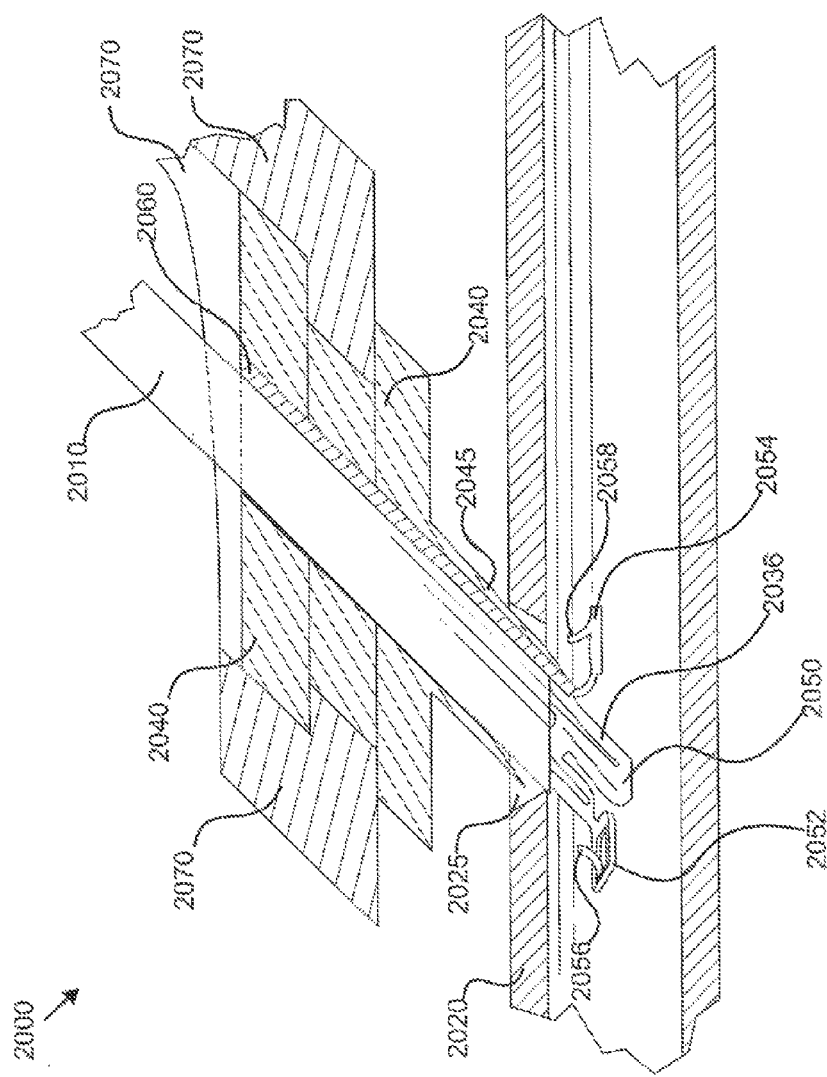
FIG. 20 illustrates a side and cross-sectional view of an exemplary introducer deploying a connector in a main vessel.

FIG. 20 illustrates a side and cross-sectional view of an exemplary introducer deploying an exemplary sutureless vascular anastomosis connector in a main vessel. As shown here, system 2000 may include graft vessel 2010, main vessel 2020, incision 2025, introducer 2040, tip 2045, connector 2050, front wing 2052, rear wing 2054, barb 2036, and tool 2070. Introducer 2040, tip 2045, and connector 2050, front wing 2052, rear wing 2054, and barb 2036 may be implemented similarly or substantially similar in function and structure as like-named objects shown and described in FIG. 2 to FIG. 7 and FIG. 13 to FIG. 19. Introducer 2040 may be configured to insert or introduce connector 2050 in main vessel 2020. In some examples, this may be a two step process. In a first step, tip 2045 may be inserted within main vessel 2020 with connector 2050 located within tip 2045. In a second step, tip 2045 may be retracted from main vessel 2020 while leaving connector 2050 within main vessel 2020.

As shown here, rod 2060 may be configured to control the position of connector 2050. In some examples, a pushing force may be applied to rod 2060 to change the position of connector 2050 with respect to main vessel 2020. For example, the pushing force may cause rod 2060 to contact and push connector 2050 further into main vessel 2020. The contact point may be a wing, a tine, a barb, or other slight protrusion along the exterior surface of connector 2050. In other examples, a maintaining force may be applied to rod 2060 to maintain the position of connector 2050 in main vessel 2020. For example, the maintaining force may be applied to rod 2060 to maintain the position of connector 2050 while a lifting force may be applied to introducer 2040 to remove introducer 2040 away from main vessel 2020. When the lifting force is applied, introducer 2040 and tip 2045 may travel along the shaft of graft vessel 2010 away from main vessel 2020. This may cause tip 2045 to expand or reduce to accommodate the exterior surface of connector 2050 and graft vessel 2010. For example, tip 2045 may expand to approximately the same circumference as graft vessel 2010. As tip 2045 is retracted from main vessel 2020, connector 2050 may be exposed from an end of tip 2045 and remain within main vessel 2020. Eventually, connector 2050 may be entirely exposed from tip 2045 and disposed inside main vessel 2020.

In some examples, tip 2045 may apply a restraining force on connector 2050. The restraining force may prevent front wing 2052, rear wing 2054, and barb 2036 from deploying while connector 2050 is disposed within tip 2045. As tip 2045 is removed from main vessel 2020, a portion of connector 2050 may become exposed from an end of tip 2045. The exposed portion may be relieved from the restraining force. Thus, front wing 2052, rear wing 2054, and barb 2036 may deploy from connector 2050 once they belong to the exposed portion. Once deployed, these elements may securely engage with an interior surface of main vessel 2020. In other examples, the above-described elements may be implemented differently and are not limited to the examples shown and described.

Figure 21:
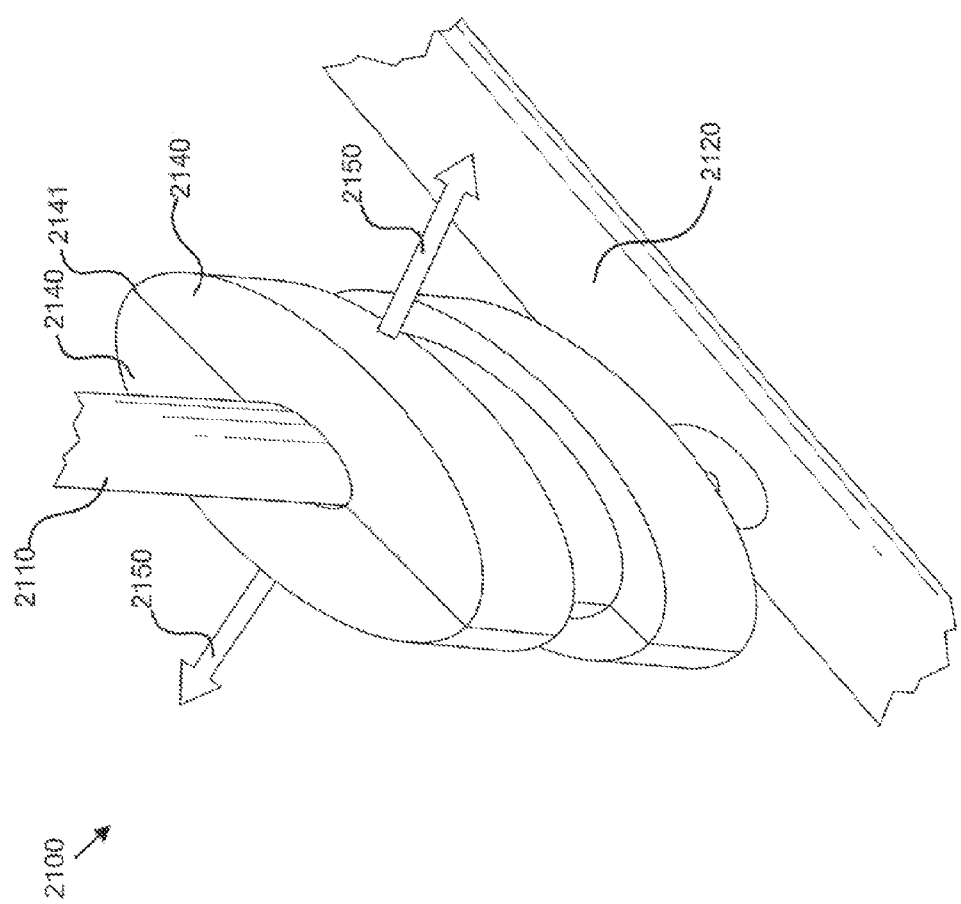
FIG. 21 illustrates an exemplary introducer encompassing a graft vessel.

FIG. 21 illustrates an exemplary introducer encompassing a graft vessel. As shown here, system 2100 may include graft vessel 2110, main vessel 2120, introducer 2140, and slit 2141. Introducer 2140 may be implemented similarly or substantially similar in function and structure as like-named objects shown and described in FIG. 14 to FIG. 20. A by-product of coupling an end of graft vessel 2110 with a side of main vessel 2120 may be introducer 2140 encompassing graft vessel 2110. It may be desirable to remove introducer 2140 from graft vessel 2110 so that an incision seal may be lowered onto main vessel 2120 and used to seal the coupling of graft vessel 2110 with main vessel 2120.

Introducer 2140 may include slit 2141. Slit 2141 may be configured to remove introducer 2140 from graft vessel 2110 by splitting introducer 2140 into multiple parts. In other words, slit 2141 may provide a means for splitting and removing introducer 2140 from graft vessel 2120. Here, slit 2141 may be disposed on a plane that bisects introducer 2140 into two equal parts. When a detaching force is applied to introducer 2140, introducer 2140 may split into two equal parts along slit 2141. In other examples, multiple slits may be disposed along multiple planes of introducer 2140. These multiple slits may divide introducer 2140 into multiple parts when a detaching force is applied. In yet other examples, the above-described elements may be implemented differently and are not limited to the examples shown and described.

Figure 22:
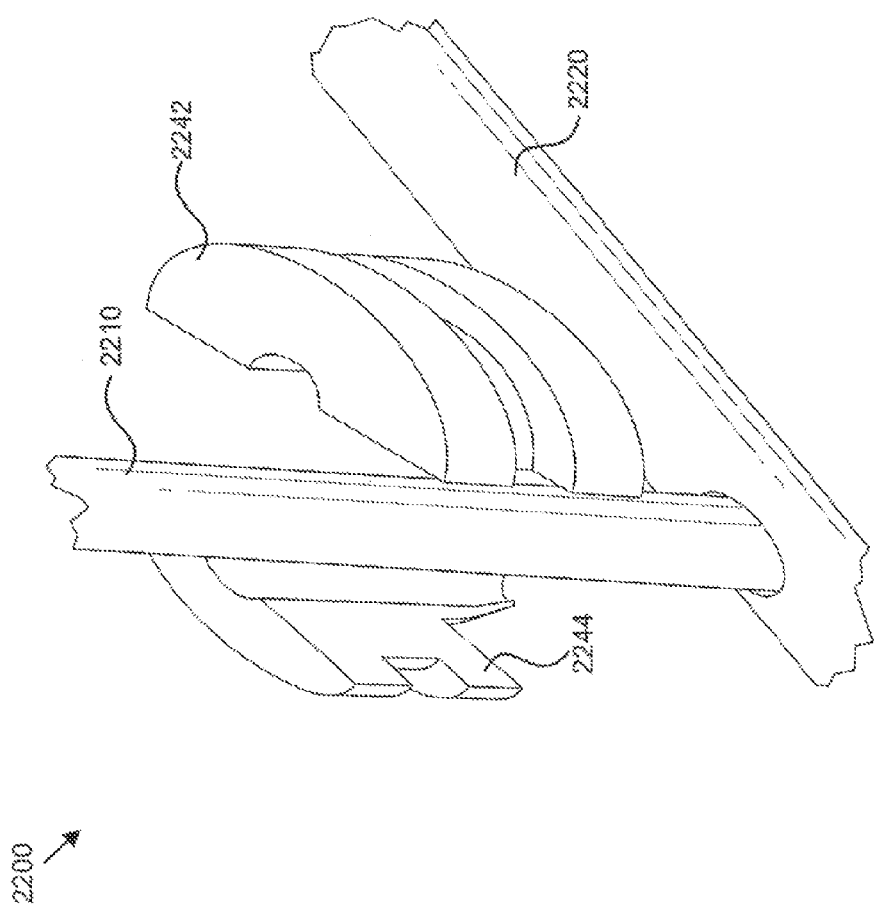
FIG. 22 illustrates an exemplary introducer detaching from a graft vessel.

FIG. 22 illustrates an exemplary introducer detaching from a graft vessel. As shown here, system 2200 may include graft vessel 2210, main vessel 2220, introducer part 2242 and introducer part 2244. Initially, an introducer may be encompassing graft vessel 2210. After a detaching force is applied, the introducer may split along a plane intersecting the introducer to form introducer part 2242 and introducer part 2244. Once split, introduce part 2242 and introducer part 2244 may no longer encompass graft vessel 2210 and thus, may be removed system 2200. In other examples, the above-described elements may be implemented differently and are not limited to the examples shown and described.

Figure 23:
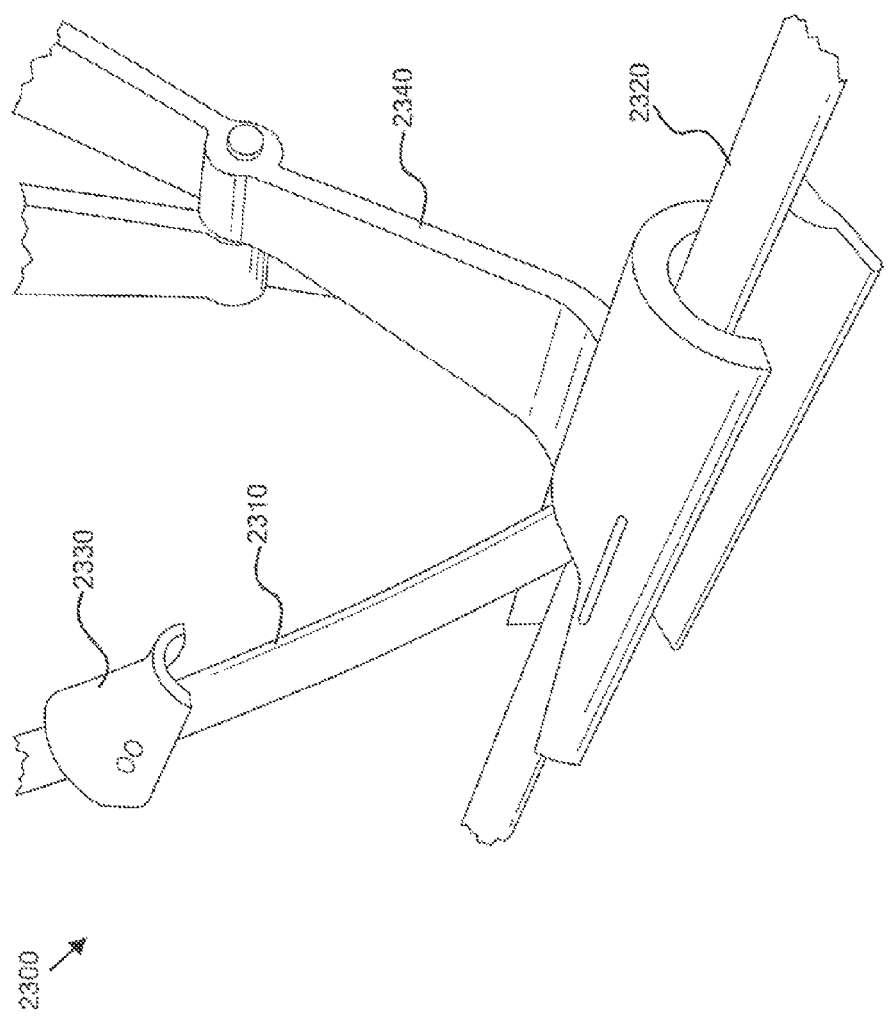
FIG. 23 illustrates an exemplary barb-setting device.

FIG. 23 illustrates an exemplary barb-setting device. Here, system 2300 may include graft vessel 2310, main vessel 2320, incision seal 2330, and barb-setting device 2340. In some examples, barb-setting device 2340 may also be referred to as a "tool." As shown, incision seal 2330 may be implemented similarly or substantially similar in function and structure as like-named objects shown and described in FIG. 8 to FIG. 11. As shown here, barb-setting device 2340 may be in an open position. Barb-setting device 2340 may be configured to cause one or more barbs belonging to a connector within main vessel 2320 to puncture a wall of the main vessel. The punctured barbs may subsequently lock with incision seal 2330. Structurally, barb-setting device 2340 may include two components hinged together in a similar fashion as a traditional pair of pliers. The first component may include an end having a semi-cylindrical structure configured to longitudinally receive main vessel 2320. In an example, the semi-cylindrical structure may further include one or more openings configured to accommodate one or more barbs. In another example, the semi-cylindrical structure may be slotted on one end to receive graft vessel 2310. The slot may allow the junction between graft vessel 2310 and main vessel 2320 to be disposed in the middle of the semi-cylindrical structure. This may result in more uniform distribution of force on graft vessel 2310 and main vessel 2320 when a clenching force is applied to barb-setting device 2340. The second component of barb-setting device 2340 may also be configured to longitudinally receive main vessel 2320. Together, the first component and second component may clench main vessel 2320 thus causing one or more barbs to pierce the main vessel. In some examples, barb-setting device 2340 may also securely engage wings or tines of the connector with an inner surface of the main vessel. In other examples, the above-described elements may be implemented differently and are not limited to the examples shown and described.

Figure 24:
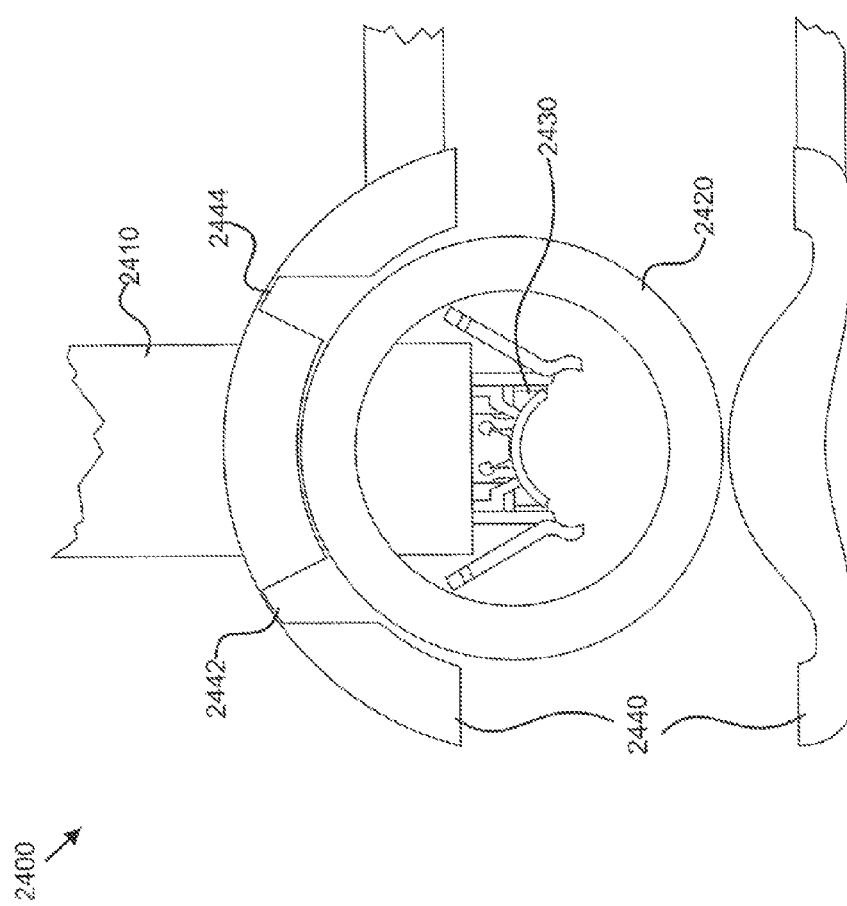
FIG. 24 illustrates a cross-sectional view of an exemplary barb-setting device.

FIG. 24 illustrates a cross-sectional view of an exemplary barb-setting device. Here, system 2400 may include graft vessel 2410, main vessel 2420, connector 2430, barb-setting device 2440, opening 2442 and opening 2444. In some examples, connector 2430 and barb-setting device 2440 may be implemented similarly or substantially similar in function and structure as like-named objects shown and described in FIG. 2 to FIG. 7, FIG. 13 to FIG. 16, FIG. 19 to FIG. 20, and FIG. 23. As shown here, barb-setting device 2440 may be in an open position. Barb-setting device 2440 may be configured to cradle the junction between graft vessel 2410 and main vessel 2420. Connector 2430 may be disposed within main vessel 2420 and securely coupled to graft vessel 2410. In some examples, barb-setting device 2440 may be configured to apply a clenching force on the exterior surface of main vessel 2420 that causes barbs, wings, or retention spikes (i.e. tines) of connector 2430 to engage with an inner surface of main vessel 2420. For example, an upper portion of barb-setting device 2440 may be configured to receive an upper wall of main vessel 2420. The upper portion may also include opening 2442 and opening 2444 through which barbs of a connector (not shown) may be inserted. Opening 2442 and opening 2444 may be configured to accommodate one or more barbs that pierce the upper wall of main vessel 2420 when the clenching force is applied. In another example, a lower portion of barb-setting device 2440 may be configured to compress a bottom wall of main vessel 2420. When compressed, the interior surface of the bottom wall of main vessel 2420 may contact connector 2430, thus causing barbs of connector 2430 to puncture main vessel 2420. In other examples, the above-described elements may be implemented differently and are not limited to the examples shown and described.

Figure 25:
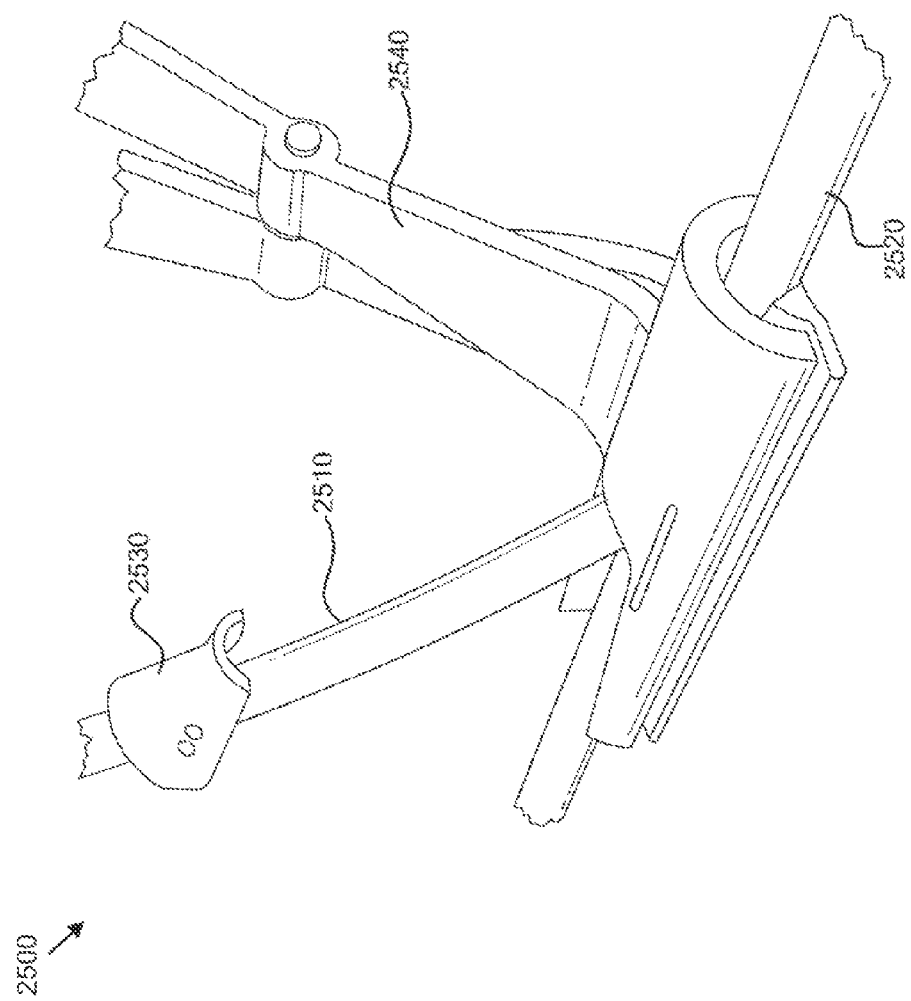
FIG. 25 illustrates an exemplary barb-setting device.

FIG. 25 illustrates an exemplary barb-setting device. Here, system 2500 may include graft vessel 2510, main vessel 2520, incision seal 2530, and barb-setting device 2540. In some examples, incision seal 2530 and barb-setting device 2540 may be implemented similarly or substantially similar in function and structure as like-named objects shown and described in FIG. 8 to FIG. 11, FIG. 23, and FIG. 24. As shown here, barb-setting device 2540 may be in a closed position. Barb-setting device 2540 may be configured to apply a clenching force to main vessel 2520. In some examples, the clenching force may cause one or more barbs of a connector disposed within main vessel 2520 to puncture a wall of main vessel 2520. In other examples, the above-described elements may be implemented differently and are not limited to the examples shown and described.

Figure 26:
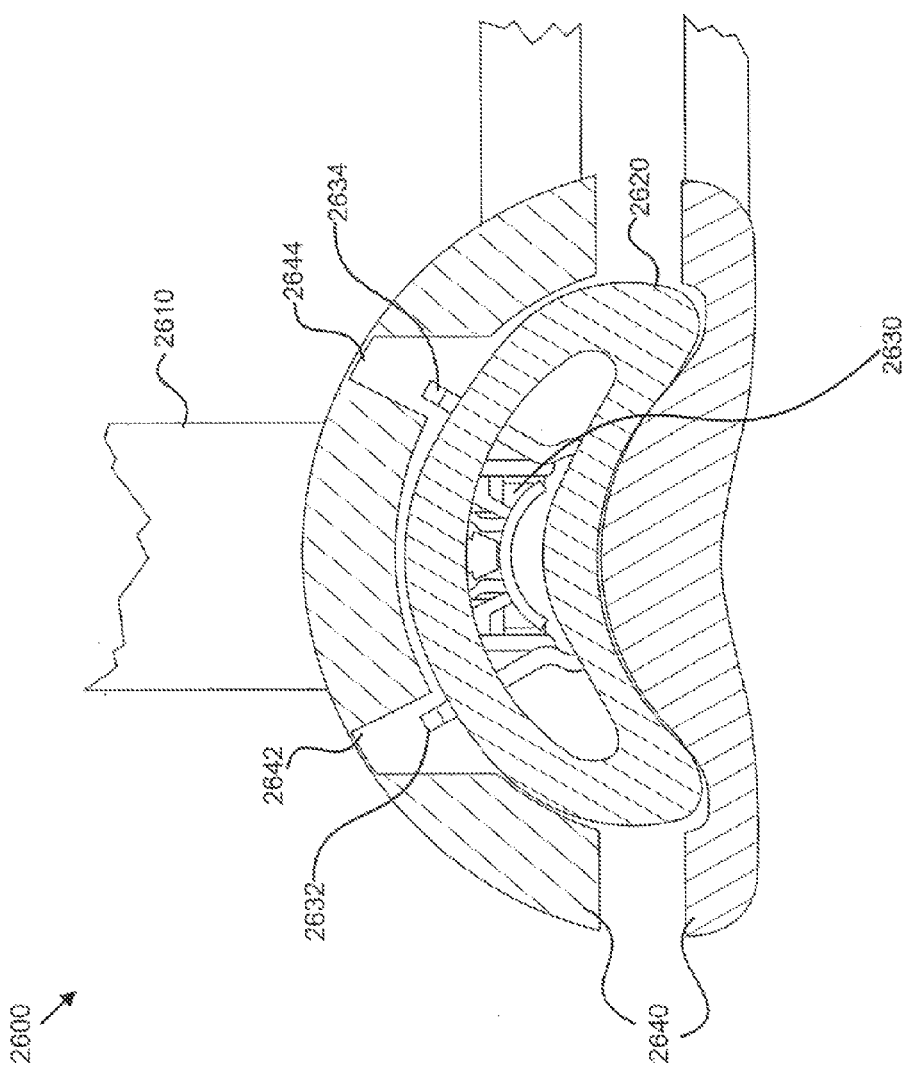
FIG. 26 illustrates a cross-sectional view of an exemplary barb-setting device.

FIG. 26 illustrates a cross-sectional view of a barb-setting device. Here, system 2600 may include graft vessel 2610, main vessel 2620, connector 2630, barb 2632, barb 2634, barb-setting device 2640, opening 2642 and opening 2644. In some examples, connector 2630, barb 2632, and barb-setting device 2640 may be implemented similarly or substantially similar in function and structure as like-named objects shown and described in FIG. 2 to FIG. 7, FIG. 13 to FIG. 16, FIG. 19 to FIG. 20, and FIG. 23 to FIG. 25. As shown here, barb-setting device 2640 may be in a closed position. Barb-setting device 2640 may be configured to provide a clenching force on the outer surface of main vessel 2620 causing main vessel 2620 to deform, compress, or otherwise change shape. Connector 2630 may be disposed within main vessel 2620 and securely coupled to graft vessel 2610. In some examples, main vessel 2620 may assume a shape that is substantially the same as the inner surface of the upper and lower components of barb-setting device 2640. In other examples, main vessel 2620 may assume other shapes. When in a compressed state, an inner surface of main vessel 2620 may contact connector 2630, thus causing connector 2630 to engage an inner surface of an upper wall of main vessel 2620. For example, a wing of connector 2630 may engage an inner surface of main vessel 2620 when main vessel 2620 is in a compressed state. In another example, barb 2632 and barb 2634 of connector 2630 may puncture a wall of main vessel 2620 when main vessel 2620 is in a compressed state. The punctured barbs may be disposed within opening 2642 and opening 2644 of barb-setting device 2640. When the clenching force is removed, main vessel 2620 may return to its original shape while connector 2630 remains engaged with an inner surface of an upper wall of main vessel 2620. For example, barb 2632 and barb 2634 may remain protruding from the exterior surface of main vessel 2620. In another example, wings or tines of connector 2630 may remain engaged with an inner surface of an upper wall of the main vessel. In yet other examples, the above-described elements may be implemented differently and are not limited to the examples shown and described.

Figure 27:
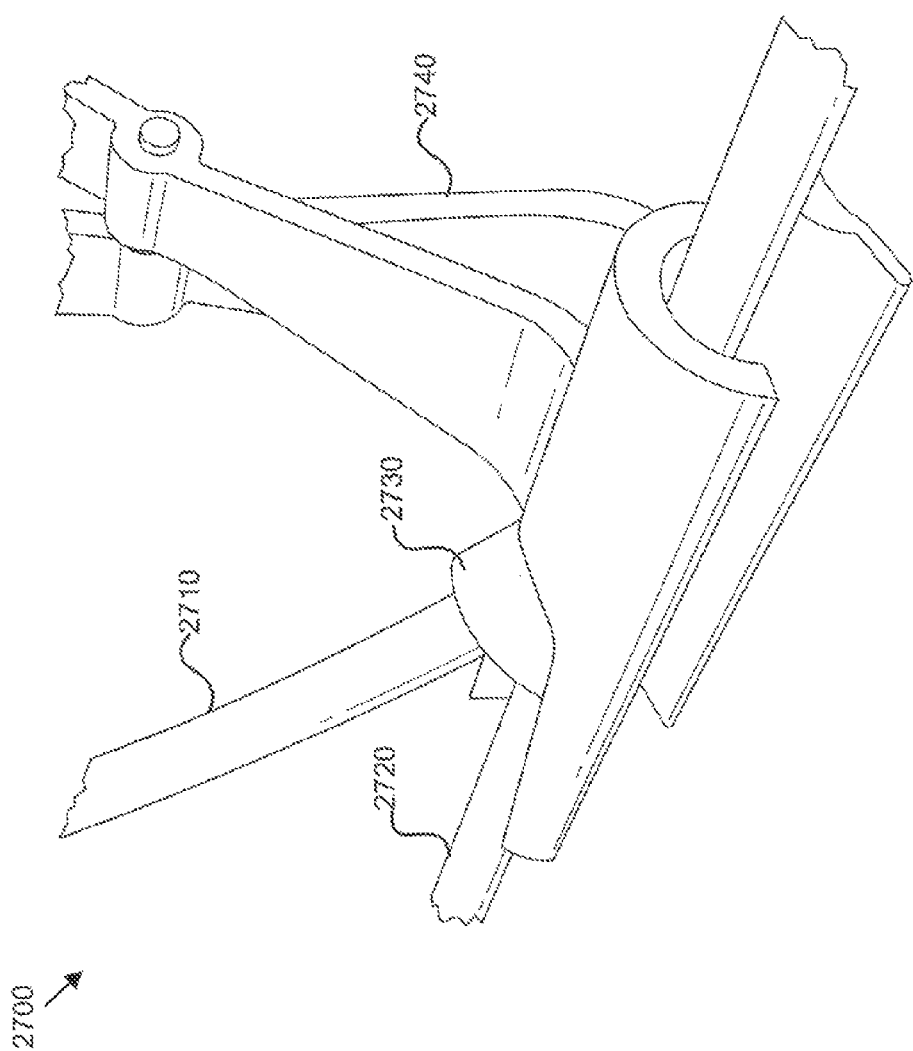
FIG. 27 illustrates an exemplary incision seal-setting device.

FIG. 27 illustrates an exemplary incision seal-setting device. System 2700 may include graft vessel 2710, main vessel 2720, incision seal 2730, and incision seal-setting device 2740. Incision seal 2730 may be implemented similarly or substantially similar in function and structure as like-named objects shown and described in FIG. 8 to FIG. 11. As shown here, incision seal-setting device 2740 may be in an open position. Incision seal-setting device 2740 may be configured to lock incision seal 2730 with a connector disposed within main vessel 2720. Incision seal 2730 may support graft vessel 2710 by encompassing graft vessel 2710. Incision seal 2730 may also cover a junction between graft vessel 2710 and main vessel 2720. Structurally, incision seal-setting device 2740 may include two components hinged together in a similar fashion as a traditional pair of pliers. The first component may include an end having a semi-cylindrical structure configured to longitudinally receive main vessel 2720 and incision seal 2730. In an example, the semi-cylindrical structure may be slotted on one end to receive graft vessel 2710 and incision seal 2730. The slot may allow the junction between graft vessel 2710 and main vessel 2720 to be disposed in the middle of the semi-cylindrical structure. The second component of incision seal-setting device 2740 may also be configured to longitudinally receive main vessel 2720. Together, the first component and second component may clench together incision seal 2730 with a connector within main vessel 2720, thus causing one or more barbs to lock with incision seal 2730. In some examples, the integrated structure (i.e., first and second components, incision seal 2730, and a connector (not shown)) may provide a clamping force on the portion of the main vessel between incision seal 2730 and the connector. In other examples, the above-described elements may be implemented differently and are not limited to the examples shown and described.

Figure 28:
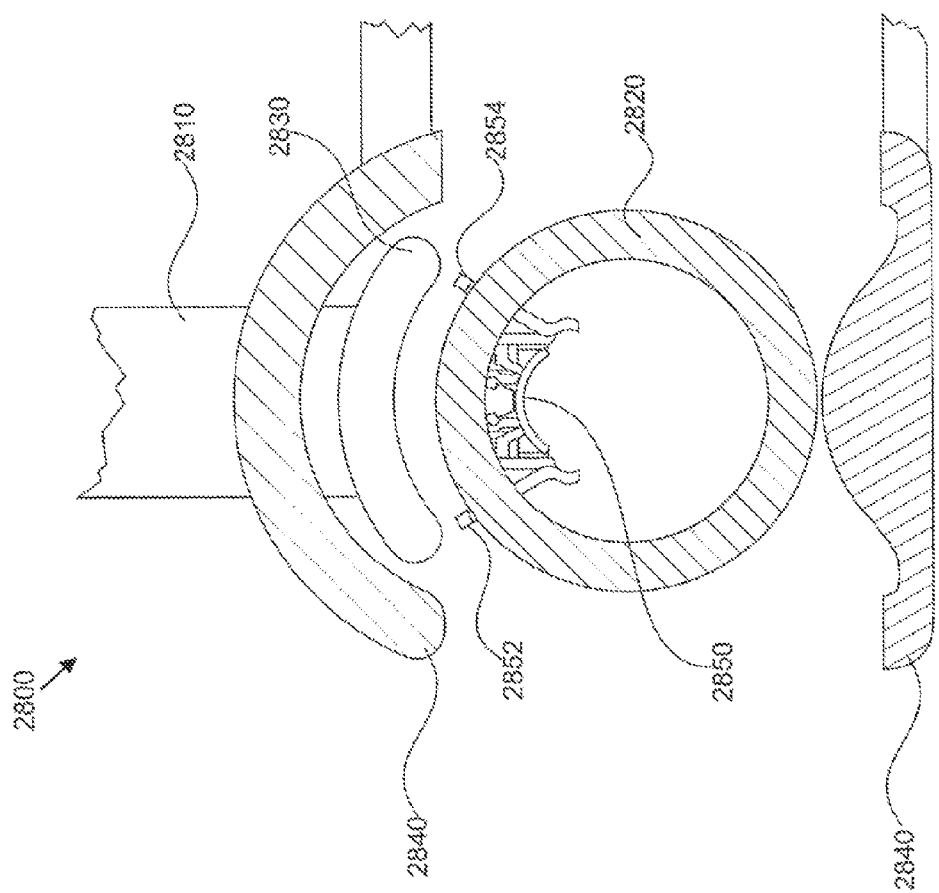
FIG. 28 illustrates a cross-sectional view of an exemplary incision seal-setting device.

FIG. 28 illustrates a cross-sectional view of an exemplary incision seal-setting device. Here, system 2800 is a general illustration that includes graft vessel 2810, main vessel 2820, incision seal 2830, incision seal-setting device 2840, connector 2850, barb 2852, and barb 2854. In some examples, incision seal 2830, incision seal-setting device 2840, connector 2850, barb 2852, and barb 2854 may be implemented similarly or substantially similar in function and structure as like-named objects shown and described in FIG. 2 to FIG. 16, FIG. 19 to FIG. 20, and FIG. 23 to FIG. 27. As shown here, incision seal-setting device 2840 may be in an open position. Incision seal 2830 may be disposed in a position allowing barb 2852 and barb 2854 of connector 2850 to lock with incision seal 2830 when a clenching force is applied to incision seal-setting device 2840. In some examples, an inner surface of incision seal-setting device 2840 may be configured to receive incision seal 2830 and main vessel 2820. In other examples, an inner surface of incision seal setting device 2840 may be configured to deform, compress, or otherwise change the shape of main vessel 2820. In yet other examples, the above-described elements may be implemented differently and are not limited to the examples shown and described.

Figure 29:
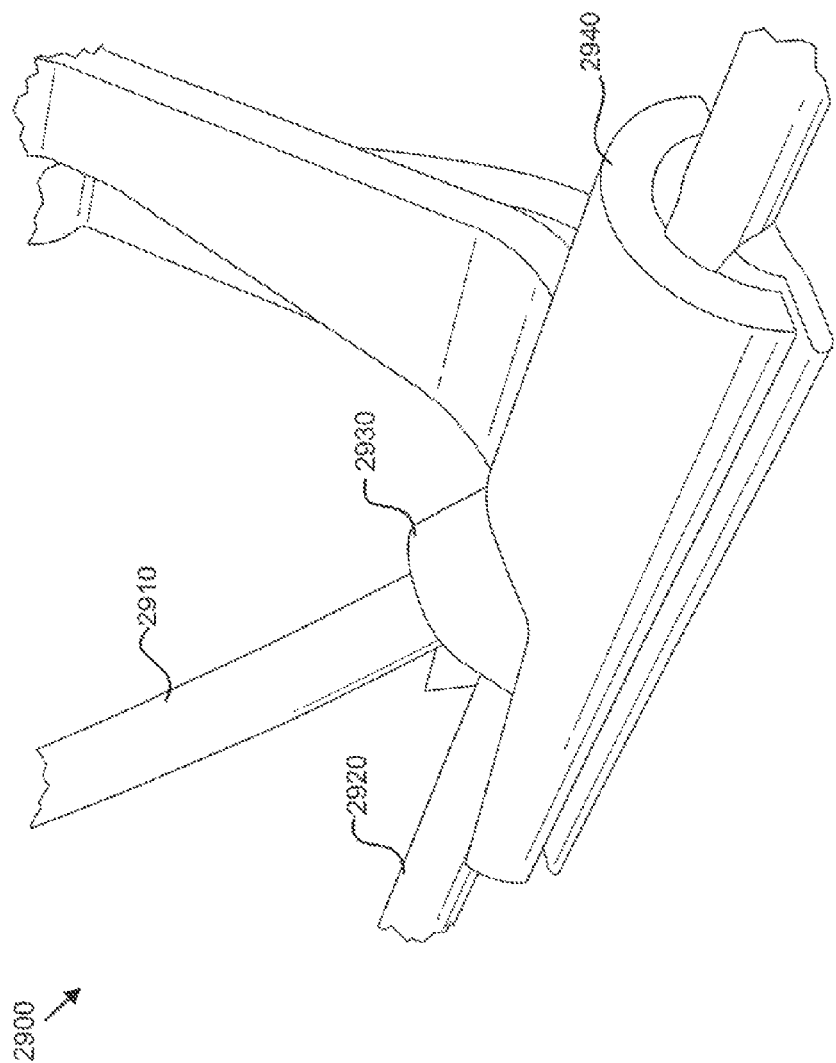
FIG. 29 illustrates an exemplary incision seal setting device.

FIG. 29 illustrates an exemplary incision seal-setting device. Here, system 2900 may include graft vessel 2910, main vessel 2920, incision seal 2930, and incision seal setting device 2940. In some examples, incision seal 2930 and incision seal-setting device 2940 may be implemented similarly or substantially similar in function and structure as like-named objects shown and described in FIG. 8 to FIG. 11 and FIG. 27 to FIG. 28. As shown here, incision seal setting device 2940 may be in a closed position. Incision seal setting device 2940 may be configured to apply a clenching force on main vessel 2920, incision seal 2930, and a connector within main vessel 2920. When the clenching force is applied, incision seal 2930 may lock with the connector. In some examples, incision seal 2930 and the connector may create a clamping force when locked. The clamping force may securely couple graft vessel 2910 to main vessel 2920. In some examples, the clenching force may affect a portion of main vessel 2920 overlapping incision seal 2930. In other examples, the clenching force may have no affect on portions of main vessel 2920 that do not overlap incision seal 2930. In yet other examples, the above-described elements may be implemented differently and are not limited to the examples shown and described.

Figure 30:
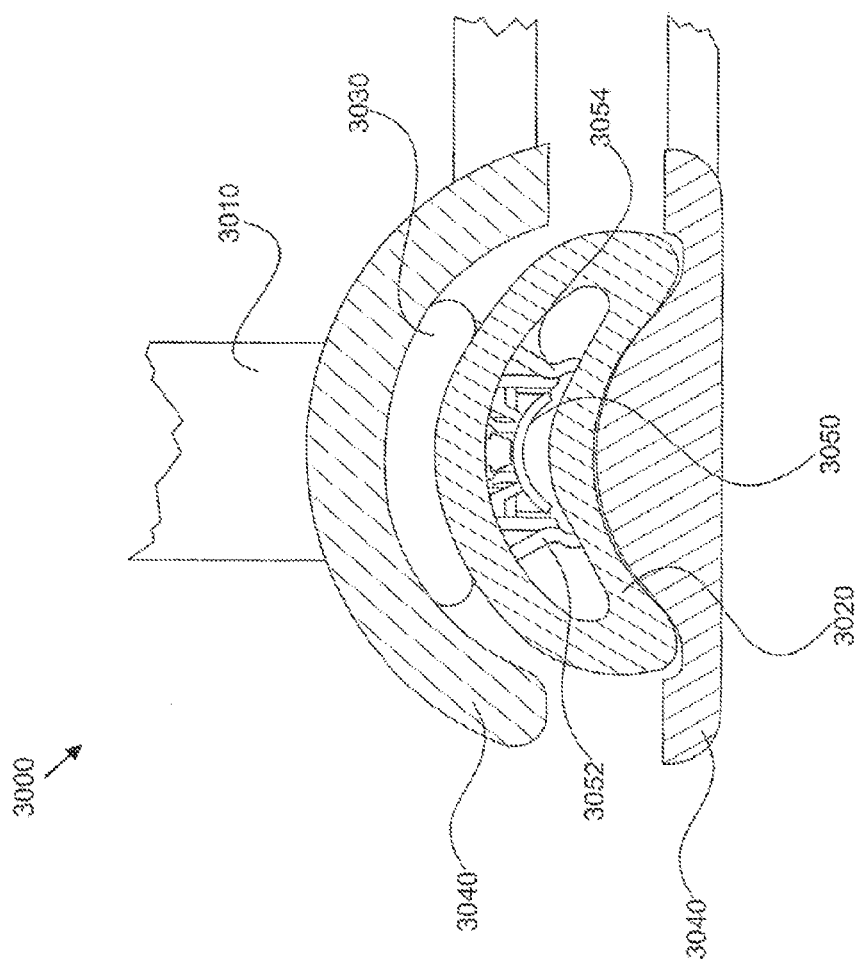
FIG. 30 illustrates an exemplary incision seal setting device.

FIG. 30 illustrates an exemplary incision seal setting device. Here, system 3000 may include graft vessel 3010, main vessel 3020, incision seal 3030, incision seal setting device 3040, connector 3050, barb 3052, and barb 3054. In some examples, incision seal 3030, incision seal setting device 3040, connector 3050, barb 3052, and barb 3054 may be implemented similarly or substantially similar in function and structure as like-named objects shown and described in FIG. 2 to FIG. 16, FIG. 19 to FIG. 20, and FIG. 23 to FIG. 29. As shown here, incision seal setting device 3040 may be in a closed position when a clenching force is applied. Incision seal setting device 3040 may be configured to lock connector 3050 with incision seal 3030. For example, incision seal setting device 3040 may compress main vessel 3020 to cause barb 3052 and barb 3054 to lock with incision seal 3030. In some examples, an interior surface of incision seal setting device 3040 may be configured to cause main vessel 3020 to deform, compress, or otherwise change shape. In other examples, the above-described elements may be implemented differently and are not limited to the examples shown and described.

Figure 31:
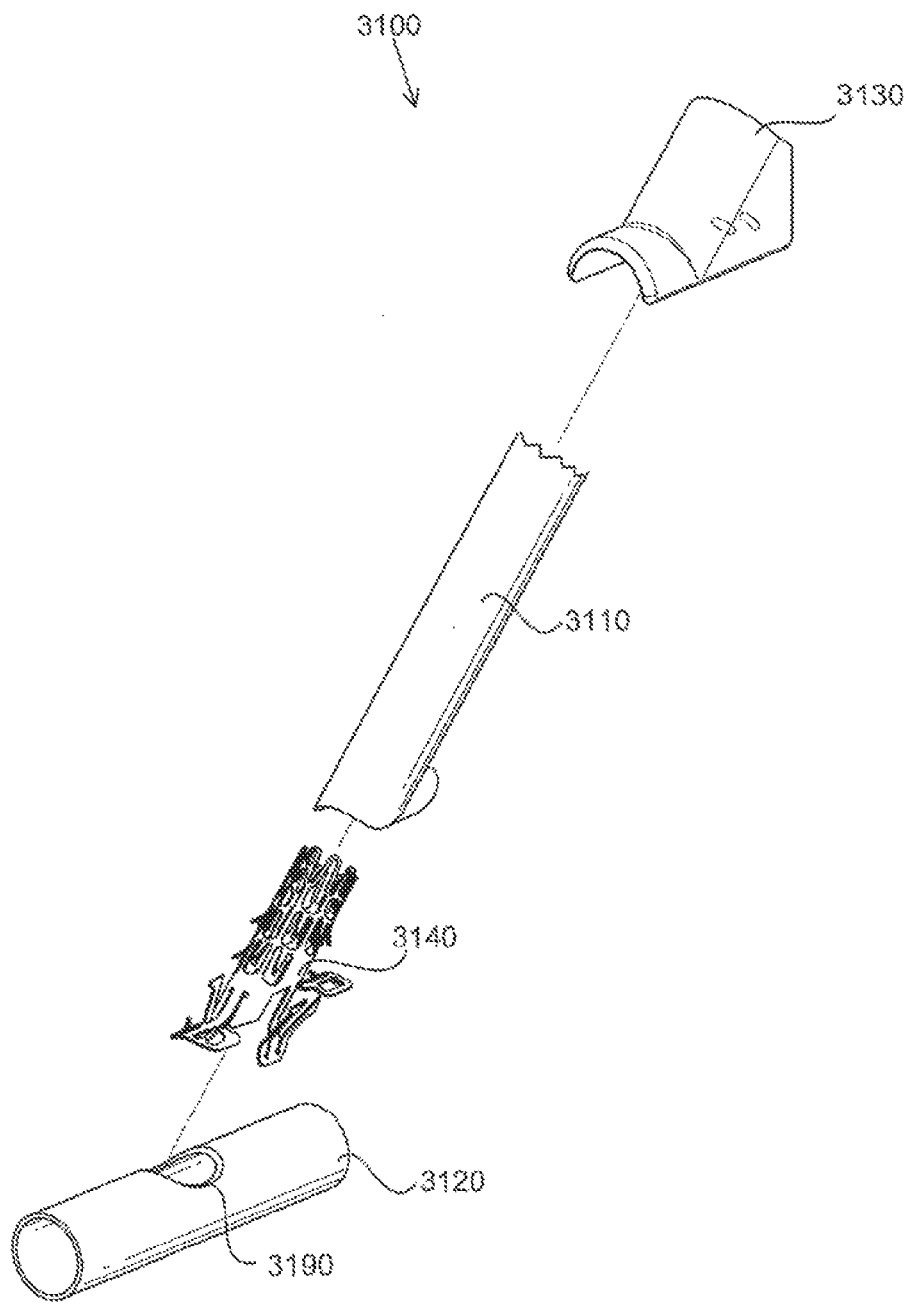
FIG. 31 illustrates an exploded view of an exemplary two-component sutureless vascular anastomosis connector system.

FIG. 31 illustrates an exploded view of an exemplary two-component sutureless vascular anastomosis connector system. Here, system 3100 may include graft vessel 3110, main vessel 3120, incision seal 3130, and connector 3140.

System 3100 may be configured to couple an end of graft vessel 3110 with incision 3190 along a wall of main vessel 3120. In some examples, incision seal 3130 and connector 3140 may be implemented similarly or substantially similar in function and structure as like-named objects shown and described in FIG. 2 to FIG. 16, FIG. 19 to FIG. 20, and FIG. 23 to FIG. 29. As shown here, graft vessel 3110 may be "sandwiched" (i.e., disposed between) in between incision seal 3130 aid connector 3140. In some examples, graft vessel 3110 may be securely held in between connector 3140 and incision seal 3130 when connector 3140 is in a deployed state (as shown in FIG. 31).

Main vessel 3120 may also be "sandwiched" (i.e., disposed between) in between incision seal 3130 and connector 3140 when connector 3140 is disposed within main vessel 3120. Connector 3140 and incision seal 3130 may be interlocked to provide a securing force that couples the connector 3140 to incision seal 3130. For example, the interlock may provide a securing force that secures main vessel 3120 in between connector 3140 and incision seal 3130. In some examples, connector 3140 may also provide a restraining force on the inner wall of main vessel 3120 that helps maintain the position of the wall of the main vessel relative to connector 3120. In yet another example, the interlock may provide sufficient pressure to minimize leakage from the end of graft vessel 3110, the incision in main vessel 3120, or any holes on the wall of the main vessel that may be covered by incision seal 3130. In other examples, the above-described elements may be implemented differently and are not limited to the examples shown and described.

Figure 32:
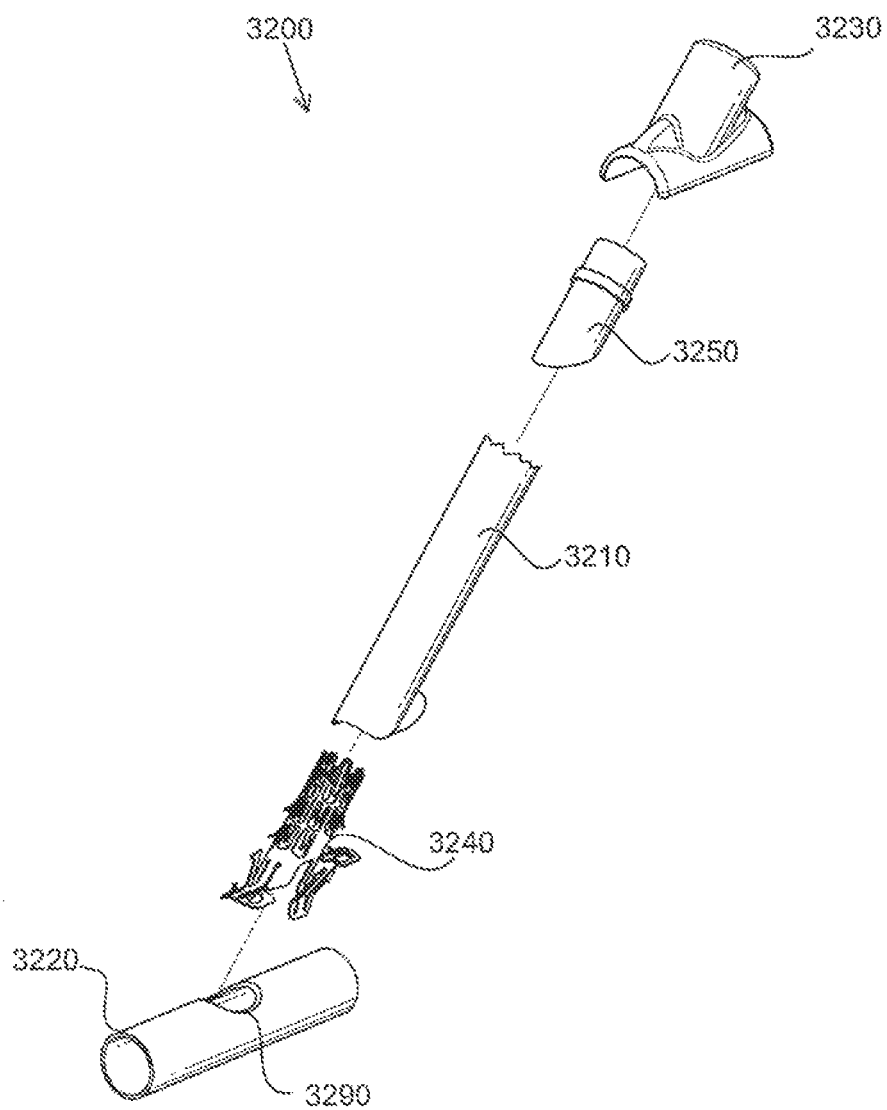
FIG. 32 illustrates an exploded view of an exemplary three-component sutureless vascular anastomosis connector system.

FIG. 32 illustrates an exploded view of an exemplary three-component sutureless vascular anastomosis connector system. Here, system 3200 may include graft vessel 3210, main vessel 3220, incision seal 3230, connector 3240, and support tube 3250. In some examples, incision seal 3230 and connector 3240 may be implemented similarly or substantially similar in function and structure as like-named objects shown and described in FIG. 2 to FIG. 16, FIG. 19 to FIG. 20, and FIG. 23 to FIG. 29. System 3200 may be configured to couple an end of graft vessel 3210 with incision 3290 along a wall of main vessel 3220. As shown here, graft vessel 3210 may be sandwiched in between support tube 3250 and connector 3240. In some examples, graft vessel 3210 may be securely held in between connector 3240 and support tube 3250 when connector 3240 is deployed (as shown in FIG. 32). Incision seal 3230 may be configured to receive support tube 3250 and securely couple with connector 3240 when connector 3240 is disposed within main vessel 3220. This may minimize leakage from being generated at or near the junction of the two vessels by providing additional support to the junction. For example, an end of support tube 3250 may firmly press the end of graft vessel 3240 against the wall of main vessel 3220 when incision seal 3230 is securely coupled with connector 3240. This may minimize leakage at the junction between the two vessels. As another example, incision seal 3230 may firmly cover an area of the wall of main vessel 3220 when incision seal 3230 is securely coupled with connector 3240. This may minimize leakage from holes in the area of the wall of main vessel 3220. In other examples, the above-described elements may be implemented differently and are not limited to the examples shown and described.

Figure 33:
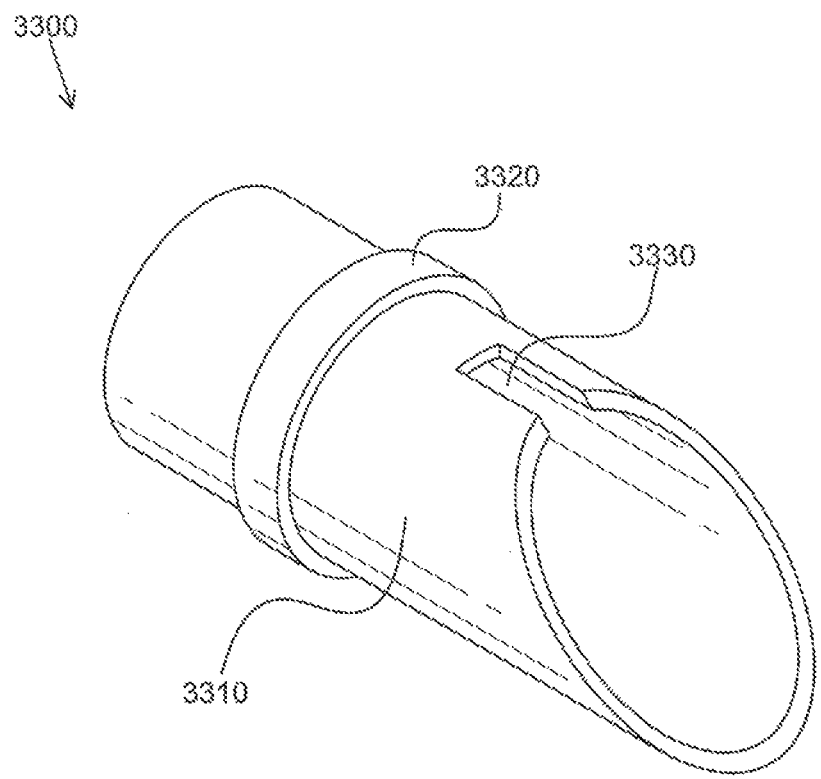
FIG. 33 illustrates an exemplary support tube.

FIG. 33 illustrates an exemplary support tube. Here, support tube 3300 may include body 3310, ring 3320, and notch 3330. Support tube 3300 may be configured to secure a graft vessel firmly to a main vessel. This may minimize leakage from the junction of the two vessels. As shown here, body 3310 may comprise of a hollow tube having an inner diameter and an outer diameter. The dimensions of body 3310 may be configured to allow body 3310 to be disposed in between a graft vessel and an incision seal. In some examples, the incision seal may be may be implemented similarly or substantially similar in function and structure to like-named elements as shown and described in FIG. 34. As an example, the inner diameter may be substantially similar to the outer diameter of the graft vessel, thereby allowing the graft vessel to fit snug within support tube 3300. As another example, the outer diameter may be configured such that body 3310 fits snug within a lumen in between first housing opening 3430 and second housing opening 3440 of incision seal 3400. In some examples, body 3310 may include an angled end. The angled end may be configured so that support tube 3300 may securely contact a wall of a main vessel at a pre-determined angle. As an example, the angled end may have substantially the same angle as an end of a graft vessel. The end of the graft vessel may be aligned with the angled end to allow the end of the graft vessel and support tube 3300 to securely contact the wall of the main vessel at the predetermined angle. In some examples, the angle at the end of the graft vessel, the angled end of body 3310, and an angle of a housing of an incision seal may all be substantially the same. This may allow all three to securely contact the wall of the main vessel.

In some examples, the length of body 3310 may be configured as a unit of measurement. For example, the length of body 3310 may be used as a guide to measure the approximate length of the portion of the graft vessel to be secured to a connector. This may be useful during the preparation of the graft vessel for vascular anastomosis (as discussed in FIG. 37). As an example, the length of body 3310 may be proportionate to the length of a portion of the connector to be coupled to the graft vessel. Thus, the length of body 3310 may be utilized as a measurement for determining a portion of the graft vessel that will be coupled to the connector. In some examples, the portion of the graft vessel measured may be folded over the exterior surface of body 3310 to subsequently be used to couple with the connector.

Support tube 3300 may further include ring 3320. Ring 3320 may be disposed along a circumference of body 3310. As an example, ring 3320 may be configured to couple with incision seal 3400. For example, ring 3320 may couple with groove 3450 of incision seal 3400 when support tube 3300 is received by incision seal 3400. When coupled, forces applied to incision seal 3400 may also be applied to support tube 3300. For example, a securing force applied to incision seal 3400 may also push support tube 3300 towards a wall of the main vessel. This may result in support tube 3300 firmly pressing an end of a graft vessel against the wall of the main vessel. In some examples, this may minimize leakage at the junction of the graft vessel and the main vessel. As an example, ring 3320 may be disposed along the outer surface of body 3310 depending on the location of groove 3450. For example, ring 3320 may be disposed at a position allowing incision seal 3400 and support tube 3300 to contact the wall of the main vessel when ring 3320 is coupled to groove 3450.

Support tube 3300 may further include notch 3330. Notch 3330 may be coupled to an angled end of body 3310 and may be configured to provide clearance for deployment of a wing belonging to a connector. In some examples, notch 3330 may provide clearance for rear hinge 641 to deploy rear wing 640 as shown and described in FIG. 6. Thus, the shape and position of notch 3330 may be dependent on the shape rear hinge 641. In another example, the shape and location of notch 3330 may be configured to support rear wing 640. In yet another example, body 3310, ring 3320, notch 3330, and angled edge 3340 may form a continuous tubular structure. The material used to form support tube 3300 may be Teflon tubing. In other examples, the above-described elements may be implemented differently and are not limited to the examples shown and described.

Figure 34:
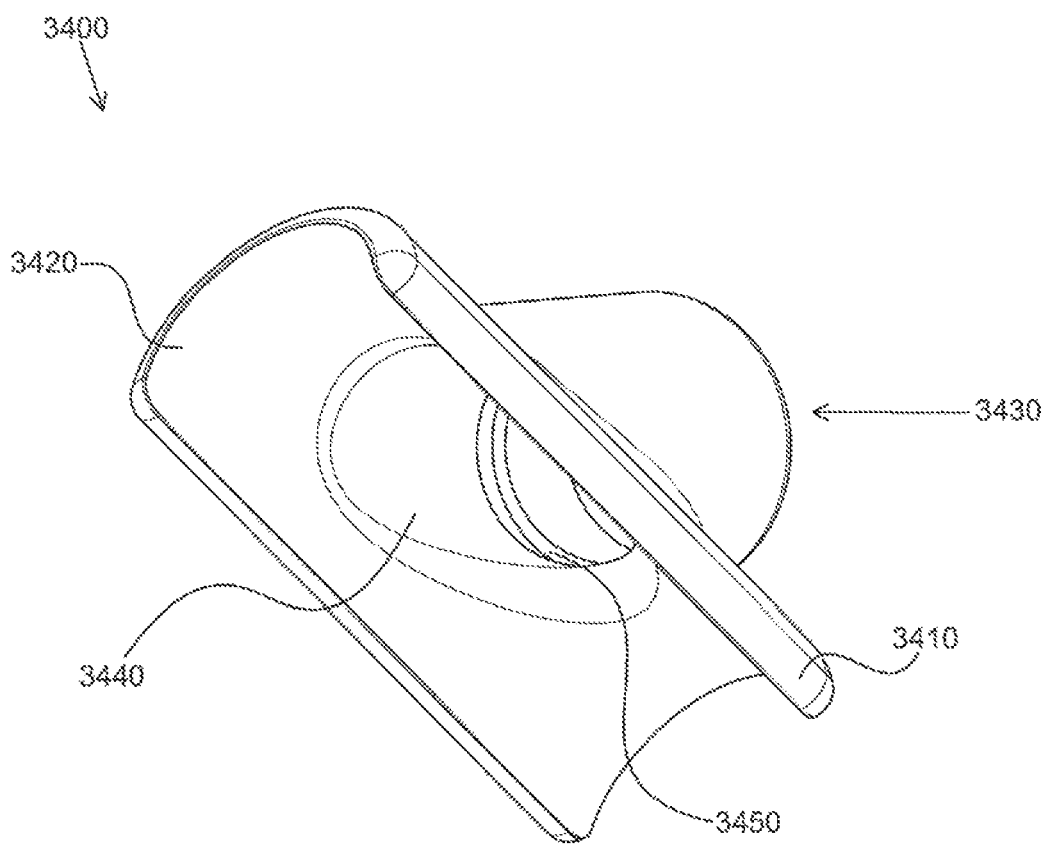
FIG. 34 illustrates an exemplary incision seal.

FIG. 34 illustrates an exemplary incision seal. Here, incision seal 3400 may include base 3410, recess 3420, first housing opening 3430, second housing opening 3440, and groove 3450. In some examples, base 3410, recess 3420, first housing opening 3430, and second housing opening 3440 may be implemented similarly or substantially similar in function and structure to like-named elements as shown and described in FIG. 8 and FIG. 9. As shown here, first housing opening 3430 may be disposed on an outer surface of incision seal 3400 and be configured to provide a lumen for objects inserted into first housing opening 3430 to reach second housing opening 3440, or vice versa. Second housing opening 3430 may be disposed on recess 3420 which is located along the length of base 3410. In some examples, first housing opening 3430 and second housing opening 3440 may be of different shapes or sizes. The different sizes may provide different functionality to the two ends of the lumen. For example, first housing opening 3430 may be configured to support the coupling of a connector and a graft vessel. In another example, second housing opening 3440 may be configured to support the coupling of the connector and a main vessel. As shown here, second housing opening 3440 may be triangular in shape and have rounded corners to accommodate the deployed wings or barbs of the connector (as shown and describe in FIGS. 2-7), thereby allowing the incision seal to seat securely on a wall of the main vessel when the wings or barbs of the connector are deployed.

Incision seal 3400 may further include groove 3450. Groove 3450 may be disposed within a lumen connecting first housing opening 3430 and second housing opening 3440. As an example, groove 3450 may be configured to contact a support tube inserted into second housing opening 3440. In some examples, the support tube may be implemented similarly or substantially similar in function and structure to support tube 3300 as shown and described in FIG. 33. When ring 3320 of support tube 3300 and groove 3450 are in contact, movements of incision seal 3400 may also affect support tube 3300. For example, support tube 3300 and incision seal 3400 may move in unison once contact has occurred. As an example, groove 3450 may be a recessed ring located within the lumen. The recessed ring may have a larger diameter than the diameter of the lumen. This may prevent support tube 3300 from passing entirely through the lumen between first housing opening 3430 and second housing opening 3440. In another example, groove 3450 may be protrusion located within the lumen. In yet other examples, groove 3450 may be any one or more shapes located within the lumen that prevents ring 3320 disposed on a body of the support tube from passing through.

Incision seal 3400 may comprise a medical grade material. In some examples, the medical grade material may be transparent. This may allow a surgeon to view the graft vessel and the main vessel when the two vessels are coupled to one another. This may also help the surgeon locate the source of any leakages creates from the coupling of the graft vessel and the main vessel. In other examples, the medical grade material may be malleable and capable of receiving and securely lodging an object within incision seal 3400. This may allow incision seal 3400 to securely engage with a connector without the use of slots or guides. In some examples, the connector may be implemented similarly or substantially similar in function and structure to the connector as shown and described in FIGS. 2-7. For example, barb 620 of FIG. 6 belonging to a connector 600 of FIG. 6 inserted inside a main vessel may pierce through a wall of the main vessel and enter incision seal 3400 at an entry point. Once the barb 620 enters the malleable material of incision seal 3400, barb 620 may be lodged within the malleable material, thus preventing removal of barb 620 from incision seal 3400. Depending upon the shape of barb 620, piercing the wall of the main vessel may create an opening in the wall that is of larger size than a base of barb 620. In some situations, the opening may result in leakage of fluids from inside the main vessel.

In some examples, the medial grade material may be configured to minimize the entry point of the fastener into incision seal 3400. This may allow incision seal 3400 to maintain a substantially smooth surface after barb 620 has entered incision seal 3400. As an example, the entry point may expand when presented with wider portions of the fastener and contract when presented with narrower portions of barb 620. This may result in the malleable material forming a seal around barb 620, regardless of the size or shape of the barb. Thus, when incision seal 3400 is seated on the wall of the main vessel, the substantially smooth surface of incision seal 3400 may cover any openings in the wall of the main vessel created from the fastener piercing the wall. This may minimize the leakage from any openings in the wall of the main vessel.

As an example, incision seal 3400 may comprise of a silicone based material. Barb 620 may pierce recess 3420 and become lodged (i.e. secured) within the silicone based material. As barb 620 enters incision seal 3400, the silicone based material may conform to the shape of barb 620, thus forming a tight seal between recess 3420 and the barb. The tight seal may provide a substantially smooth and uniform surface along recess 3420. This may allow recess 3420 to uniformly cover the wall of the main vessel, thus minimizing any leakage coming from the main vessel. As shown here, incision seal 3400 may be formed from a monolithic piece of material. In other examples, the above-described elements may be implemented differently and are not limited to the examples shown and described.

Figure 35:
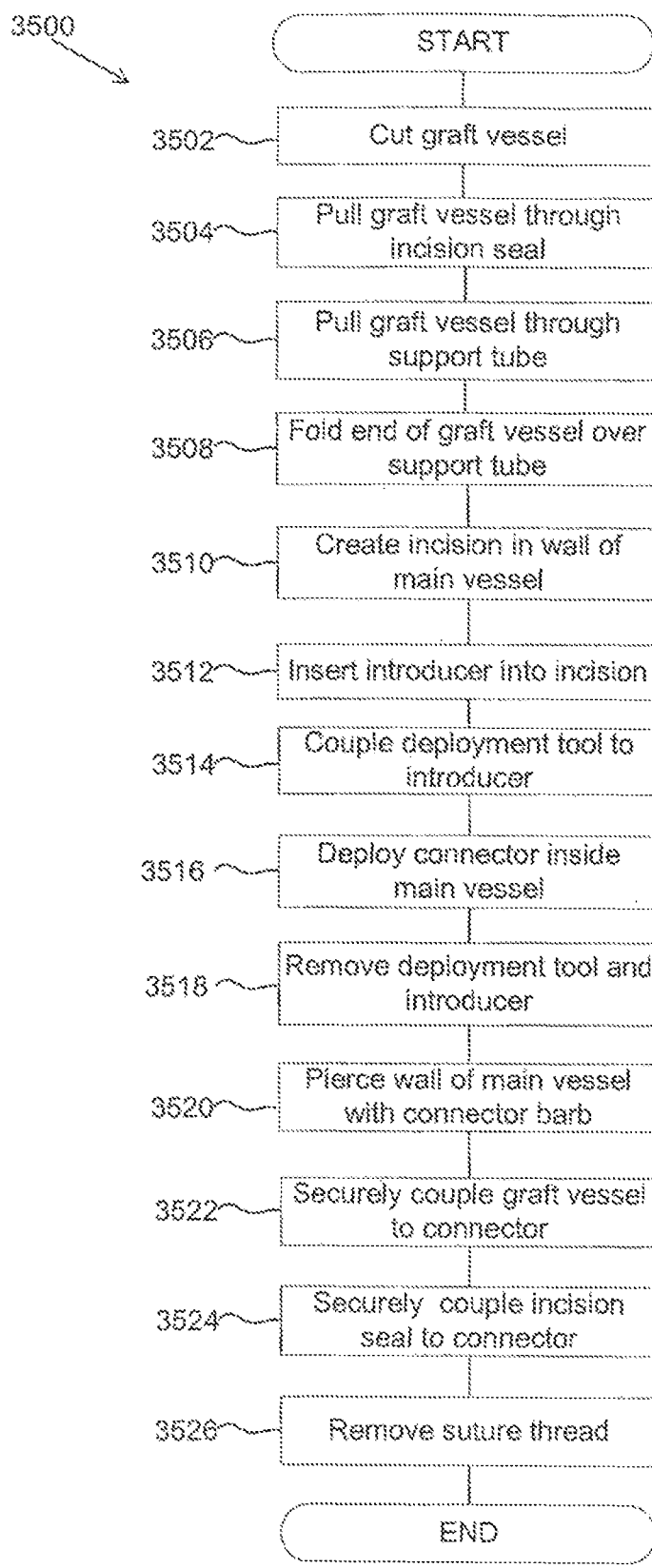
FIG. 35 illustrates a process flow diagram of an exemplary method for performing sutureless vascular anastomosis.

FIG. 35 illustrates a process flow diagram of an exemplary method for performing sutureless vascular anastomosis. Method 3500 may couple a graft vessel to an incision in a main vessel using a connector, an incision seal, and a support tube. In some examples, the connector, incision seal, and support tube may be implemented similarly or substantially similar in function and structure as like-named elements shown and described in FIG. 32 (e.g., graft vessel 3210, incision seal 3230, support tube 3250, connector 3240, main vessel 3220, and incision 3290), which is referenced for purpose of providing examples and like-named elements and varying descriptions may be found herein.

Here, method 3500 begins by cutting graft vessel 3210 at step 3502. Graft vessel 3210 may be interchangeably referred to as a "first vessel," a "donor artery," or "other vessel." As an example, graft vessel 3210 may be clamped at two points to stop the blood flow in a section of graft vessel 3210. This may help minimize blood loss from graft vessel 3210 during the vascular anastomosis procedure. As another example, graft vessel 3210 may be cut at an angle. The angle may be determined by the junction between graft vessel 3210 and the wall of main vessel 3220 and implemented at varying degrees (e.g., 15, 25, 35, 45, 90 degrees, or others). This may minimize leakage from the junction between graft vessel 3210 and main vessel 3220 by allowing graft vessel 3210 to securely contact the wall of main vessel 3220 at the junction. In other examples, the angle may be substantially the same as the angle determined by the plane of the end of support tube 3250 relative to the axis of the lumen or by the angle created by the junction of the lumen and the base of the incision seal. For example, the angle may be 10, 12, 27, 38, 45 or any other angular degree measurement.

After cutting graft vessel 3210, a cut end of graft vessel 3210 is pulled through incision seal 3230 at step 3504. In some examples, incision seal 3230 may be implemented similarly or substantially similar in function and structure as incision seal 3230 shown and described in FIG. 34. As an example, graft vessel 3210 may be pulled through a lumen of incision seal 3230 with the use of a precision grasping instrument. In some examples, the precision grasping instrument may be a pair of pliers or tweezers.

After pulling graft vessel 3210 though incision seal 3230, graft vessel 3210 is subsequently pulled through support tube 3250 at step 3506. In some examples, support tube 3250 may be implemented similarly or substantially similar in function and structure as the support tube shown and described in FIG. 33. Similar to step 3504, a grasping instrument may be used to pull graft vessel 3210 though support tube 3250.

After graft vessel 3210 is pulled through support tube 3250, the cut end of graft vessel 3210 is folded over support tube 3250 at step 3508. Graft vessel 3210 may be folded over the outer surface of support tube 3250 in preparation of securing graft vessel 3210 to connector 3240. For example, folding graft vessel 3210 over the length of the outer surface of support tube 3250 may apportion a segment (i.e. portion) of graft vessel 3210 that may later be used to securely couple graft vessel 3210 to connector 3240. In some examples, graft vessel 3210 may be oriented with respect to support tube 3250 before folding. For example, an angled end of support tube 3250 may be aligned with the angle of the cut end of graft vessel 3210 before folding. Properly orienting graft vessel 3210 and support tube 3250 in this manner may assist in ensuring that both the end of graft vessel 3210 and the end of support tube 3250 securely contact the wall of main vessel 3220 when graft vessel 3210 is coupled to main vessel 3220. This may minimize leakage at the junction of main vessel 3220 and graft vessel 3210. In some examples, a French dilator may used during the folding of graft vessel 3210. For example, the French dilator may be inserted into, graft vessel 3210 before graft vessel 3210 is folded over support tube 3250. This may provide a rigid support inside graft vessel 3210, thus simplifying manipulation of the position and orientation of graft vessel 3210. As an example, the French dilator may assist in aligning graft vessel 3210 and support tube 3250. In another example, the French dilator may assist in folding graft vessel 3210 over support tube 3250. The French dilator may be left within graft vessel 3210 to maintain the configuration of graft vessel 3210 and support tube 3250 until graft vessel 3210 is ready for use.

After graft vessel 3210 is folded over support tube 3250, incision 3290 is created on the wall of main vessel 3220 at step 3510. Incision 3290 may be created at a location where a surgeon wishes for graft vessel 3210 to couple with main vessel 3220. In some examples, incision 3290 may be created by piercing the wall of main vessel 3220 with a needle. The needle may comprise a hollow cylinder loaded with a guide wire configured to assist the insertion of connector 3240 into main vessel 3220. As an example, the needle may pierce the wall of main vessel 3220 at an angle that minimizes the likelihood of accidentally piercing through the opposite wall of main vessel 3220. The needle loaded with the guide wire may be inserted into main vessel 3220 and then removed while leaving the guide wire inside main vessel 3220. For example, the needle may pierce the wall of main vessel 3220, enter main vessel 3220 with the guide wire, and retract from main vessel 3220 leaving the guide wire inside main vessel 3220. A portion of main vessel 3220 surrounding the needle entry point may be clamped off prior to the incision. This may minimize the blood loss during the procedure.

After creating incision 3290 in main vessel 3220, an introducer is inserted into the incision at step 3512. The introducer may be configured to prepare the incision for insertion of connector 3240. After preparing the incision, a deployment tool may couple with the introducer and deploy connector 3240 within main vessel 3220. In some examples, the introducer may be threaded onto the guide wire and a tip of the introducer may be inserted into the incision. A dilator may be coupled to the tip of the introducer to ease the tip of the introducer inside main vessel 3220. Once the tip of the introducer is inside main vessel 3220, the dilator and the guide wire may be removed from main vessel 3220.

Figure 36:
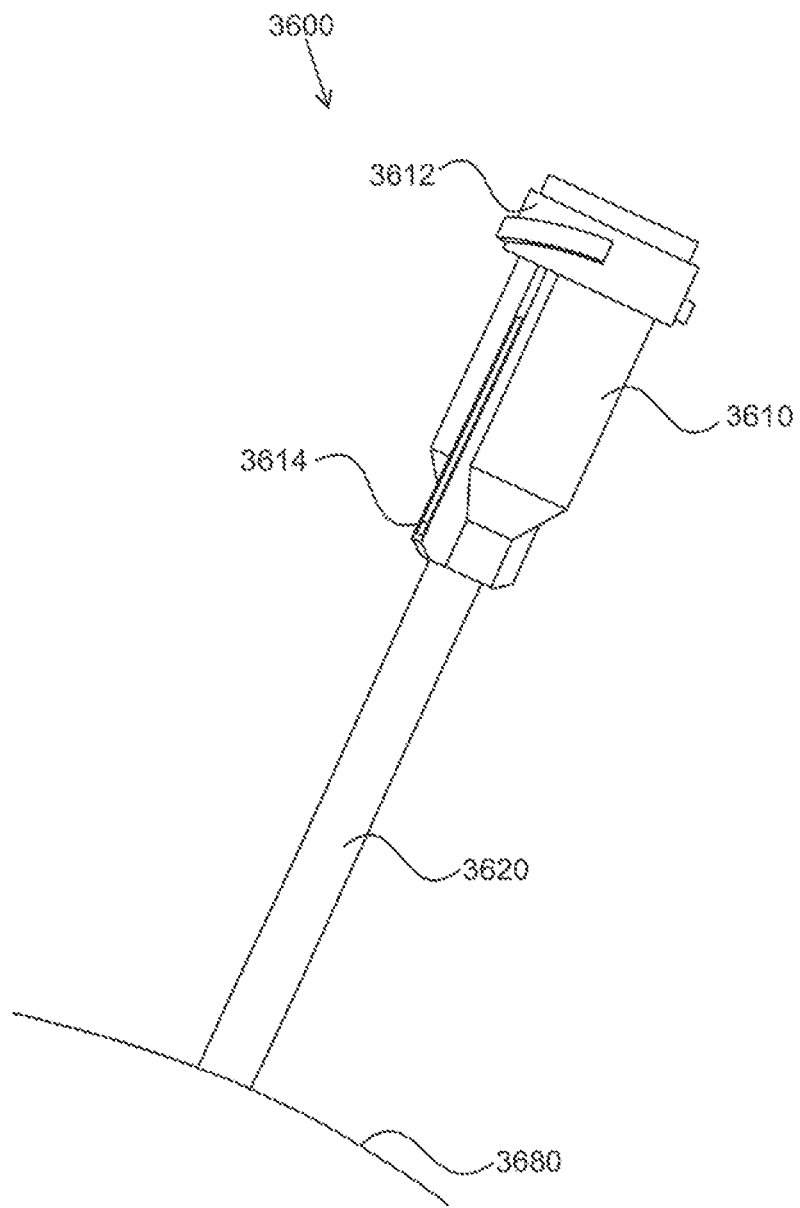
FIG. 36 illustrates an exemplary introducer.

FIG. 36 illustrates an exemplary introducer. Introducer 3600 may be configured to be inserted into an incision in a wall of a main vessel and to guide a deployment tool inside the main vessel. In some, examples, the deployment tool may be implemented similarly or substantially similar in function and structure as the syringe shown and described in FIG. 37 (discussed below). Here, introducer 3600 may include body 3610, locking mechanism 3612, alignment mark 3614, and introducer tip 3620. Body 3610 may comprise a hollow chamber having a wide opening and a narrow opening opposite of the wide opening. Body 3610 may be configured to receive a deployment tool through the wide opening. A portion of the deployment tool may be housed within the hollow chamber so that the two components are securely coupled together. In some examples, the hollow chamber may be of sufficient length such that when the portion of the deployment tool is received, the deployment tool and introducer 3600 are securely coupled. The narrow opening of body 3610 may be coupled to introducer tip 3620. Introducer tip 3620 may be a cylindrical tube configured to guide a deployment tool through an incision along the wall of main vessel 3680. In some examples, an end of the deployment tool may be located inside main vessel 3680 when the deployment tool is inserted into body 3610.

Body 3610 may be further coupled to locking mechanism 3612. Locking mechanism 3612 may be disposed along the wide opening of body 3610. In some examples, locking mechanism 3612 may be configured to interlock with the deployment tool. Once interlocked, the deployment tool and introducer 3600 may be securely coupled to one another. Thus, moving the deployment tool may also move introducer 3600, and vice versa. As an example, locking mechanism 3612 may be a male fitting or a female fitting of a male-female interconnect pair. The counterpart of the male-female interconnect pair may be disposed on the deployment tool. Thus, the deployment tool may be interlocked with the introducer by pressing together the male fitting and the female fitting and screwing together the male-female interconnect pair. In some examples, the male fitting and the female fitting may be tapered to minimize leakage of fluids traveling through the fittings. As shown here, locking mechanism 3612 may be a male luer lock fitting.

To ensure that introducer 3600 is properly connected to the deployment tool, body 3610 may also include alignment mark 3614. Alignment mark 3614 may be configured to align with another alignment mark located on the deployment tool. As an example, alignment mark 3614 may align with alignment mark 3715 of deployment tool 3700 shown in FIG. 37 when the male fitting and female fitting are properly aligned to be screwed together. This may provide a visual aid that introducer 3600 and the deployment tool are ready to be connected. As another example, alignment mark 3614 may align with alignment mark 3715 when the male fitting is securely connected with the female fitting. This may provide visual confirmation that the deployment tool and the introducer are properly connected. In other examples, introducer 3600 may be made of medical grade plastic materials, including Polyether ether ketone (PEEK). In other examples, the above-described elements may be implemented differently and are not limited to the examples shown and described.

Returning back to FIG. 35, a deployment tool is coupled to the introducer after the introducer is inserted into the incision at step 3514. The deployment tool may be a syringe or other device configured to deploy connector 3240. In some examples, the deployment tool may include a fitting configured to join with another fitting disposed on the introducer. When joined, the deployment tool and the introducer may be securely connected to one another. As an example, a tip of the deployment tool may be inserted into main vessel 3220 through a tip of the introducer when the deployment tool and the introducer are securely connected. In some examples, alignment marks are placed on both the introducer and the deployment tool to ensure that the two tools are properly connected.

Figure 37:
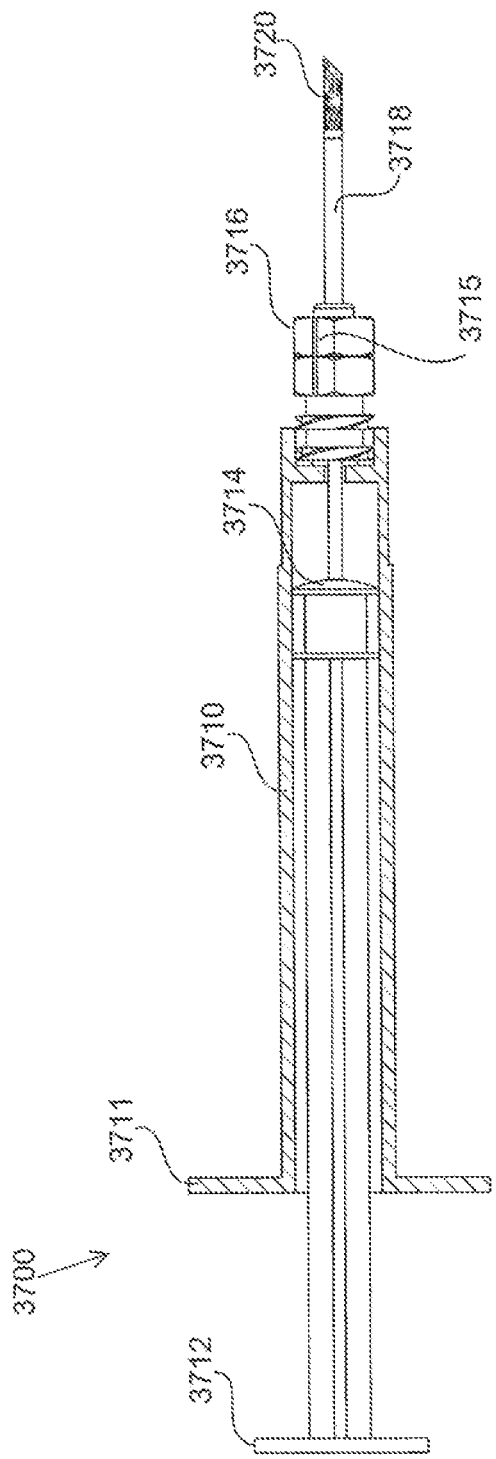
FIG. 37 illustrates an exemplary syringe preloaded with a connector.

FIG. 37 illustrates an exemplary syringe preloaded with a connector. Syringe 3700 may be configured to couple with an introducer and to deploy a connector inside a main vessel. In some examples, the introducer may be implemented similarly or substantially similar in function and structure as the introducer shown and described in FIG. 36. Here, syringe 3700 may include body 3710, handle 3711, plunger 3712, rod 3714, locking mechanism 3716, deployment tip 3718, and connector 3720. Syringe 3700 may be configured to deploy connector 3720 from deployment tip 3718 when plunger 3712 is depressed. As shown here, connector 3720 may be pre-loaded within deployment tip 3718 to save valuable time during surgery. In other examples, syringe 3700 may be reusable by loading connector 3720 within deployment tip 3718 prior to surgery.

Body 3710 may comprise of a hollow chamber with handle 3711 disposed towards one end. As an example, the hollow chamber may be configured to house plunger 3712. Plunger 3712 may be received through one end of body 3710. In some examples, plunger 3712 may include a safety pin (not shown) configured to prevent accidental deployment of connector 3720. For example, the safety pin may intersect plunger 3712 and contact an edge of handle 3711 when syringe 3700 is not ready for use. This configuration may prevent plunger 3712 from being depressed. The safety pin may be removed from plunger 3712 when syringe 3700 is ready for use. In some examples, body 3710 may comprise plastic, glass, or other synthetic or natural materials.

Plunger 3712 may be coupled to rod 3714. As shown here, rod 3714 may include an end configured to couple with plunger 3712 and an opposite end configured to deploy connector 3720. As an example, rod 3714 may push connector 3720 through deployment tip 3718 when plunger 3712 is depressed. Depressing plunger 3712 may push rod 3714 towards an end of deployment tip 3718 which in turn may push connector 3720 out of the end of deployment tip 3718. Thus, the rate of deployment of connector 3720 may depend upon the rate that plunger 3712 is depressed. As an example, one end of rod 3714 may be approximately the same shape as an end of plunger 2712. In another example, another end of rod 3714 may be approximately the same diameter as deployment tip 3718.

As shown here, body 3710 may be coupled to locking mechanism 3716. Locking mechanism 3716 may be configured to connect or interlock with an introducer. In some examples, the introducer may be implemented similarly or substantially similar in function and structure as the introducer shown and described in FIG. 36. As an example, locking mechanism 3716 may be a male fitting or a female fitting of a male-female interconnect pair. The counterpart of the male-female interconnect pair may be disposed on introducer 3600. This may allow introducer 3600 and syringe 3700 to securely interlock with one another when the male-female interconnect pair is threaded together. As shown here, locking mechanism 3716 may be a female luer lock fitting. As an example, connector 3720 may be located inside a main vessel when the introducer and syringe 3700 are securely coupled. In some examples, the male-female interconnect pair may be tapered to minimize leakage.

In some examples, locking mechanism 3716 may include an alignment mark 3715. Alignment mark 3715 may be configured to ensure that syringe 3700 is properly connected with introducer 3600 before connector 3720 is deployed. In some examples, a surgeon may infer information when alignment mark 3715 is aligned with alignment mark 3614 of introducer 3600. As an example, alignment of the alignment marks may confirm that the male-female interconnect pair are properly aligned to be screwed together. In another example, alignment of the alignment marks may confirm that the male-female interconnect pair are securely connected to one another and therefore, connector 3720 may be deployed by depressing plunger 3712. In yet other examples, the above-described elements may be implemented differently and are not limited to the examples shown and described.

Returning to FIG. 35, connector 3240 is deployed inside main vessel 3220 at step 3516. As an example, a plunger belonging to a deployment tool (as shown in FIG. 37) may be depressed to deploy connector 3240. In some examples, position of the deployment tool and the introducer may be manipulated prior to deployment to ensure that connector 3240 is deployed at the desired position inside main vessel 3220. For example, the introducer may be pulled out of the incision while leaving a tip of the deployment tool inside main vessel 3220. This may position the deployment of connector 3240 in the center of main vessel 3220 or any other desirable position for proper deployment of the wings and barbs belonging to connector 3240 inside main vessel 3220.

After connector 3240 is deployed inside main vessel 3220, the introducer (as shown in FIG. 36) and the deployment tool (as shown in FIG. 37) are removed from the incision at step 3518. In some examples, removing the deployment tool may deploy a portion of connector 3240 outside main vessel 3220. As an example, the portion of connector 3240 outside main vessel 3220 may include a suture thread. The suture thread may be used to seat connector 3240 along the wall of main vessel 3220.

After removing the introducer and the deployment tool, the wall of main vessel 3220 is pierced with a barb of connector 3240 at step 3520. Piercing the wall of main vessel 3220 with the barb may allow the barb to become accessible to incision seal 3230 located outside main vessel 3220. In some examples, piercing the wall of main vessel 3220 with the barb may include a two step process. In a first step, connector 3240 may be pulled by a suture thread attached to connector 3240. This may position the barb along the interior wall of main vessel 3220 and simplify the locating of the barb from the exterior wall of main vessel 3220. In a second step, a puncturing tool may be placed over the location of the barb to assist the barb through the wall of main vessel 3220. As an example, the puncturing tool may be a tube that is pressed firmly over the location of the barb while connector 3240 is pulled by the suture thread. These opposing forces may cause the barb to pierce through the wall of main vessel 3220. If there are multiple barbs, the puncturing tool may be used multiple times to pierce each barb through the wall of main vessel 3220.

After the barb of connector 3240 has pierced the wall of main vessel 3220, graft vessel 3210 is securely coupled to connector 3240 at step 3522. This may include orienting an edge of graft vessel 3210 to main vessel 3220 and securely coupling graft vessel 3210 to connector 3240. As an example, a dilator may have been used to maintain the configuration of graft vessel 3210 and support tube 3250 while main vessel 3220 was being operated on. If a dilator was used, the dilator may be removed before graft vessel 3210 is placed on top of connector 3240. In some examples, graft vessel 3210 may be placed on an end of connector 3240 and the portion of graft vessel 3210 folded over support tube 3250 may be unrolled over connector 3240. Advantages of unrolling graft vessel 3210 over connector 3240 instead of pulling graft vessel 3210 over connector 3240 may include minimizing traumatization to the interior wall of graft vessel 3210. A handling tool may be used to unroll graft vessel 3210 from support tube 3250 onto connector 3240. Examples of handling tools may include pliers, tweezers, or other precision grasping tools. In some examples, the length of support tube 3250 may be proportionate to the length of the portion of graft vessel used to securely couple with connector 3240. Once graft vessel 3210 is unrolled over connector 3240, support tube 3250 may slide down towards the junction between graft vessel 3210 and main vessel 3220. As an example, a piece of graft vessel 3210 may be sandwiched between support tube 3250 and main vessel 3220. This may provide a seal between the two vessels, thereby minimizing leakage at the junction. In another example, support tube 3250 may overlap the portion of connector 3240 contacting graft vessel 3210. The overlap of support tube 3250 and connector 3240 may sandwich the end of graft vessel 3210 in between support tube 3250 and connector 3240. This may provide a restraining force to securely couple graft vessel 3210 to connector 3240.

Once the graft vessel is attached to connector 3240, incision seal 3230 is securely coupled to connector 3240 at step 3524. In some examples, incision seal 3230 may be slid down over support tube 3250 and securely couple with one or more barbs of connector 3240 that are protruding from the wall of the main vessel (i.e. protruding barbs). For example, incision seal 3230 may receive the protruding barbs and secure the protruding barbs inside incision seal 3230. As an example, the protruding barbs may pierce through the surface of incision seal 3230 and become lodged within incision seal 3230. Once lodged, incision seal 3230 and connector 3240 may provide a clamping force that couples the graft vessel to main vessel 3220. The clamping force may also apply a constant downward pressure on support tube 3250. The downward pressure may minimize leakage from the junction by allowing support tube 3250 to firmly press the graft vessel on the wall of main vessel 3220. The downward force may also minimize the movement of the support tube after the procedure is complete.

After incision seal 3230 is securely coupled to connector 3240, the suture thread coupled to connector 3240 is removed at step 3526. As an example, the suture thread may be cut and removed. After removal of the suture thread, the clamps may be removed from the graft vessel and main vessel 3220, thereby returning blood flow.

As set forth above, measurements, dimensions, or other specifications may be varied and are not limited to those previously described. Variations in sizes, shapes, and processes may also be implemented and the above-described examples are also not intended to be limiting.

The foregoing examples have been described in some detail for purposes of clarity of understanding, but are not limited to the details provided. There are many alternative ways and techniques for implementation. The disclosed examples are illustrative and not restrictive.

What is claimed:

1. An incision seal for coupling an anastomosis connector with a main vessel and a graft vessel, the incision seal comprising:
   a base having opposing sides and a concave recess configured to partially cover the main vessel;
   a housing opening that intersects with the concave recess of the base, wherein the housing opening comprises a hollow cylindrical structure with an inner diameter configured to receive a graft vessel;
   a radius ring disposed around a circumference of an entrance of the housing opening and comprising a tapered surface from an outer edge with an outer diameter that is larger than the inner diameter of the housing opening to an inner edge located at the inner diameter of the housing opening, wherein the radius ring is configured to facilitate insertion of the graft vessel into the housing opening;
   a groove extending along an inner surface of a first side of the opposing sides of the base and configured to receive the anastomosis connector;
   a first guide channel disposed along a first edge of the groove;
   a second guide channel disposed along a second edge of the groove and parallel to the first guide channel;
   a first slot disposed on the first side of the base on the first guide channel;
   a second slot disposed on the first side of the base on the second guide channel and oriented in a different direction than the first slot;
   a third slot disposed on a second side of the opposing sides of the base; and
   at least a fourth slot disposed on the second side of the base and oriented in a different direction than the third slot,
   wherein the first, second, third and fourth slots are configured to lock with first, second, third and fourth barbs, respectively, on the anastomosis connector, and wherein each of the first, second, third and fourth slots comprises:
      an aperture in the base that forms a latching port configured to receive a respective one of the first, second, third and fourth barbs; and
      a latch pocket disposed adjacent to the latching port and configured to engage and lock with the respective one of the first, second, third and fourth barbs to prevent the locked barb from retracting back through the latching port by the latch pocket, wherein each of the guide channels is configured to guide one of the first, second, third and fourth barbs of the anastomosis connector along the groove and into one of the slots, and wherein the incision seal and the anastomosis connector are configured to form a seal between the graft vessel and the main vessel when the latch pockets of the slots have locked with the barbs of the anastomosis connector.

2. The incision seal of claim 1, wherein the base, the housing opening, and the first, second, third and fourth slots are monolithically formed as part of the incision seal.

3. The incision seal of claim 1, wherein the incision seal is formed using a medical-grade material.

4. The incision seal of claim 3, wherein the medical-grade material is malleable.

5. The incision seal of claim 1, wherein the incision seal is formed using an alloy.

6. The incision seal of claim 1, wherein the incision seal is formed using an alloy comprising at least nickel and titanium.

7. The incision seal of claim 1, further comprising the anastomosis connector, wherein the incision seal and the connector are formed of Nitinol.

8. The incision seal of claim 7, further comprising an incision seal setting device for connecting the incision seal to the anastomosis connector via the first, second, third and fourth barbs and the first, second, third and fourth slots.

9. The incision seal of claim 8, wherein the incision seal and the anastomosis connector are configured to sandwich the main vessel-between them when the incision seal is connected to the anastomosis device using the incision seal setting device.

10. The incision seal of claim 1, further comprising-an upper lumen configured to guide the graft vessel toward the housing opening.

11. The incision seal of claim 1, wherein the first, second, third and fourth barbs are configured to at least partially pierce the base to secure the incision seal to the anastomosis connector using a puncturing tool.

* * * * *